(12) United States Patent
Smith et al.

(10) Patent No.: US 11,534,488 B2
(45) Date of Patent: Dec. 27, 2022

(54) USE OF SEMAPHORIN-4D BINDING MOLECULES FOR MODULATION OF BLOOD BRAIN BARRIER PERMEABILITY

(71) Applicant: Vaccinex, Inc., Rochester, NY (US)

(72) Inventors: Ernest S. Smith, W. Henrietta, NY (US); Maurice Zauderer, Pittsford, NY (US)

(73) Assignee: VACCINEX, INC., Rochester, NY (US)

( * ) Notice: Subject to any disclaimer, the term of this patent is extended or adjusted under 35 U.S.C. 154(b) by 0 days.

(21) Appl. No.: 16/433,496

(22) Filed: Jun. 6, 2019

(65) Prior Publication Data

US 2019/0358321 A1 Nov. 28, 2019

Related U.S. Application Data

(63) Continuation of application No. 13/649,651, filed on Oct. 11, 2012, now abandoned.

(60) Provisional application No. 61/593,641, filed on Feb. 1, 2012, provisional application No. 61/555,726, filed on Nov. 4, 2011, provisional application No. 61/545,809, filed on Oct. 11, 2011.

(51) Int. Cl.
*C07K 16/28* (2006.01)
*A61K 39/395* (2006.01)
*A61K 45/06* (2006.01)
*A61K 39/00* (2006.01)

(52) U.S. Cl.
CPC .......... *A61K 39/3955* (2013.01); *C07K 16/28* (2013.01); *C07K 16/2803* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,070,192 A | 12/1991 | Earnshaw | |
| 5,595,756 A | 1/1997 | Bally | |
| 6,497,872 B1 | 12/2002 | Weiss | |
| 6,498,018 B1 | 12/2002 | Carpenter | |
| 6,541,255 B1 | 4/2003 | Snyder | |
| 6,576,754 B2 | 6/2003 | Hall | |

(Continued)

FOREIGN PATENT DOCUMENTS

| CN | 1329060 A | 1/2002 |
|---|---|---|
| CN | 1878793 A | 12/2006 |

(Continued)

OTHER PUBLICATIONS

Edwards BM, Barash SC, Main SH, et al. The remarkable flexibility of the human antibody repertoire; isolation of over one thousand different antibodies to a single protein, BLyS. J Mol Biol. 2003;334(1):103-118. (Year: 2003).*

(Continued)

*Primary Examiner* — Aurora M Fontainhas
(74) *Attorney, Agent, or Firm* — KDB Firm PLLC

(57) ABSTRACT

Provided herein are methods for decreasing blood-brain barrier permeability in a subject with a neuroinflammatory disorder, comprising administering to the subject an effective amount of an isolated binding molecule which specifically binds to semaphorin-4D (SEMA4D) or to its high affinity Plexin-B1 receptor.

9 Claims, 8 Drawing Sheets

Figure 1:
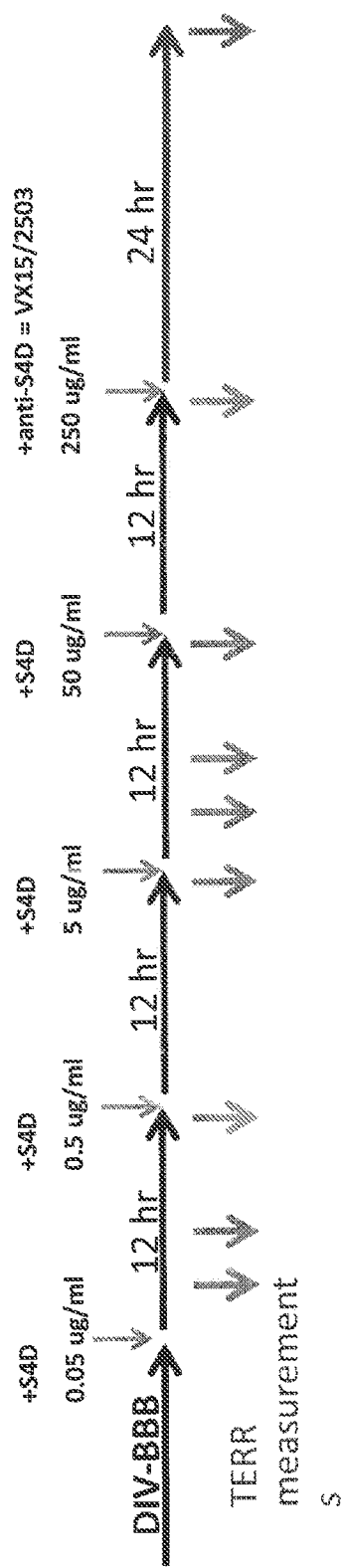

Specification includes a Sequence Listing.

(56) References Cited

U.S. PATENT DOCUMENTS

| | | |
|---|---|---|
| 6,635,742 B1 | 10/2003 | Boyle |
| 6,638,501 B1 | 10/2003 | Bjornson |
| 6,777,233 B2 | 8/2004 | Carpenter |
| 6,884,879 B1 | 4/2005 | Baca |
| 7,060,269 B1 | 6/2006 | Baca |
| 7,169,901 B2 | 1/2007 | Baca |
| 7,351,803 B2 | 4/2008 | Johnson |
| 7,407,766 B1 | 8/2008 | Fujisawa |
| 7,414,108 B2 | 8/2008 | Laus |
| 7,700,102 B2 | 4/2010 | Hall |
| 7,919,246 B2 | 4/2011 | Lai |
| 7,919,594 B2 | 4/2011 | Smith |
| 8,067,247 B2 | 11/2011 | Belin |
| 8,496,938 B2 | 7/2013 | Smith |
| 8,637,026 B2 | 1/2014 | Zauderer |
| 8,790,652 B2 | 7/2014 | Basile |
| 8,816,058 B2 | 8/2014 | Smith |
| 8,834,883 B2 | 9/2014 | Croy |
| 9,090,709 B2 | 7/2015 | Fisher |
| 9,243,068 B2 | 1/2016 | Evans |
| 9,249,227 B2 | 2/2016 | Smith |
| 9,371,352 B2 | 6/2016 | Porcelli |
| 9,382,327 B2 | 7/2016 | Smith |
| 9,447,191 B2 | 9/2016 | Takayanagi |
| 9,512,224 B2 | 12/2016 | Zauderer |
| 9,598,495 B2 | 3/2017 | Smith |
| 9,603,922 B2 | 3/2017 | Donda |
| 9,708,601 B2 | 7/2017 | Smith |
| 9,790,271 B2 | 10/2017 | Zauderer |
| 9,809,654 B2 | 11/2017 | Robert |
| 9,890,213 B2 | 2/2018 | Smith |
| 9,963,504 B2 | 5/2018 | Klimatcheva |
| 2002/0012903 A1 | 1/2002 | Goldman |
| 2002/0037851 A1 | 3/2002 | Fleckenstein |
| 2003/0158402 A1 | 8/2003 | Hall |
| 2005/0147612 A1 | 7/2005 | Yayon |
| 2006/0147449 A1 | 7/2006 | Brass |
| 2006/0233793 A1 | 10/2006 | Belin |
| 2007/0098707 A1 | 5/2007 | Kong-Beltran |
| 2007/0148177 A1 | 6/2007 | Fyfe |
| 2007/0154483 A1 | 7/2007 | Fyfe |
| 2008/0219971 A1 | 9/2008 | Smith |
| 2008/0219974 A1 | 9/2008 | Bernett et al. |
| 2009/0104193 A1 | 4/2009 | Lai |
| 2009/0181035 A1 | 7/2009 | Watts |
| 2010/0040617 A1 | 2/2010 | Brass |
| 2010/0285036 A1 | 11/2010 | Smith |
| 2012/0027758 A1 | 2/2012 | Belin |
| 2012/0064035 A1 | 3/2012 | Hadden |
| 2012/0082663 A1 | 4/2012 | Dennis |
| 2012/0270268 A1 | 10/2012 | Smith |
| 2013/0142810 A1 | 6/2013 | Basile |
| 2013/0274449 A1 | 10/2013 | Smith |
| 2013/0288927 A1 | 10/2013 | Smith |
| 2013/0302320 A1 | 11/2013 | Smith |
| 2014/0072578 A1 | 3/2014 | Smith |
| 2014/0099334 A1 | 4/2014 | Fisher |
| 2014/0303358 A1 | 10/2014 | Takayanagi |
| 2015/0044219 A1 | 2/2015 | Evans |
| 2015/0104462 A1 | 4/2015 | Zauderer |
| 2015/0110800 A1 | 4/2015 | Smith |
| 2016/0115240 A1 | 4/2016 | Evans |

FOREIGN PATENT DOCUMENTS

| | | |
|---|---|---|
| CN | 101310183 A | 11/2008 |
| EP | 1365018 A1 | 11/2003 |
| EP | 1442749 A1 | 8/2004 |
| JP | 2001157583 A | 6/2001 |
| JP | 2005500034 A | 1/2005 |
| JP | 2007308465 A | 11/2007 |
| JP | 5500944 B2 | 5/2011 |
| WO | 9314125 A1 | 7/1993 |
| WO | 9507706 A1 | 3/1995 |
| WO | 9717368 A1 | 5/1997 |
| WO | 00028016 A1 | 5/2000 |
| WO | 03100041 A1 | 12/2003 |
| WO | 2004067034 A1 | 8/2004 |
| WO | 2005000900 A1 | 1/2005 |
| WO | 2005055936 | 6/2005 |
| WO | 2006110594 | 10/2006 |
| WO | 2008025020 A2 | 2/2008 |
| WO | 2008100995 A1 | 8/2008 |
| WO | 2010129917 A2 | 11/2010 |
| WO | 2011159704 A1 | 12/2011 |
| WO | 2012157237 A1 | 11/2012 |
| WO | 2013148854 A1 | 10/2013 |
| WO | 2013170221 A1 | 11/2013 |
| WO | 2014209802 | 12/2014 |
| WO | 2015054628 | 4/2015 |
| WO | 2015061330 | 4/2015 |
| WO | 2017184951 | 10/2017 |
| WO | 2018026715 | 2/2018 |
| WO | 2018156509 | 8/2018 |

OTHER PUBLICATIONS

Kussie PH, Parhami-Seren B, Wysocki LJ, Margolies MN. A single engineered amino acid substitution changes antibody fine specificity. J Immunol. 1994;152(1):146-152. (Year: 1994).*

Argaw et al., VEGF-mediated disruption of endothelial CLN-5 promotes blood-brain barrier breakdown. Proceedings of the National Academy of Sciences Feb. 2009, 106 (6) 1977-1982 (Year: 2009).*

Aagaard et al., "RNAi Therapeutics: Principles, Prospects and Challenges", Advanced Drug Delivery Reviews, Mar. 4, 2007, pp. 75-86, vol. 59.

Advisory Action for U.S. Appl. No. 12/776,187 dated Mar. 6, 2013.

Alberts et al., "The Generation of Antibody Diversity", Molecular Biology of the Cell—4th Edition, 1-10, 2002, Garland Science, New York.

Anonymous, "NCT01764737: Evaluation of Safety, Tolerability and PK of VX15/2503 in Patients with MS", Aug. 2, 2013, whole document, Retrieved from the Internet: URL:http://clinicaltrials.gov/archive/NCT01764737/2013_08_02 Retrieved on Apr. 25, 2017.

Argaw et al., "VEGF-mediated disruption of endothelial CLN-5 promotes blood-brain barrier breakdown," PNAS, 2009, 106(6): 1977-1982, The National Academy of Sciences of the USA, United States.

Auerbach et al., "Angiogenesis Assays: Problems and Pitfalls", Cancer and Metastasis Reviews, 2000, pp. 167-172, vol. 19, Kluwer Academic Publishers.

Banks et al., "The blood-brain barrier and immune function and dysfunction," Neurobiology of Disease, 2010, pp. 26-32, vol. 37, Elsevier Inc.

Basile et al., "Semaphorin 4D Provides a Link Between Axon Guidance Processes and Tumor-Induced Angiogenesis", Proceedings of the National Academy of Sciences, Jun. 2006, pp. 9017-9022, vol. 103 No. 24, National Academy of Sciences.

Basile et al., "Class IV semaphores promote angiogenesis by stimulating Rho-initiated pathways through plexin-B," Cancer Research, 2004, pp. 5212-5224, vol. 64.

Basile et al., "Plexin-B1 Utilizes RhoA and Rho Kinase to Promote the Integrin-dependent Activation of Akt and Erk and Endothelial Cell Motility", Journal of Biological Chemistry, 2007, pp. 34888-34895, vol. 282 No. 48.

Basile et al., Semaphorin 4D/Plexin-B1 Induces Endothelial Cell Migration through the Activation of PYK2, Src, and the Phosphatidyl inositol 3-Kinase-Akt Pathway Molecular and Cellular Biology, 2005, pp. 6889-6898, vol. 25.

Baxter et al., "Activation Rules: The Two-Signal Theories of Immune Activation", Nature Reviews Immunology, Jun. 2002, pp. 439-446, vol. 2 No. 6.

Beam et al., "Blood, Brain, and Cerebrospinal Fluid Concentrations of Several Antibiotics in Rabbits with Intact and Inflamed Meninges," Antimicrobial Agents and Chemotherapy, 1977, pp. 710-716, vol. 12 No. 6, American Society for Microbiology, United States.

(56) References Cited

OTHER PUBLICATIONS

Billard et al., "Switch in the Protein Tyrosine Phosphatase Associated with Human CD 100 Semaphorin at Terminal B-Cell Differentiation Stage", Blood, Feb. 2000, pp. 965-972, vol. 95 No. 3, The American Society of Hematology, United States.
Bleck et al., "An Alternative Method for the Rapid Generation of Stable, High-Expressing Mammalian Cell Lines", Bioprocessing Journal, Sep.-Oct. 2005, pp. 36-42, vol. 5 No. 4, International Society for BioProcess Technology, United States.
Bork, "Powers and Pitfalls in Sequence Analysis: The 70% Hurdle", Genome Research, 2000, pp. 398-400, vol. 10, cold Spring Harbor Laboratory Press.
Bougeret et al., "Increased Surface Expression of a Newly Identified 150-kDa Dimer Early After Human T Lymphocyte Activation", The Journal of Immunology, Jan. 1992, pp. 318-323, vol. 148 No. 2, The American Association of Immunologists, United States.
Bowie et al., "Deciphering the Message in Protein Sequences: Tolerance to Amino Acid Substitutions", Science, Mar. 16, 1990, pp. 1306-1310, vol. 247 No. 4948.
Brand et al., "Collagen-Induced Arthritis", Nature Protocols, May 2007, pp. 1269-1275, vol. 2 No. 5, Nature Publishing Group, England.
Bretscher et al., "A Theory of Self-Nonself Discrimination", Science, Sep. 11, 1970, pp. 1042-1049, vol. 169 No. 3950.
Brown et al., "Tolerance to Single, but Not Multiple, Amino Acid Replacements in Antibody VH CDR2: A Means of Minimizing B Cell Wastage from Somatic Hypermutation?" Journal of Immunology, May 1996, pp. 3285-3291 at 3290 and Tables 1 and 2, vol. 156 No. 9, The American Association of Immunologists.
Burgess et al., "Possible Dissociation of the Heparin-Binding and Mitogenic Activities of Heparin-Binding (Acidic Fibroblast) Growth Factor-1 From Its Receptor-Binding Activities by Site-Directed Mutagenesis of a Single Lysine Residue", The Journal of Cell Biology, Nov. 1990, pp. 2129-2138, The Rockefeller University Press, United States.
Bussolino, F., et al., "Molecular mechanisms of blood vessel formation," Trends Biochem. Sci. 22(7):251-256, Elsevier Trends Journals, England (1997).
Callahan et al., "At the Bedside: CTLA-4- and PD-1-blocking Antibodies in Cancer Immunotherapy", Journal of Leukocyte Biology, Jul. 2013, pp. 41-53, vol. 94 No. 1.
Campos et al., "Ki-67 and CD 100 Immunohistochemical Expression is Associated with Local Recurrence and Poor Prognosis in Soft Tissue Sarcomas, Respectively", Oncology Letters, 2013, pp. 1527-1535, vol. 5.
Carmeliet, "Angiogenesis in health and disease," Nature Medicine, 2003, pp. 653-660, vol. 9 No. 6, Nature Publishing Company, United States.
Ch'ng et al., "Prognostic Significance of CD100 Expression in Soft Tissue Progression", Cancer, 2007, pp. 164-172 vol. 110 Issue 3.
Chabbert-De Ponnat Ei Al., "Soluble CD100 Functions on Human Monocytes and Immature Dendritic Cells Require Plexin C1 and Plexin B1, Respectively", International Immunology, 2005, pp. 439-447, vol. 4, Oxford University Press, England.
Chen et al., "Generation and Analysis of Random Point Mutations in an Antibody CDR2 Sequence: Many Mutated Antibodies Lose their Ability to Bind Antigen", Journal of Experimental Medicine, Sep. 1992, pp. 855-866, vol. 176.
Cheung et al., "Age-Related Macular Degeneration", Pharmacotherapy, 2013, pp. 838-855, vol. 33 No. 8 [Epub ahead of print], 18 pages.
Chodobski el al., "Blood-Brain Barrier Pathophysiology in Traumatic Brain Injury", Translational Stroke Research, Dec. 2011, pp. 492-516, vol. 2 No. 4.
Claesson-Welsh., "Novel Paths to Blood Vessel Formation", Blood, Jun. 2005, pp. 4153-4154, vol. 105 No. 11, The American Society of Hematology, United States.
Clark et al., "Discovery and Development of Janus Kinase (JAK) Inhibitors for Inflammatory Diseases", Journal of Medicinal Chemistry, Jan. 13, 2014, pp. 5023-5038, vol. 57, American Chemical Society.
Colman et al., "Effects of Amino Acid Sequence Changes on Antibody-Antigen Interactions", Research in Immunology, 1994, pp. 33-36, vol. 145.
Colton et al., "The Effects of NOS2 Gene Deletion on Mice Expressing Mutated Human AbPP," Journal of Alzheimer's Disease, 2008, pp. 571-587, vol. 15 No. 4, IOS Press, Netherlands.
Combes et al., "The Crossroads of Neuroinflammation in Infectious Diseases: Endothelial Cells and Astrocytes", Trends in Parasitology, Aug. 2012, pp. 311-319, vol. 28 No. 8.
Conrotto et al., "Sema4D Induces Angiogenesis Through Met Recruitment by Plexin B1", Blood, Jun. 2005, pp. 4321-4329, vol. 105 No. 11, The American Society of Hematology, United States.
Cornelius et al., "Abstract 936: Nonclinical Safety and Pharmacology of VX15/2503: a Humanized IgG4 Monoclonal Antibody to SEMA4D", Cancer Research, Apr. 15, 2012, retrieved from http://cancerres.aacrjournals.org/content/72/8_Supplement/936.short on Sep. 25, 2015, the whole document.
Cucullo et al., "Development of a Humanized In Vitro Blood-Brain Barrier Model to Screen for Brain Penetration of Antiepileptic Drugs," Epilepsia, 2007, pp. 505-516, vol. 48 No. 3, Blackwell Publishing, Inc., England.
Cucullo, L. et al. "A new dynamic in vitro model for the multidimensional study of astrocyte-endothelial cell interactions at the blood-brain barrier," Brain Research 957:243-254, Elsevier Science B.V. (2002).
Cucullo, L., et ah, "A dynamic in vitro BBB model for the study of immune cell trafficking into the central nervous system," Journal of Cerebral Blood Flow & Metabolism 31:161-111, Nature Publishing Group, United States (2011), Epub. Sep. 15, 2010.
Curran et al., "Systemic 4-1BB Activation Induces a Novel T cell Phenotype Driven by High Expression of Eomesodermin", The Journal of Experimental Medicine 2013, pp. 743-755, vol. 210.
Dacquin et al., "Control of Bone Resorption by Semaphorin 4D is Dependent on Ovarian Function", PLOS One, Oct. 26, 2011, pp e26627, vol. 6 No 10.
Database GenBank, Apr. 18, 2005, ADAMS, "M.musculus mRNA for Semaphorin B", Data Accession No. X85991.
Database GenBank, Apr. 24, 1997, Hillier et al., "zt85a06.r1", Data Accession No. AA394007.
Database GenBank, Jan. 31, 1997, STRAUSBERG, "zs16g08.r1", Data Accession No. AA262446.
De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology 169(6):3076-3084, The American Association of Immunologists, Inc., United States (2002).
Deaglio et al., "CD38 and CD100 Lead a Network of Surface Receptors Relaying Positive Signals for B-CLL Growth and Survival", Blood, Apr. 2005, pp. 3042-3050, The American Society of Hematology, United States.
Deane et aL., "LRP/Amyloid b-Peptide Interaction Mediates Differential Brain Efflux of Ab Isoforms," Neuron, 2004, p. 333-344, vol. 43, Cell Press, United States.
Delaire et al., "Biological Activity of Soluble CD100. II Soluble CD100, Similarly to H-Sema III, Inhibits Immune Dell Migration", The Journal of Immunology, Jan. 2001, pp. 4348-4354, vol. 166, The American Association of Immunologists, United States.
Young et al., "Efficient Isolation of Genes by Using Antibody Probes", Proceedings of the National Academy of Sciences, Mar. 1983, pp. 1194-1196, vol. 80, National Academy of Sciences, United States.
Yu et al., "Interaction Between Bevacizumab and Murine VEGF-A: A Reassessment", Investigative Ophthalmology & Visual Science, Feb. 2008, pp. 522-527, vol. 49 No. 2.
Zhang et al., "Sema 4D/CD100-plexin B is a Multifunctional Counter-Receptor", Cellular and Molecular Immunology, 2013, pp. 97-98, vol. 10.
Zhong Ei Al., "ALS-causing SOD1 mutants generate vascular changes prior to motor neuron degeneration," Nature Neuroscience, 2008, pp. 420-422, vol. 11 No. 4, Nature Publishing Group, United States.

(56) References Cited

OTHER PUBLICATIONS

Zhou et al., "Semaphorin 4D Cooperates with VEGF to Promote Angiogenesis and Tumor Progression", Angiogenesis, 2012, pp. 391-407, vol. 15 Issue 3.

Zhu et al., "Semaphorin 4D (CD100) Is Expressed on the Surface of Human Platelets and Proteolytically Shed During Platelet Activation", Blood, Nov. 2003, Abstract No. 1043, vol. 102 No. 11, The American Society of Hematology, United States (Abstract Only).

Zlokovic, "Neurovascular Pathways to Neurodegeneration in Alzheimer's Disease and other Disorders", Nature Reviews-Neuroscience, Dec. 2011, pp. 723-738, vol. 12.

Zlokovic, B.V., "The Blood-Brain Barrier in Health and Chronic Neurodegenerative Disorders," Neuron, 2008, pp. 178-201, vol. 57, Elsevier Inc., United States.

Vezzani et al., "The Role of Inflammation in Epilepsy", Nature Reviews Neurology, Jan. 2011, pp. 31-40, vol. 7 No 1.

Okuno et al., The role of immune semaphorins in multiple sclerosis. FEBS Letters 585 (2011) 3829-3835.

Delaire et al., "Inhibition of Immune Cell Migration by Soluble CD100 and H-Sema III Semaphorins", Tissue Antigens, 2000, p. 103, vol. 55 No 1, Wiley-Blackwell, England (Abstract Only).

Dickson, B.J., "Molecular Mechanisms of Axon Guide," Science, 2002, pp. 1959-1964, vol. 298, No. 5600.

Dougher, M: and I Erman, B.I., "Autophosphorylation of KDR in the kinase domain is required for maximal VEGF-stimulated kinase activity and receptor internalization," Oncogene 18(8):1619-1627, Nature Publishing Group, England (1999).

Drake et all., "Mechanisms of Immune Evasion by Tumors", Advances in Immunology, 2006, pp. 51-81, vol. 90.

Duran-Struuck et al., "A Novel Role for the Semaphorin Sema4D in the Induction of Allo-Responses", Biological Blood Marrow Transplant, Nov. 2007, pp. 1294-1303, vol. 13 No. 11.

Elhabazi et al., "Biological Activity of Soluble CD100.1. The Extracellular Region of CD100 is Released from the Surface of T Lymphocytes by Regulated Proteolysis", The Journal of Immunology, Jan. 2001, pp. 4341-4347, vol. 166, The American Association of Immunologists, United States.

Elhabazi et al., "Structure and Function of the Immune Semaphorin CD100/SEMA4D", Critical Review in Immunology, 2003, pp. 65-81, vol. 23 No. 1-2, Bege II House, Inc. United States.

Elhabazi, A., et al., "The Human Semaphorin-like Leukocyte Cell Surface Molecule CD100 Associates with a Serine Kinase Activity," The Journal of Biological Chemistry 272(38):23515-23520, The American Society for Biochemistry and Molecular Biology, Inc., United States (2003).

Engelhardt et al., "Capture, Crawl, Cross: The T Cell Code to Breach the Blood-Brain Barriers", Trends in Immunology, Dec. 2012, pp. 579-589, vol. 33 No. 12.

Fabis et al., "Loss of Blood-Brain Barrier Integrity in the Spinal Cord is Common to Experimental Allergic Encephalomyelitis in Knockout Mouse Models," Proceedings of the National Academy of Sciences of the United States of America, pp. 5656-5661, vol. 104, No. 13, Mar. 27, 2007.

Fanning et al., "Development of the Immunoglobulin Repertoire", Clinical Immunology and Immunopathology, Apr. 1, 1996, pp. 1-14, vol. 79 No. 1.

Ferrara, N., "VEGF and the quest for tumour angiogenesis factors," Nat. Rev. Cancer 2(10)795-803, Nature Pub. Group, England (2002).

Ferrara, N., et al., "The biology of VEGF and its receptors," Nat. Med. 9(6):669-676, Nature Publishing Company, United States (2003).

Fisher et al., "Development of An Anti-SEMA4D Monoclonal Antibody for the Treatment of Multiple Sclerosis", 5th Joint Triennial Congress of the European and Americas Committees for Treatment and Research in Multiple Sclerosis, Oct. 19,2011-Oct. 22, 2011, Amsterdam, The Netherlands, retrieved from http://registration akm.ch/einsicht.php?XNABSTRACT_ID=138346 &XNSPRACCHE on Jun. 10, 2015.

Fishwild et al., "High-Avidity Human IgGK Monoclonal Antibodies from a Novel Strain of Minilocus Transgenic Mice", Nature Biotechnology, May 1996, pp. 845-851, vol. 14, Nature Publishing Group, United States.

Fong et al., "Potentiating Endogenous Antitumor Immunity to Prostate Cancer through Combination Immunotherapy with CTLA4 Blockade and GM-CSF", Cancer Research, Jan. 15, 2009, pp. 609-615, vol. 69, Issue 2.

Fonsatti et al., "Highlights on Endoglin (CD105): From Basic Findings Towards Clinical Application in Human Cancer", Journal of Translational Medicine, 2004, 7 pages, vol. 2 No. 18.

Fujioka et al., "Neurotrophic Effect of Semphorin 4D in PC12 Cells", Biochemical and Biophysical Research Communications, Feb. 2003, pp. 304-310, vol. 301 No. 2, Elsevier Science, United States.

Furuyama et al., "Identification of a Novel Transmembrane Semaphorin Expressed on Lymphocytes", Journal of Biological Chemistry, Dec. 27, 1996, pp. 33376-33381, vol. 271 No. 52.

Galmiche et al., "Expression of a Functional Single Chain Antibody on the Surface of Extracellular Enveloped Vaccinia Virus as a Step Towards Selective Tumour Cell Targeting", Journal of General Virology, 1997, pp. 3019-3027, vol. 78, Great Britain.

Garbuzova-Davis et al., "Amyotrophic Lateral Sclerosis: A Neurovascular Disease", Brain Research, 2011, pp. 113-125, vol. 1398.

Gauld et al., "B Cell Antigen Receptor Signaling: Roles in Cell Development and Disease", Science, May 2002, pp. 1641-1642, vol. 296, The American Association for the Advancement of Science, United States.

Genova et al., "Ipilimumab (MDX-010) in the Treatment of Non-Small Cell Lung Cancer", Expert Opinion on Biological Therapy, 2012. pp. 939-948, vol. 12 No.7.

Gerber, H.P. and Ferrara, N., "Pharmacology and pharmacodynamics of bevacizumab as monotherapy or in combination with cytotoxic therapy in preclinical studies," Cancer Res 65{3):671-680, American Association for Cancer Research, United tates (2005).

Gilden et al., "Varicella Zoster Virus Vasculopathies: Diverse Clinical Manifestations, Laboratory Features, Pathogenesis, and Treatment", The Lancet Neurology, Aug. 2009, pp. 731-740, vol. 8 No. 8.

Giordano et al., "The Semaphorin 4D Receptor Controls Invasive Growth by Coupling with Met", Nature Cell Biology, Sep. 2002, pp. 720-724, vol. 4 No. 9, Nature Publishing Group, England.

Giraudon et al., "Semaphorin CD100 from Activated T Lymphocytes Induces Process Extension Collapse in Oligodendrocytes and Death of Immature Neural Cells", Journal of Immunology, 2004, pp. 1246-1255, vol. 172 No. 2, The American Association of Immunologists, United States.

Giraudon, P., et al., "T-Cells in Neuronal Injury and Repair," NeuroMolecular Medicine 7:207-216, Humana Press Inc., United States (2005).

Glaser et al., "Dissection of the Combining Site in a Humanized Anti-Tac Antibody", The Journal of Immunology, Oct. 15, 1992, pp. 2607-2614, vol. 149 No 8.

Goldsby et al., "Autoimmunity", Kuby Immunology, 2000, pp. 502-504, vol. 4, W.H. Freeman and Company, United States.

Goldstein, G.W. and Betz, A.L., "The Blood-Brain Barrier," Scientific American 255(3):74-83, New York (1986).

Gonzalez-Velasquez et al., "Soluble aggregates of the amyloid-b protein selectively stimulate permeability in human brain microvascular endothelial monolayers," Journal of Neurochemistry, 2008, pp. 466-477, vol. 107, International Society for Neurochemistry, England.

Gouttefangeas et al., "Differential Proliferative Responses in Subsets of Human CD28+ Cells Delineated by BB27 mAb", International Immunology, Nov. 1993, pp. 423-430, vol. 6 No. 3, Oxford University Press, Oxford.

Gowdie et al., "Primary and Secondary Central Nervous System Vasculitis", Journal of Child Neurology, 2012, pp. 1448-1459, vol. 27 No. 11.

Grosso et al., "CTLA-4 Blockade in Tumor Models: an Overview of Preclinical and Translational Research", Cancer Immunity, Jan. 22, 2013, pp. 5-14, vol. 13.

(56) References Cited

OTHER PUBLICATIONS

Grupp et al., "Chimeric Antigen Receptor-Modified T Cells for Acute Lymphoid Leukemia", New England Journal of Medicine, 2013, pp. 1509-1518, vol. 368.
Guido et al., "Virtual Screening and its Integration with Modern Drug Design Technologies", Current Medicinal Chemistry, 2008, pp. 37-46, vol. 15 No. 1, Bentham Science Publishers Ltd.
Gura, "Systems for Identifying New Drugs are Often Faulty", Science, Nov. 7, 1997, pp. 1041-1042, vol. 278, No. 5340.
Gursoy-Ozdemir et al., "Microvascular Protection is Essential for Successful Neuroprotection in Stroke", Journal of Neurochemistry, 2012, pp. 2-11, vol. 123 Suppl. 2.
Hajj-Ali et al., "Primary Angiitis of the Central Nervous System", Autoimmunity Reviews, 2013, pp. 463-466, vol. 12.
Hall et al., "Human CD100, A Novel Leukocyte Semaphorin That Promotes B-Cell Aggregation and Differentiation", Proceeding of the National Academy of Sciences, Oct. 1996, p. 11780-11785, vol. 93, National Academy of Sciences.
Hawkins et al., "The Blood-Brain Barrier/Neurovascular Unit in Health and Disease," Pharmacological Reviews, 2005, pp. 173-185, vol. 57 No.2, The American Society for Pharmacology and Experimental Therapeutics, United States.
Hebert et al., "The Molecular Dating Game: An Antibody Heavy Chain Hangs Loose with a Chaperone while Waiting for Its Life Partner", Molecular Cell, 2009, pp. 635-636, vol. 34 No. 6, Cell Press, United States.
Herold et al., "CD100 Defines a Newly Identified 150-kDa Human Lymphocyte Surface Structure" T-Cell Antigens Papers, 1994, pp. 50-51, vol. T1.
Herold, C, et al., "Activation signals are delivered through two distinct epitopes of CD100, a unique 150 kDa human lumphocyte surface structure previously defined by BB18 mAb", Int. Immunol. 7(1):1-8, Oxford University Press, England (1994).
Hicklin, D.J. and Ellis, L.M., "Role of the vascular endothelial growth factor pathway in tumor growth and angiogenesis," J. Clin. Oncol. 23(5):1011-1027, American Society of Clinical Oncology, United States (2005).
Higgins et al., "Enhancing Immune Responses to Tumor-Associated Antigens", Cancer Biology and Therapy, 2009, pp. 1440-1449, vol. 8 Issue 15.
Hinson et al., "Neurological Autoimmunity Targeting Aquaporin-4", Neuroscience, 2010, pp. 1009-1018, vol. 168.
Ho, Q.T. and Kuo, C.J., "Vascular endothelial growth factor: biology and therapeutic applications," Int. J. Biochem. Cell Biol. 39(7-8): 1349-1357, Elsevier, Netherlands (2007).
Huber et al., "Signaling At The Growth Cone: Ligand-Receptor Complexes and the Control of Axon Growth and Guidance," Annual Review Neuroscience, pp. 509-563, vol. 26 (2003).
International Preliminary Report on Patentability (Chapter 1) for PCT/US2013/040661 dated Nov. 20, 2014.
International Preliminary Report on Patentability (Chapter I) for PCT/US2012/059757 dated Apr. 24, 2014.
International Preliminary Report on Patentability (Chapter I) for PCT/US2013/034133 dated Oct. 9, 2014.
International Preliminary Report on Patentability for PCT/JP2012/003113 dated Nov. 28, 2013.
International Search Report and Written Opinion for International Application No. PCT/US12/59757, United States Patent Office, United States, mailed on Dec. 18, 2012.
International Search Report and Written Opinion for PCT/JP2012/003113 dated Jul. 10, 2012.
International Search Report and Written Opinion for PCT/US2010/034116 dated Nov. 8, 2010.
International Search Report and Written Opinion for PCT/US2013/034133 dated Jun. 17, 2013.
International Search Report and Written Opinion for PCT/US2013/040661 dated Oct. 8, 2013.
International Search Report and Written Opinion for PCT/US2014/043466 dated Nov. 5, 2014.
International Search Report and Written Opinion for PCT/US2014/060129 dated Jan. 15, 2015.
International Search Report and Written Opinion for PCT/US2014/061592 dated Jan. 21, 2015.
Intlekofer et al., "At the Bench: Preclinical Rationale for CTLA-4 and PD-1 Blockade as Cancer Immunotherapy", Journal of Leukocyte Biology, Jul. 2013, pp. 25-39, vol. 94 No 1.
Ishida, I., et al., "Involvement of CD100, a lymphocyte semaphorin, in the activation of the human immune system via CD72: implications for the regulation of immune and inflammatory responses," International Immunology 15(8) 1027-1034, The Japanese Society for Immunology, Japan (2003).
Ito et al., "Sema4D/Plexin-B1 Activates GSK-3beta Through R-Ras GAP Activity, Inducing Growth Cone Collapse", EMBO Reports, 2006, pp. 704-709, vol. 7 No. 7.
Iwahashi et al., "CDR Substitutions of a Humanized Monoclonal Antibody (CC49): Contributions of Individual CDRs to Antigen Binding and Immunogenicity", Molecular Immunology, 1999, pp. 1079-1091, vol. 36.
Jain, "Barriers to Drug Delivery in Solid Tumors", Scientific American, Jul. 1994, pp. 58-65, vol. 27 No. 1.
Jain, "Molecular regulation of vessel maturation," Nature Medicine, 2003, pp. 685-693, vol. 9, No. 6, Nature Publishing. Company, United States.
Janssen et al., "Structural basis of semaphorin-plexin signaling," Nature, 2010, pp. 1118-1122, vol. 467, Nature Publishing Group, England.
Jenkins et al., "Antigen Presentation by Chemically Modified Splenocytes Induces Antigen-Specific T Cell Unresponsiveness In Vitro and In Vivo", Journal of Experimental Medicine, Feb. 1987, pp. 302-319, vol. 165 No 2.
Kalaria, "The Blood-Brain Barrier and Cerebral Microcirculation in Alzheimer Disease," Cerebrovascular and Brain Metabolism Reviews, 1992, pp. 226-260, vol. 4, Raven Press, Ltd., New York.
Kanai et al., "Anti-Tumor and Anti-Metastatic Effects of Human-Vascular-Endothelial-Growth-Factor-Neutralizing Antibody on Human Colon and Gastric Carcinoma Xenotransplanted Orthotopically into Nude Mice", International Journal of Cancer, 1998, pp. 933-936, vol. 77.
Kato et al., "Semaphorin 4D, a Lymphocyte Semaphorin, Enhances Tumor Cell Motility Through Binding its Receptor, Plexin B1, in Pancreatic Cancer", Cancer Science, 2011, pp. 2029-2037, vol. 102.
Kikutani et al., "Semaphorins in Interactions Between T Cells and Antigen-Presenting Cells", Nature Reviews Immunology, Feb. 2003, pp. 159-167, vol. 3, Nature Publishing Group, United States.
Kim et al., "Inhibition of vascular endothelial growth factor-induced angiogenesis suppresses tumour growth in vivo," Mature, 1993, pp. 841-844, vol. 362, No. 6423, Nature Publishing Group, England.
Kleinschmidt-Demasters et al., "Update on PML and PML-IRIS Occurring in Multiple Sclerosis Patients Treated with Natalizumab", Journal of Neuropathology & Experimental Neurology, Jul. 2012, pp. 604-617, vol. 71 No. 7.
Kornbluth, et al., "Novel Tyrosine Kinase Identified by Phosphotyrosine Antibody Screening of cDNA Libraries," Molecular and Cellular Biology 8(12):5541-5544, American Society for Microbiology, United States (1988).
Kortekaas et al., "Blood-brain barrier dysfunction in parkinsonian midbrain in vivo.", Annals of Neurology, 2005, pp. 176-179, vol. 57, The American Neurological Association, United States.
Kruger, R.P., et al., "Semaphorins Command Cells To Move," Nature Reviews Molecular Cell Biology 6:789-800, Nature Publishing Group, England (2005).
Kumanogoh et al., "Class IV Semaphorin Sema4A Enhances T-Cell Activation and Interacts with Tim-2", Nature, Oct. 2002, pp. 629-633, vol. 419 No. 6907, Nature Publishing Group, England.
Kumanogoh et al., "Identification of CD72 as a Lymphocyte Receptor for the Class IV Semaphorin CD100: A Novel Mechanism for Regulating B Cell Signaling", Immunity, Nov. 2000, pp. 621-631, vol. 13 No. 5, Cell Press, Cambridge, Massachusetts.
Kumanogoh et al., "Requirement for CD100-CD72 Interaction in Fine-Tuning of B-Cell Antigen Receptor Signaling and Homeostatic Maintenance of the B-Cell Compartment", International Immunol-

(56) References Cited

OTHER PUBLICATIONS ogy, 2005, pp. 1277-1282, vol. 17 No. 10, The Japanese Society for Immunology, Oxford University Press, England.

Kumanogoh et al., "Requirement for the Lymphocyte Semaphorin CD100, in the Induction of Antigen-Specific T Dells and the Maturation of Dendritic Cells", Journal of Immunology, Aug. 2002, pp. 1175-1181, The American Association of Immunologists, United States.

Kumanogoh, A. and Kikutani, H., "Immune semaphorins: a new area of semaphorin research," Journal of Cell Science 116:3463-3470, The Company of Biologists Ltd, England (2003).

Kumanogoh, A. and Kikutani, H., "The CD100-CD72 interaction: a novel mechanism of immune regulation," TRENDS in Immunology 22(12):670-676, Elsevier Science Ltd., England (2001).

Lafferty et al., "A New Analysis of Allogeneic Interactions", Australian Journal Experimental Biology and Medical Science, 1975, pp. 27-42, vol. 53 No.1.

Lamminmaki et al., "Crystal Structure of a Recombinant Anti-Estradiol Fab Fragment in Complex with 17B-Estradiol", Journal of Biological Chemistry, 2001, pp. 36687-36694, vol. 276 No. 39.

Lazar, E., et al., "Transforming Growth Factor a: Mutation of Aspartic Acid 47 and Leucine 48 Results in Different Biological Activities," Molecular and Cellular Biology 8(3):1247-1252, American Society for Microbiology, United States (1988).

Levin et al., "Molecular Mimicry to Neurons Results in Neurological Disease", Abstract Viewer and Itinerary Planner, 2002, Program No. 415.3, Society for Neuroscience, Washington DC (Abstract Only).

Li et al., "CD72 Down-Modulates BCR-Induced Signal Transduction and Diminishes Survival in Primary Mature B Lymphocytes", The Journal of Immunology, May 2006, pp. 5321-5328, vol. 176, The American Association of Immunologists, United States.

Li et al., "Modulation of Peripheral B Cell Tolerance by CD72 in a Murine Model", Arthritis and Rheumatism, Oct. 2008, pp. 3192-3904, vol. 58 No. 10, The American College of Rheumatology, United States.

Liddy et al., "Monoclonal TCR-Redirected Tumor Cell Killing", Nature Med. 2012, pp. 980-987, vol. 18.

Lizee et al., "Harnessing the Power of the immune system to target cancer", 2013, Annu rev med pp. 71-90, vol. 64.

Lochhead et al., "Oxidative stress increases blood-brain barrier permeability and induces alterations in occludin luring hypoxia-reoxygenation," Journal of Cerebral Blood Flow & Metabolism, 2010, pp. 1625-1636, vol. 30, Nature Publishing Group, United States.

Love et al., "The ligand-binding face of the semaphorins revealed by the high-resolution crystal structure of SEMA4D," Nature Structural and Molecular Biology, 2003, pp. 843-848, vol. 10, Nature Pub. Co., United States.

Lu et al., "Targeting Metabolic Inflammation in Parkinson's Disease: Implications for Prospective Therapeutic Strategies", Clinical and Experimental Pharmacology and Physiology, 2012, pp. 577-585, vol. 39.

Lyketsos et al., "Neuropsychiatric Symptoms in Alzheimer's Disease", Alzheimer's & Dementia, Sep. 2011, pp. 1-14, vol. 7 No. 5.

Ma et al., "Chemotherapy and Radiotherapy: Cryptic Anticancer Vaccines", Seminars in Immunology, 2010, pp. 113-124, vol. 22 Issue 3.

MacCallum et al.,"Antibody-Antigen Interactions: Contact Analysis and Binding Site Topography", J. Mol. Biol., 1996, pp. 732-745, vol. 262.

Machiels et al., "Cyclophosphamide, Doxorubicin, and Paclitaxel Enhance the Antitumor Immune Response of Granulocyte/Macrophage-Colony Stimulating Factor-secreting Whole-Cell Vaccines in HER-2/neu Tolerized Mice", Cancer Research, 2001, pp. 3689-3697, vol. 61.

Sanchez-Del-Rio et al., "Migraine Aura: New Information on Underlying Mechanisms", Current Opinion in Neurology, 2004, pp. 289-293, vol. 17.

Santaguida et al., "Side by side comparison between dynamic versus static models of blood-brain barrier in vitro: a permeability study," Brain Research, 2006, pp. 1-13, vol. 1109, Elsevier B.V.

Shi et al., "The Class IV Semaphorin CD100 Plays Nonredundant Roles in the Immune System: Defective B and T Dell Activation in CD100-Deficient Mice", Immunity, Nov. 2000, pp. 633-642, vol. 13, Cell Press, United States.

Shihabuddin, "The Search for Neural Progenitor Cells: Prospects for the Therapy of Neurodegenerative Disease," Molecular Medicine Today, vol. 5, No. 1, pp. 474-480 (1999).

Shimada et al., "Isolation of Locally-derived Stem/Progenitor Cells From The Periinfarct Area That Do Not Migrate From The Lateral Ventricle After Cortical Stroke", Stroke, Sep. 2010, pp. e552-e560. vol. 9 Issue 41.

Sica et al., "Macrophage Polarization in Tumor Progression" Seminars in Cancer Biology, 2008, pp. 349-355, vol. 18.

Sierra et al., "Tumor Angiogenesis and Progression are Enhanced by Sema4D Produced by Tumor-Associated Macrophages", Journal of Experimental Medicine, Jul. 2008, pp. 1673-1685, vol. 205 No. 7, The Rockefeller University Press, United States.

Skolnick et al., "From Genes to Protein Structure and Function: Novel Applications of Computational Approaches in the Genomic Era", Trends in Biotechnology, Jan. 2000, pp. 34-39, vol. 18 No. 1, Elsevier Science Ltd., United States.

Slovin et al., "Ipilimumab Alone or in Combination with Radiotherapy in Metastatic Castration-Resistant Prostate Cancer: Results from an Open-Label, Multicenter Phase I/II Study", Annals of Oncology, Mar. 27, 2013, pp. 1813-1821, vol. 24 No. 7.

Small et al., "Immunotherapy of Hormone-Refrectory Prostate Cancer with Antigen-Loaded Dendritic Cells", Journal of Clinical Oncology, 2000, pp. 3894-3903, vol. 18.

Smith et al.,"SEMA4D Compromises Blood-Brain Barrier, Activates Microglia, and Inhibits Remyelination in Neurodegenerative Disease", Neurobiology of Disease, Jan. 2015, pp. 254-268, vol. 73, Elsevier Inc.

Southwell et al., "Anti-semaphorin 4D Immunotherapy Ameliorates Neuropathology and Some Cognitive Impairment in the YAC128 Mouse Model of Huntington Disease", Neurobiology of Disease, pp. 46-56, vol. 76 (2015).

Sporn et al., "Chemoprevention of Cancer", Carcinogenesis, 2000, pp. 525-530, vol. 21 No. 3, Oxford University Press.

Sprinzl et al., "Facing the Dawn of Immunotherapy for Hepatocellular Carcinoma", Journal of Hepatology, 2013, pp. 9-10, vol. 59 No 1.

Srikanth et al., "Neuropsychiatric Symptoms in Dementia-Frequency, Relationship to Dementia Severity and Comparison in Alzheimer's Disease, Vascular Dementia and Frontotemporal Dementia", Journal of Neurological Sciences, Sep. 15, 2005, pp. 43-48, vol. 236 No. 1-2, Elsevier Scientific Publishing Co, Amsterdam, NL.

Stamatovic et al., "Inflammation and brain edema: new insights into the role of chemokines and their receptors," Acta Neurochirurgica, 2006, pp. 444-450, Supplement 96, Springer-Verlag, Austria.

Stancovski et al., "Mechanistic Aspects of the Opposing Effects of Monoclonal Antibodies to the ERBB2 Receptor on Tumor Growth", Proceedings of the National Academy of Science USA, Oct. 1991, pp. 8691-8695, vol. 88.

Steinman, "Multiple Sclerosis: A Two-Stage Disease", Nature Immunology, 2001, pp. 762-764, vol. 2 No. 9.

Suzuki, K., et al., "Semaphorins and their receptors in immune cell interactions," Nature Immunology 9(1):17-23, Nature Publishing Group, England (2008).

Svendsen et al., "Long-Term Survival of Human Central Nervous System Progenitor Cells Transplanted into a Rat Model of Parkinson's Disease," Experimental Neurology, vol. 148, No. 1, pp. 135-146 (1997).

Swiercz et al., "ErbB-2 and Met Reciprocally Regulate Cellular Signaling via Plexin-B1", The Journal of Biological Chemistry, Jan. 2008, pp. 1893-1901, vol. 283 No. 4, The American Society for Biochemistry and Molecular Biology, Inc., United States.

Takeuchi et al., "Angiogenesis in Primary Central Nervous System Lymphoma (PCNSL)", Journal of Neuro-Oncology, 2007, pp. 141-145, vol. 84.

(56) References Cited

OTHER PUBLICATIONS

Tamagnone et al., "Plexins are a Large Family of Receptors for Transmembrane, Secreted, and GPI-Anchored Semaphorins in Vertebrates", Cell, Oct. 1999, pp. 71-80, vol. 99 No. 1, Cell Press, United States.
Tamura et al., "Structural Correlates of an Anticarcinoma Antibody: Identification of Specificity-Determining Residues (SDRs) and Development of a Minimally Immunogenic Antibody Variant by Retention of SDRs Only", The Journal of Immunology, 2000, pp. 1432-1441, vol. 164.
Taniguchi et al, "Sema4D Deficiency Results in an Increase in the Number of Oligodendrocytes in Healthy and Injured Mouse Brains", Journal of Neuroscience Research, 2009, pp. 2833-284, vol. 13, Wiley Interscience, United States.
Topalian et al., "Safety, Activity, and Immune Correlates of Anti-PD-1 Antibody in Cancer", New England Journal of Medicine, Jun. 28, 2012, pp. 2443-2454, vol. 366 No. 26.
Turner et al., "Plexin-lnduced Collapse Assay in COS Cells", Methods in Enzymology, 2006, pp. 665-676, vol. 406, Elsevier Inc., United States.
U.S. Department of Health and Human Services, Food and Drug Administration, Center for Drug Evaluation and Research (CDER), Office of Orphan Products Development (OOPD), "Guidance for Industry—Interpreting Sameness of Monoclonal Antibody Products Under the Orphan Drug Regulations", Apr. 2014, pp. 1-6.
Ulm, Notice of Allowance and Notice of Allowability issued in U.S. Appl. No. 14/519,965 entitled "Use of Semaphorin-4D Binding Molecules for Treating Neurodegenerative Disorders," dated Nov. 9, 2016, 5 pages.
Vajdos et al., "Comprehensive Functional Maps of the Antigenbinding Site of an Anti-ErbB2 Antibody Obtained with Shotgun Scanning Mutagenesis", Journal of Molecular Biology, Jul. 5, 2002, pp. 415-428 at p. 416, vol. 320 No. 2.
Van Nostrand et al., "Enhanced Capillary Amyloid Angiopathy-Associated Pathology in Tg-SwDI Mice With Deleted Nitric Oxide Synthase 2," Stroke, 2010, pp. S135-S138, vol. 41, American Heart Association, Inc., United States.
Vargas et al., "Astrogliosis in Amyotrophic Lateral Sclerosis: Role and Therapeutic Potential of Astrocytes," Neurotherapeutics, pp. 471-481, vol. 7, No. 4 (2010).
Voet et al., Biochemistry, 1990, Sec. 6-3 "Chemical Evolution", pp. 126-128 and Sec. 9-3 "Abnormal Hemoglobins", pp. 228-234, Jon Wiley & Sons, Inc., United States.
Waikar et al., "Imperfect Gold Standards for Kidney Injury Biomarker Evaluation", Journal of the American Society of Nephrology, Jan. 2012, pp. 13-21, vol. 23 No. 1.
Wang, X., et al., "Functional soluble CD100/Sema4D released from activated lymphocytes: possible role in normal and pathologic immune responses," Blood 97:3498-3504, The American Society of Hematology, United States (2001).
Warzocha et al., "Antisense Strategy: Biological Utility and Prospects in the Treatment of Hematological Malignancies", Leukemia and Lymphoma, May 12, 1996, pp. 267-281, vol. 24.
Watanabe et al., "Enhanced Immune Responses in Transgenic Mice Expressing a Truncated Form of the Lymphocyte Semaphorin CD100", The Journal of Immunology, Aug. 2001, pp. 4321-4328, The American Association of Immunologists, United States.
Waubant E., "Biomarkers indicative of blood—brain barrier disruption in multiple sclerosis," Disease Markers 22:235-244, IOS Press (2006).
Westin et al., "Endothelial Proliferation and Increased Blood-Brain Barrier Permeability in the Basal Ganglia in a Rat Model of 3,4-Dihydroxyphenyl-L-Alanine-lnduced Dyskinesia," The Journal of Neuroscience, 2006, pp. 9448-9461, vol. 26, No. 37, Society for Neuroscience, United States.
Whitham et al., "Lymphocytes from SJL/J Mice Immunized with Spinal Cord Respond Selectively to a Peptide of Proteolipid Protein and Transfer Relapsing Demyelinating Experimental Autoimmune Encephalomyelitis", The Journal of Immunology, Jan. 1, 1991, pp. 101-107, vol. 146, No. 1.

Whitton, "Inflammation as a causative factor in the aetiology of Parkinson's disease," British Journal of Pharmacology, 2007, pp. 963-976, vol. 150, Nature Publishing Group, England.
Wilcock et all., "Amyloid reduction by amyloid-b vaccination also reduces mouse tau pathology and protects from neuron loss in two mouse models of Alzheimer's disease," The Journal of Neuroscience, 2009, pp. 7957-7965, vol. 29 No. 25, Society for Neuroscience, United States.
Witherden et al., "The CD100 Receptor Interacts with Its Plexin B2 Ligand to Regulate Epidermal gs T Cell Function," Immunity, 2012, pp. 314-325, vol. 37 No. 2, Cell Press, United States.
Witte et al., "Monoclonal Antibodies Targeting the VEGF Receptor-2 (Flk1/KDR) as an Anti-Angiogenic Therapeutic Strategy", Cancer and Metastasis Reviews, 1998, pp. 155-161, vol. 17.
Wolburg et al., "The Disturbed Blood-Brain Barrier in Human Glioblastoma", Molecular Aspects of Medicine, 2012, pp. 579-589, vol. 33.
Wu et al., "Humanization of a Murine Monoclonal Antibody by Simultaneous Optimization of Framework and CDR Residues", J. Mol. Biol., 1999, pp. 151-162, vol. 294.
Wu, "Simultaneous Humanization and Affinity Optimization of Monoclonal Antibodies", Methods in Molecular Biology, Jan. 2003, pp. 197-212, vol. 207, Humana Press, Inc., New Jersey, United States.
Xiao-Guang et al., "Preparation and Identification of Monoclonal Antibodies Against CD100 Molecule", Chinese Journal of Cellular and Molecular Immunology, Jan. 2003, pp. 80-82, vol. 19 No. 1, Abstract.
Yamaguchi et al., "Sema4D as an Inhibitory Regulator in Oligodendrocyte Development", Molecular and Cellular Neuroscience, Dec. 14, 2011, pp. 290-299, vol. 49.
Yang et al., "Ipilimumab (Anti-CTLA4 Antibody) Causes Regression of Metastatic Renal Cell Cancer Associated with Enteritis and Hypophysitis", Journal for ImmunoTherapy of Cancer, 2007, pp. 825-830, vol. 30 No 8.
Maragakis et al., "Mechanisms of Disease: Astrocytes in Neurodegenerative Disease," Nature Clinical Practice Neurology, pp. 679-698, vol. 2, No. 12 (2006).
Marco et al., "Amyloid b-peptide 1-42 alters tight junction protein distribution and expression in brain microvessel endothelial cells." Neuroscience Letters, 2006, pp. 219-224, vol. 401, Elsevier Ireland Ltd.
Maroso et al., "Toll-Like Receptor 4 and High-Mobility Group Box-1 are Involved in Ictogenesis and can be Targeted to Reduce Seizures", Nature Medicine, Apr. 2010, vol. 16 No 4.
Masterman, "Treatment of the Neuropsychiatric Symptoms in Alzheimer's Disease", Journal of the American Medical Directors Association, Nov. 1, 2003, pp. S146-S154, vol. 4 No 6, Elsevier, NL.
McAllister et al., "Mechanisms of glucose transport at the bloodbrain barrier: and in vitro study," Brain Research, 2001, pp. 20-30, vol. 904, Elsevier Science B.V.
McDermott et al., "PD-1 as a Potential Target in Cancer Therapy", Cancer Medicine, Jun. 3, 2013, pp. 662-673, vol. 2 No 5.
Miller, S.D., et al., "Experimental autoimmune encephalomyelitis in the mouse" Current Protocols in Immunology 15.1.1-15.1.18, John Wiley & Sons, Inc. (2007).
Minagar et al., "Blood-brain barrier disruption in multiple sclerosis," Multiple Sclerosis, 2003, pp. 540-549, vol. 9, Arnold, England.
Mizrahi et al., "CD100 on NK Cells Enhance IFN[gamma] Secretion and Killing of Target Cells Expressing CD72", PLOS One, Jan. 2007, pp. e818, vol. 2 No. 9, New York University School of Medicine, United States.
Mogi et al., "Neurovascular Coupling in Cognitive Impairment Associated with Diabetes Mellitus", Circulation Journal, May 2011, pp. 1042-1048, vol. 75.
Moreau-Fauvarque et al., "The Transmembrane Semaphorin Sema4d/CD100, an Inhibitor of Axonal Growth, Is Expressed on Oligodendrocytes and Upregulated After CNS Lesion", Journal of Neuroscience, 2003, pp. 9229-9239, vol. 27, The Society for Neuroscience, United States.
Negishi-Koga et al., "Suppression of bone formation by osteoclastic expression of semaphorin 4D", Nature Medicine, 2011, p. 1473-1480, vol. 17, No. 11.

(56) References Cited

OTHER PUBLICATIONS

Nelson, "Antibody Fragments", Landes Bioscience, Nov. 27, 2009, pp. 77-83, vol. 2 Issue 1.
Notice of Allowance for U.S. Appl. No. 12/776,187 dated Apr. 1, 2013.
Nuber et al., "Neurodegeneration and Motor Dysfunction in a Conditional Model of Parkinson's Disease", Journal of Neuroscience, Mar. 5, 2008, pp. 2471-2484, vol. 28 No. 10.
Oby et al., "The Blood-Brain Barrier and Epilepsy," Epilepsia, 2006, pp. 1761-1774, vol. 47 No. 11, Blackwell Publishing, Inc., England.
Office Action for U.S. Appl. No. 12/776,187 dated May 18, 2012.
Office Action for U.S. Appl. No. 12/776,187 dated Sep. 14, 2012.
Office Action for U.S. Appl. No. 13/517,807 dated Dec. 26, 2013.
Office Action for U.S. Appl. No. 13/517,807 dated Sep. 16, 2013.
Office Action for U.S. Appl. No. 13/517,807 for Polynucleotides Encoding Anti-CD100 Antibodies or Antigen-Binding Fragments Thereof filed Jun. 14, 2012, dated May 14, 2013.
Office Action for U.S. Appl. No. 13/707,299 dated Jul. 19, 2013.
Office Action for U.S. Appl. No. 13/707,299 dated Nov. 29, 2013.
Office Action for U.S. Appl. No. 13/828,506 dated Aug. 15, 2014.
Office Action for U.S. Appl. No. 13/842,523 dated Jan. 14, 2014.
Office Action for U.S. Appl. No. 13/842,523 dated Oct. 14, 2014.
Office Action for U.S. Appl. No. 14/310,848 dated Jan. 14, 2015.
Oinuma et al., "Semaphorin 4D/Plexin-B1-Mediated R-Ras GAP Activity Inhibits Cell Migration by Regulating beta-1 Integrin Activity", The Journal of Cell Biology, 2006, pp. 601-613, vol. 173 No. 801.
Okuno et al., "Examination of Effect of Sema4D Inhibitition Therapy Against Experimental Autoimmune Encephalomyelitis (EAE) and its Action Mechanism," Department of Immunopathology, Research Institute for Microbia Diseases and Department of Neurology, Osaka University Graduate, School of Medicine, pp. 1094, vol. 50, No. 12 (2010).
Okuno et al., "Roles of Sema4D-Plexin-B1 Interactions in the Central Nervous System for Pathogenesis of Experimental Autoimmune Encephalomyelitis", The Journal of Immunology, Feb. 2010, pp. 1499-1506, vol. 184, The American Association of Immunologists, United States.
Palmer et al., "Progenitor Cells from Human Brain After Death," Nature, vol. 411, No. 6833, pp. 42-43 (2001).
Palmer et al., "The Adult Rat Hippocampus Contains Primordial Neural Stem Cells," Molecular and Cellular Neuroscience, vol. 8, No. 6, pp. 389-404 (1997).
Pander, J., et al., "Pharmacogenetics of EGFR and VEGF inhibition," Drug Discov. Today 12 (23-24):1054-1060, Elsevier Science Ltd., England (2007).
Pardridge, "Receptor-Mediated Peptide Transport Through the Blood-Brain Barrier," Endocrin. Rev. 7:314-330, The Endocrine Society (1986).
Pasterkamp et al., "R-Ras fills another GAP in Semaphorin Signaling," Trends in Cell Biology, 2005, pp. 61-64, vol. 15 No. 2, Elsevier Science Publishers, England.
Pasterkamp, "Getting Neural Circuits into Shape with Semaphorins", Nat Rev Neurosci., 2012, pp. 605-618, vol. 13.
Peranzoni et al., "Positive and Negative Influence of the Matrix Architecture on Antitumor Immune Surveillance", Cellular and Molecular Life Science, May 7, 2013, pp. 4431-4448, vol. 70.
Presta, L.G., et al., "Humanization of an anti-vascular endothelial growth factor monoclonal antibody for the therapy of solid tumors and other disorders," Cancer Res. 57{20):4592-4599, American Associate for Cancer Research, United States (2005).
Qualls et al., "CH10, Tumor Macrophages: Protective and Pathogenic Roles in Cancer Development", Current Topics in Developmental Biology, 2011, pp. 309-328, vol. 94.
Ransohoff et al., "Three or More Routes for Leukocyte Migration Into the Central Nervous System," Nature Reviews Immunology, 2003, pp. 569-581, vol. 3, Nature Publishing Group.
Regev et al., "Semaphorin-4D (Sema-4D), the Plexin-B1 Ligand, is Involved in Mouse Ovary Follicular Development", Reproductive Biology and Endocrinology, 2007, vol. 5 Issue 12, 8 pages.
Riemer et al., "Matching of Trastuzumab (Herceptin) Epitope Mimics Onto the Surface of Her-2/neu—A New Method of Epitope Definition", Molecular Immunology, 2005, pp. 1121-1124, vol. 42.
Risau, "Mechanisms of angiogenesis," Nature, 1997, pp. 671-674, vol. 386, No. 6626, Nature Publishing Group, England.
Roberts et al., "Vaccinia Virus Morphogenesis and Dissemination", Trends in Microbiology, 2008, pp. 472-479, vol. 16 No. 10, Elsevier Trends Journals, England.
Rosenberg et al., "Adoptive Cell Transfer: A Clinical Path to Effective Cancer Immunotherapy" Nature Reviews Cancer 2008, pp. 299-308, vol. 8.
Roth et al., "The Many Faces of Semaphorins: From Development to Pathology", CMLS Cellular and Molecular Life Sciences, Oct. 27, 2008, pp. 649-666, vol. 66 No. 4.
Royal et al., "Phase 2 Trial of Single Agent Ipilimumab (Anti-CTLA-4) for Locally Advanced or Metastatic Pancreatic Adenocarcinoma", Journal of Immunotherapy, Oct. 8, 2010, pp. 828-833, vol. 33 No. 8.
Rudikoff et al., "Single Amino Acid Substitution Altering Antigen-Binding Specificity", Proceedings of the National Academy of Sciences, Mar. 1982, pp. 1979-1983, vol. 79, National Academy of Sciences United States.
Ruffell et al., "Differential Macrophage Programming in the Tumor Microenviroment", Trends in Immunology 2012, pp. 119-126, vol. 33 No 3.
Sagare et al., "Neurovascular Dysfunction and Faulty Amyloid beta-Peptide Clearance in Alzheimer Disease", 2012, Cold Spring Harbor Perspectives in Medicine, pp. a011452, vol. 2.
Clifford et al., "Aβ peptides can enter the brain through a defective blood-brain barrier and bind selectively to neurons" Brain Research 1141 (2007) 223-236.
Aurandt et al., "The semaphorin receptor plexin-B1 signals through a direct interaction with the Rho-specific nucleotide exchange factor, LARG" Proceedings of the National Academy of Sciences Sep. 2002, 99 (19) 12085-12090; DOI 10.1073/pnas.142433199.
Swiercz, Jakub M et al. "Plexin-B1/RhoGEF-mediated RhoA activation involves the receptor tyrosine kinase ErbB-2." The Journal of cell biology vol. 165,6 (2004): 869-80. doi:10.1083/jcb.200312094.
Basile, John R et al. "Plexin-B1 utilizes RhoA and Rho kinase to promote the integrin-dependent activation of Akt and ERK and endothelial cell motility." The Journal of biological chemistry vol. 282,48 (2007): 34888-95. doi:10.1074/jbc.M705467200.
Vikis et al., "The semaphorin receptor plexin-B1 specifically interacts with active Rac in a ligand-dependent manner" PNAS Nov. 7, 2000 97 (23) 12457-12462; https://doi.org/10.1073/pnas.220421797.
Basile, John R et al. "Semaphorin 4D/plexin-B1 induces endothelial cell migration through the activation of PYK2, Src, and the phosphatidylinositol 3-kinase-Akt pathway." Molecular and cellular biology vol. 25,16 (2005): 6889-98. doi:10.1128/MCB.25.16.6889-6898.2005.
Barberis, D., et al., "p190 Rho-GTPase activating protein associates with plexins and it is required for semaphorin signalling", Journal of Cell Science 118:4689-4700 (2005).
Giordano, S., et al., "The Semaphorin 4D receptor controls invasive growth by coupling with Met", Nature Cell Biology 4:720-724 (2002).
Hirotani, M. et al., "Interaction of plexin-B1 with PDZ domain-containing Rho guanine nucleotide exchange factors", Biochemical and Biophysical Research Communications 297(1):32-37 (2002).
Oinuma, I., et al., "Molecular Dissection of the Seamphorin 4D Receptor Plexin-B1-Stimulated R-Ras GTPase-Activating Protein Activity and Neurite Remodeling in Hippocampal Neurons", Jour of Neuroscience 24(50):11473-11480 (2004).
Perrot, V., et al., "Plexin B Regulates Rho through the Guanine Nucleotide Exhange Factors Leukemia-associated RhoGEF (LARG) and PDZ-RhoGEF", The Journal of Biological Chemistry 277(45): 43115-43120 (2002).

(56) References Cited

OTHER PUBLICATIONS

Smith, E.S., et al., "SEMA4D compromises blood-brain barrier, activates microglia, and inhibits remyelination in neurodegenerative disease", Neurobiology of Disease 73:254 268 (2015).

* cited by examiner

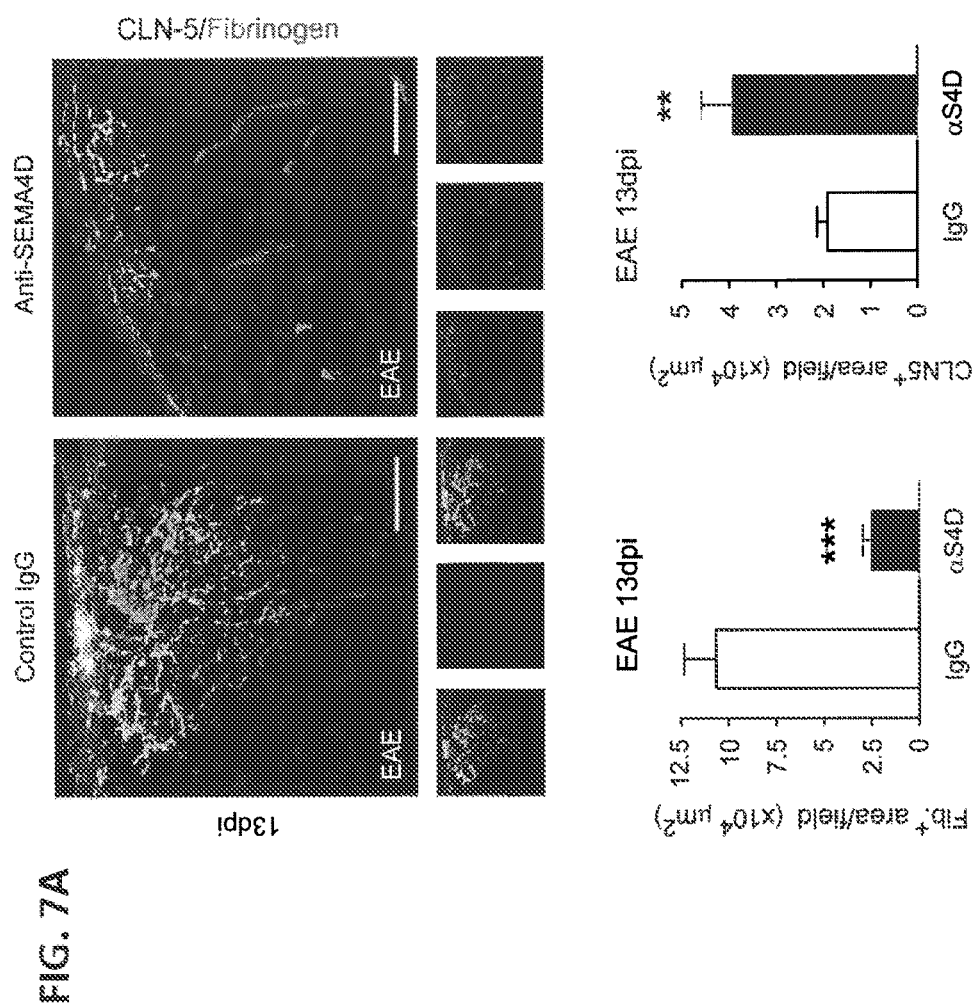

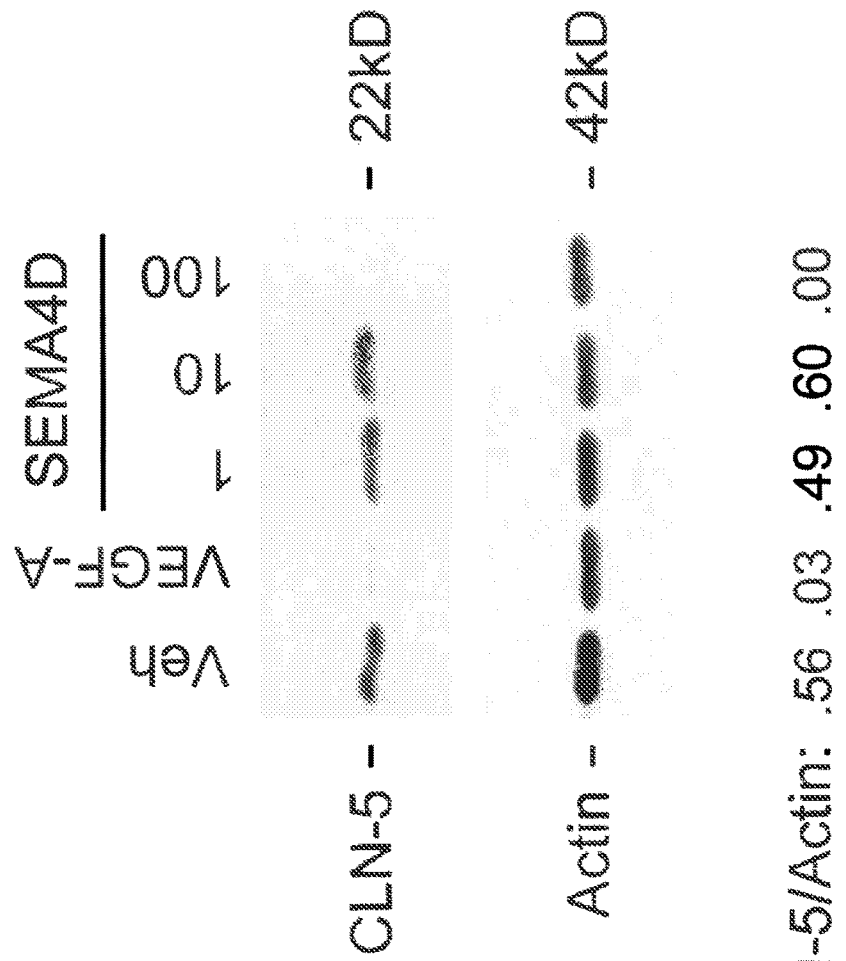

SEQUENCE LISTING

```
<160> NUMBER OF SEQ ID NOS: 40

<210> SEQ ID NO 1
<211> LENGTH: 862
<212> TYPE: PRT
<213> ORGANISM: Homo sapiens

<400> SEQUENCE: 1

Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
        115                 120                 125

Asn Ala Phe Gln Pro Ala Cys Asp His Leu Asn Leu Thr Ser Phe Lys
    130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
```

```
              210                 215                 220
Asp Gly Glu Asp Asp Arg Val Tyr Phe Phe Thr Glu Val Ser Val
225                 230                 235                 240

Glu Tyr Glu Phe Val Phe Arg Val Leu Ile Pro Arg Ile Ala Arg Val
                    245                 250                 255

Cys Lys Gly Asp Gln Gly Gly Leu Arg Thr Leu Gln Lys Lys Trp Thr
                260                 265                 270

Ser Phe Leu Lys Ala Arg Leu Ile Cys Ser Arg Pro Asp Ser Gly Leu
            275                 280                 285

Val Phe Asn Val Leu Arg Asp Val Phe Val Leu Arg Ser Pro Gly Leu
        290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                    325                 330                 335

Phe Ser His Gly Lys Tyr Met Gln Ser Thr Thr Val Glu Gln Ser His
                340                 345                 350

Thr Lys Trp Val Arg Tyr Asn Gly Pro Val Pro Lys Pro Arg Pro Gly
            355                 360                 365

Ala Cys Ile Asp Ser Glu Ala Arg Ala Asn Tyr Thr Ser Ser Leu
        370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                    405                 410                 415

Asp Val Asn Tyr Thr Gln Ile Val Asp Arg Thr Gln Ala Leu Asp
                420                 425                 430

Gly Thr Val Tyr Asp Val Met Phe Val Ser Thr Asp Arg Gly Ala Leu
            435                 440                 445

His Lys Ala Ile Ser Leu Glu His Ala Val His Ile Ile Glu Glu Thr
        450                 455                 460

Gln Leu Phe Gln Asp Phe Glu Pro Val Gln Thr Leu Leu Ser Ser
465                 470                 475                 480

Lys Lys Gly Asn Arg Phe Val Tyr Ala Gly Ser Asn Ser Gly Val Val
                    485                 490                 495

Gln Ala Pro Leu Ala Phe Cys Gly Lys His Gly Thr Cys Glu Asp Cys
                500                 505                 510

Val Leu Ala Arg Asp Pro Tyr Cys Ala Trp Ser Pro Pro Thr Ala Thr
            515                 520                 525

Cys Val Ala Leu His Gln Thr Glu Ser Pro Ser Arg Gly Leu Ile Gln
        530                 535                 540

Glu Met Ser Gly Asp Ala Ser Val Cys Pro Asp Lys Ser Lys Gly Ser
545                 550                 555                 560

Tyr Arg Gln His Phe Phe Lys His Gly Gly Thr Ala Glu Leu Lys Cys
                    565                 570                 575

Ser Gln Lys Ser Asn Leu Ala Arg Val Phe Trp Lys Phe Gln Asn Gly
                580                 585                 590

Val Leu Lys Ala Glu Ser Pro Lys Tyr Gly Leu Met Gly Arg Lys Asn
            595                 600                 605

Leu Leu Ile Phe Asn Leu Ser Glu Gly Asp Ser Gly Val Tyr Gln Cys
        610                 615                 620

Leu Ser Glu Glu Arg Val Lys Asn Lys Thr Val Phe Gln Val Val Ala
625                 630                 635                 640
```

Lys His Val Leu Glu Val Lys Val Pro Lys Pro Val Val Ala Pro
            645                 650                 655

Thr Leu Ser Val Val Gln Thr Glu Gly Ser Arg Ile Ala Thr Lys Val
        660                 665                 670

Leu Val Ala Ser Thr Gln Gly Ser Ser Pro Pro Thr Pro Ala Val Gln
        675                 680                 685

Ala Thr Ser Ser Gly Ala Ile Thr Leu Pro Pro Lys Pro Ala Pro Thr
690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
            725                 730                 735

Met Ser Leu Phe Leu Phe Phe Phe Val Leu Phe Leu Cys Leu Phe Phe
        740                 745                 750

Tyr Asn Cys Tyr Lys Gly Tyr Leu Pro Arg Gln Cys Leu Lys Phe Arg
        755                 760                 765

Ser Ala Leu Leu Ile Gly Lys Lys Pro Lys Ser Asp Phe Cys Asp
        770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
            805                 810                 815

Thr Glu Gln Asp Thr Ile Thr Ser Lys Val Pro Thr Asp Arg Glu Asp
            820                 825                 830

Ser Gln Arg Ile Asp Asp Leu Ser Ala Arg Asp Lys Pro Phe Asp Val
            835                 840                 845

Lys Cys Glu Leu Lys Phe Ala Asp Ser Asp Ala Asp Gly Asp
        850                 855                 860

<210> SEQ ID NO 2
<211> LENGTH: 861
<212> TYPE: PRT
<213> ORGANISM: Murine sp.

<400> SEQUENCE: 2

Met Arg Met Cys Ala Pro Val Arg Gly Leu Phe Leu Ala Leu Val Val
1               5                   10                  15

Val Leu Arg Thr Ala Val Ala Phe Ala Pro Val Pro Arg Leu Thr Trp
            20                  25                  30

Glu His Gly Glu Val Gly Leu Val Gln Phe His Lys Pro Gly Ile Phe
        35                  40                  45

Asn Tyr Ser Ala Leu Leu Met Ser Glu Asp Lys Asp Thr Leu Tyr Val
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ser Lys
            85                  90                  95

Cys Ala Glu Lys Gly Lys Ser Lys Gln Thr Glu Cys Leu Asn Tyr Ile
            100                 105                 110

Arg Val Leu Gln Pro Leu Ser Ser Thr Ser Leu Tyr Val Cys Gly Thr
        115                 120                 125

Asn Ala Phe Gln Pro Thr Cys Asp His Leu Asn Leu Thr Ser Phe Lys
    130                 135                 140

Phe Leu Gly Lys Ser Glu Asp Gly Lys Gly Arg Cys Pro Phe Asp Pro

-continued

```
                145                 150                 155                 160
Ala His Ser Tyr Thr Ser Val Met Val Gly Gly Glu Leu Tyr Ser Gly
                    165                 170                 175

Thr Ser Tyr Asn Phe Leu Gly Ser Glu Pro Ile Ile Ser Arg Asn Ser
                    180                 185                 190

Ser His Ser Pro Leu Arg Thr Glu Tyr Ala Ile Pro Trp Leu Asn Glu
                    195                 200                 205

Pro Ser Phe Val Phe Ala Asp Val Ile Gln Lys Ser Pro Asp Gly Pro
210                 215                 220

Glu Gly Glu Asp Asp Lys Val Tyr Phe Phe Thr Glu Val Ser Val
225                 230                 235                 240

Glu Tyr Glu Phe Val Phe Lys Leu Met Ile Pro Arg Val Ala Arg Val
                    245                 250                 255

Cys Lys Gly Asp Gln Gly Gly Leu Arg Thr Leu Gln Lys Lys Trp Thr
                260                 265                 270

Ser Phe Leu Lys Ala Arg Leu Ile Cys Ser Lys Pro Asp Ser Gly Leu
                275                 280                 285

Val Phe Asn Ile Leu Gln Asp Val Phe Val Leu Arg Ala Pro Gly Leu
                290                 295                 300

Lys Glu Pro Val Phe Tyr Ala Val Phe Thr Pro Gln Leu Asn Asn Val
305                 310                 315                 320

Gly Leu Ser Ala Val Cys Ala Tyr Thr Leu Ala Thr Val Glu Ala Val
                    325                 330                 335

Phe Ser Arg Gly Lys Tyr Met Gln Ser Ala Thr Val Glu Gln Ser His
                340                 345                 350

Thr Lys Trp Val Arg Tyr Asn Gly Pro Val Pro Thr Pro Arg Pro Gly
                355                 360                 365

Ala Cys Ile Asp Ser Glu Ala Arg Ala Ala Asn Tyr Thr Ser Ser Leu
                370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Lys Leu Ile Lys Lys
                    405                 410                 415

Asp Val Asn Tyr Thr Gln Ile Val Val Asp Arg Thr Gln Ala Leu Asp
                420                 425                 430

Gly Thr Phe Tyr Asp Val Met Phe Ile Ser Thr Asp Arg Gly Ala Leu
                435                 440                 445

His Lys Ala Val Ile Leu Thr Lys Glu Val His Val Ile Glu Glu Thr
                450                 455                 460

Gln Leu Phe Arg Asp Ser Glu Pro Val Leu Thr Leu Leu Ser Ser
465                 470                 475                 480

Lys Lys Gly Arg Lys Phe Val Tyr Ala Gly Ser Asn Ser Gly Val Val
                    485                 490                 495

Gln Ala Pro Leu Ala Phe Cys Glu Lys His Gly Ser Cys Glu Asp Cys
                500                 505                 510

Val Leu Ala Arg Asp Pro Tyr Cys Ala Trp Ser Pro Ala Ile Lys Ala
                515                 520                 525

Cys Val Thr Leu His Gln Glu Glu Ala Ser Ser Arg Gly Trp Ile Gln
                530                 535                 540

Asp Met Ser Gly Asp Thr Ser Ser Cys Leu Asp Lys Ser Lys Glu Ser
545                 550                 555                 560

Phe Asn Gln His Phe Phe Lys His Gly Gly Thr Ala Glu Leu Lys Cys
                    565                 570                 575
```

```
Phe Gln Lys Ser Asn Leu Ala Arg Val Val Trp Lys Phe Gln Asn Gly
            580                 585                 590

Glu Leu Lys Ala Ala Ser Pro Lys Tyr Gly Phe Val Gly Arg Lys His
        595                 600                 605

Leu Leu Ile Phe Asn Leu Ser Asp Gly Asp Ser Gly Val Tyr Gln Cys
        610                 615                 620

Leu Ser Glu Glu Arg Val Arg Asn Lys Thr Val Ser Gln Leu Leu Ala
625                 630                 635                 640

Lys His Val Leu Glu Val Lys Met Val Pro Arg Thr Pro Pro Ser Pro
                645                 650                 655

Thr Ser Glu Asp Ala Gln Thr Glu Gly Ser Lys Ile Thr Ser Lys Met
            660                 665                 670

Pro Val Ala Ser Thr Gln Gly Ser Ser Pro Pro Thr Pro Ala Leu Trp
        675                 680                 685

Ala Thr Ser Pro Arg Ala Ala Thr Leu Pro Pro Lys Ser Ser Ser Gly
        690                 695                 700

Thr Ser Cys Glu Pro Lys Met Val Ile Asn Thr Val Pro Gln Leu His
705                 710                 715                 720

Ser Glu Lys Thr Val Tyr Leu Lys Ser Ser Asp Asn Arg Leu Leu Met
                725                 730                 735

Ser Leu Leu Leu Phe Ile Phe Val Leu Phe Leu Cys Leu Phe Ser Tyr
            740                 745                 750

Asn Cys Tyr Lys Gly Tyr Leu Pro Gly Gln Cys Leu Lys Phe Arg Ser
        755                 760                 765

Ala Leu Leu Leu Gly Lys Lys Thr Pro Lys Ser Asp Phe Ser Asp Leu
        770                 775                 780

Glu Gln Ser Val Lys Glu Thr Leu Val Glu Pro Gly Ser Phe Ser Gln
785                 790                 795                 800

Gln Asn Gly Asp His Pro Lys Pro Ala Leu Asp Thr Gly Tyr Glu Thr
                805                 810                 815

Glu Gln Asp Thr Ile Thr Ser Lys Val Pro Thr Asp Arg Glu Asp Ser
            820                 825                 830

Gln Arg Ile Asp Glu Leu Ser Ala Arg Asp Lys Pro Phe Asp Val Lys
        835                 840                 845

Cys Glu Leu Lys Phe Ala Asp Ser Asp Ala Asp Gly Asp
850                 855                 860

<210> SEQ ID NO 3
<211> LENGTH: 30
<212> TYPE: DNA
<213> ORGANISM: Artificial
<220> FEATURE:
<223> OTHER INFORMATION: Polynucleotide anti-CD100 VH CDR1

<400> SEQUENCE: 3
ggctacagct tcagcgacta ctacatgcac                                    30

<210> SEQ ID NO 4
<211> LENGTH: 51
<212> TYPE: DNA
<213> ORGANISM: Artificial
<220> FEATURE:
<223> OTHER INFORMATION: Polynucleotide anti-CD100 VH CDR2

<400> SEQUENCE: 4
cagattaatc ctaccactgg cggcgctagc tacaaccaga agttcaaggg c             51
```

<210> SEQ ID NO 5
<211> LENGTH: 27
<212> TYPE: DNA
<213> ORGANISM: Artificial
<220> FEATURE:
<223> OTHER INFORMATION: Polynucleotide anti-CD100 VH CDR3

<400> SEQUENCE: 5
tattactacg gcagacactt cgatgtc                                         27

<210> SEQ ID NO 6
<211> LENGTH: 10
<212> TYPE: PRT
<213> ORGANISM: Artificial
<220> FEATURE:
<223> OTHER INFORMATION: Polypeptide anti-CD100 VH CDR1

<400> SEQUENCE: 6

Gly Tyr Ser Phe Ser Asp Tyr Tyr Met His
1               5                   10

<210> SEQ ID NO 7
<211> LENGTH: 17
<212> TYPE: PRT
<213> ORGANISM: Artificial
<220> FEATURE:
<223> OTHER INFORMATION: Polypeptide anti-CD100 VH CDR2

<400> SEQUENCE: 7

Gln Ile Asn Pro Thr Thr Gly Gly Ala Ser Tyr Asn Gln Lys Phe Lys
1               5                   10                  15

Gly

<210> SEQ ID NO 8
<211> LENGTH: 9
<212> TYPE: PRT
<213> ORGANISM: Artificial
<220> FEATURE:
<223> OTHER INFORMATION: Polypeptide anti-CD100 VH CDR3

<400> SEQUENCE: 8

Tyr Tyr Tyr Gly Arg His Phe Asp Val
1               5

<210> SEQ ID NO 9
<211> LENGTH: 118
<212> TYPE: PRT
<213> ORGANISM: Artificial
<220> FEATURE:
<223> OTHER INFORMATION: Polypeptide anti-CD100 VH 2503

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Ser Asp Tyr
            20                  25                  30

Tyr Met His Trp Val Arg Gln Ala Pro Gly Gln Gly Leu Glu Trp Met
        35                  40                  45

Gly Gln Ile Asn Pro Thr Thr Gly Gly Ala Ser Tyr Asn Gln Lys Phe
    50                  55                  60

Lys Gly Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys

```
                    85                  90                  95
Ala Arg Tyr Tyr Tyr Gly Arg His Phe Asp Val Trp Gly Gln Gly Thr
            100                 105                 110

Thr Val Thr Val Ser Ser
        115

<210> SEQ ID NO 10
<211> LENGTH: 118
<212> TYPE: PRT
<213> ORGANISM: Artificial
<220> FEATURE:
<223> OTHER INFORMATION: Polypeptide anti-CD100 VH 67

<400> SEQUENCE: 10

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
            20                  25                  30

Tyr Met His Trp Val Lys Gln Ser Pro Glu Asn Ser Leu Glu Trp Ile
        35                  40                  45

Gly Gln Ile Asn Pro Thr Thr Gly Gly Ala Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Tyr Tyr Tyr Gly Arg His Phe Asp Val Trp Gly Gln Gly Thr
            100                 105                 110

Thr Val Thr Val Ser Ser
        115

<210> SEQ ID NO 11
<211> LENGTH: 45
<212> TYPE: DNA
<213> ORGANISM: Artificial
<220> FEATURE:
<223> OTHER INFORMATION: Polynucleotide anti-CD100 VL CDR1

<400> SEQUENCE: 11
aaggccagcc aaagcgtgga ttatgatggc gatagctata tgaac          45

<210> SEQ ID NO 12
<211> LENGTH: 21
<212> TYPE: DNA
<213> ORGANISM: Artificial
<220> FEATURE:
<223> OTHER INFORMATION: Polynucleotide anti-CD100 VL CDR2

<400> SEQUENCE: 12
gctgcatcca atctggaaag c                                    21

<210> SEQ ID NO 13
<211> LENGTH: 27
<212> TYPE: DNA
<213> ORGANISM: Artificial
<220> FEATURE:
<223> OTHER INFORMATION: Polynucleotide anti-CD100 VL CDR3

<400> SEQUENCE: 13
cagcaaagca atgaggatcc ctacacc                              27
```

```
<210> SEQ ID NO 14
<211> LENGTH: 15
<212> TYPE: PRT
<213> ORGANISM: Artificial
<220> FEATURE:
<223> OTHER INFORMATION: Polypeptide anti-CD100 VL CDR1

<400> SEQUENCE: 14

Lys Ala Ser Gln Ser Val Asp Tyr Asp Gly Asp Ser Tyr Met Asn
1               5                   10                  15

<210> SEQ ID NO 15
<211> LENGTH: 7
<212> TYPE: PRT
<213> ORGANISM: Artificial
<220> FEATURE:
<223> OTHER INFORMATION: Polypeptide anti-CD100 VL CDR2

<400> SEQUENCE: 15

Ala Ala Ser Asn Leu Glu Ser
1               5

<210> SEQ ID NO 16
<211> LENGTH: 9
<212> TYPE: PRT
<213> ORGANISM: Artificial
<220> FEATURE:
<223> OTHER INFORMATION: Polypeptide anti-CD100 VL CDR3

<400> SEQUENCE: 16

Gln Gln Ser Asn Glu Asp Pro Tyr Thr
1               5

<210> SEQ ID NO 17
<211> LENGTH: 111
<212> TYPE: PRT
<213> ORGANISM: Artificial
<220> FEATURE:
<223> OTHER INFORMATION: Polypeptide anti-CD100 VL 2503

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 18
<211> LENGTH: 111
<212> TYPE: PRT
<213> ORGANISM: Artificial
<220> FEATURE:
<223> OTHER INFORMATION: Polypeptide anti-CD100 VL 67

<400> SEQUENCE: 18
```

```
Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110
```

<210> SEQ ID NO 19
<211> LENGTH: 354
<212> TYPE: DNA
<213> ORGANISM: Artificial
<220> FEATURE:
<223> OTHER INFORMATION: Polynucleotide anti-CD100 VH 2503

<400> SEQUENCE: 19

```
caggtgcagc tggtgcagag cggcgctgag gtgaagaagc ctggcagcag cgtgaaggtc    60
tcctgcaagg ctagcggcta cagcttcagc gactactaca tgcactgggt gagacaggcc   120
cctggccaag gcctggagtg gatgggccag attaatccta ccactggcgg cgctagctac   180
aaccagaagt tcaagggcaa ggccaccatt accgtggaca aaagcaccag cacagcctac   240
atggagctga gcagcctgag aagcgaggac accgccgtgt attactgtgc cagatattac   300
tacggcagac acttcgatgt ctggggccaa ggcaccacgg tcaccgtctc ttca          354
```

<210> SEQ ID NO 20
<211> LENGTH: 354
<212> TYPE: DNA
<213> ORGANISM: Artificial
<220> FEATURE:
<223> OTHER INFORMATION: Polynucleotide anti-CD100 VH 67

<400> SEQUENCE: 20

```
caggtccagc tgcagcagtc tggacctgag ctggtgaagc ctggggcttc agtgaagata    60
tcctgcaagg cttctggtta ctcattcagt gactactaca tgcactgggt gaagcaaagt   120
cctgaaaata gtcttgagtg gattggacag attaatccta ccactggggg tgctagctac   180
aaccagaagt tcaagggcaa ggccacatta actgtagata atcctccag cacagcctac    240 atgcagctca agagcctgac atctgaagag tctgcagtct attactgtac aagatattac   300
tacggtagac acttcgatgt ctggggccaa gggaccacgg tcaccgtttc ctca          354
```

<210> SEQ ID NO 21
<211> LENGTH: 333
<212> TYPE: DNA
<213> ORGANISM: Artificial
<220> FEATURE:
<223> OTHER INFORMATION: Polynucleotide anti-CD100 VL 2503

<400> SEQUENCE: 21

```
gacatcgtga tgacccagag cccagacagc ctggctgtga gcctgggcga gagggccacc    60
atcaactgca aggccagcca aagcgtggat tatgatggcg atagctatat gaactggtac   120
```
cagcagaaac caggccagcc tcctaagctg ctgatttacg ctgcatccaa tctggaaagc    180
ggcgtgcctg acagattcag cggcagcggc agcggcacag atttcactct gaccatcagc    240
agcctgcagg ctgaagatgt ggcagtgtat tactgtcagc aaagcaatga ggatccctac    300
accttcggcc aagggaccaa gctcgagatc aaa                                 333

<210> SEQ ID NO 22
<211> LENGTH: 333
<212> TYPE: DNA
<213> ORGANISM: Artificial
<220> FEATURE:
<223> OTHER INFORMATION: Polynucleotide anti-CD100 VL 67

<400> SEQUENCE: 22
gacattgtga tgacccagtc tccagcttct ttggctgtgt ctctagggca gagggccacc     60
atctcctgca aggccagcca agtgttgat tatgatggtg atagttatat gaactggtac    120
caacagaaac caggacagcc acccaaactc ctcatctatg ctgcatccaa tctagaatct    180
gggatcccag ccaggtttag tggcagtggg tctgggacag acttcaccct caacatccat    240
cctgtggagg aggaggatgc tgcaacctat tactgtcagc aaagtaatga ggatccgtac    300
acgttcggag gggggaccaa gctcgagatc aaa                                 333

<210> SEQ ID NO 23
<211> LENGTH: 2586
<212> TYPE: DNA
<213> ORGANISM: Homo sapiens

<400> SEQUENCE: 23
atgaggatgt gcacccccat taggggctg ctcatggccc ttgcagtgat gtttgggaca      60
gcgatggcat ttgcacccat accccggatc acctgggagc acagagaggt gcacctggtg    120
cagtttcatg agccagacat ctacaactac tcagccttgc tgctgagcga ggacaaggac    180
accttgtaca taggtgcccg ggaggcggtc ttcgctgtga cgcactcaa catctccgag     240 aagcagcatg aggtgtattg gaaggtctca gaagacaaaa agcaaaatg tgcagaaaag    300 gggaaatcaa aacagacaga gtgcctcaac tacatccggg tgctgcagcc actcagcgcc    360
acttcccttt acgtgtgtgg gaccaacgca ttccagccgg cctgtgacca cctgaactta    420
acatccttta gtttctggg gaaaaatgaa gatggcaaag aagatgtcc ctttgaccca     480 gcacacagct acacatccgt catggttgat ggagaacttt attcggggac gtcgtataat    540
tttttgggaa gtgaaccat catctcccga aattcttccc acagtcctct gaggacagaa    600
tatgcaatcc cttggctgaa cgagcctagt ttcgtgtttg ctgacgtgat ccgaaaaagc    660
ccagacagcc ccgacggcga ggatgacagg gtctacttct cttcacgga ggtgtctgtg    720 gagtatgagt ttgtgttcag ggtgctgatc ccacggatag caagagtgtg caagggggac    780
cagggcggcc tgaggacctt gcagaagaaa tggacctcct tcctgaaagc ccgactcatc    840
tgctcccggc cagacagcgg cttggtcttc aatgtgctgc gggatgtctt cgtgctcagg    900
tccccgggcc tgaaggtgcc tgtgttctat gcactcttca cccacagct gaacaacgtg    960 gggctgtcgg cagtgcgc ctacaacctg tccacagccg aggaggtctt ctcccacggg   1020
aagtacatgc agagcaccac agtggagcag tcccacacca gtgggtgcg ctataatgcc   1080 ccggtaccca gccgcggcc tgagcgtgc atcgacagcg aggcacgggc cgccaactac   1140
accagctcct tgaatttgcc agacaagacg ctgcagttcg ttaaagacca ccctttgatg   1200
gatgactcgg taaccccaat agacaacagg cccaggttaa tcaagaaaga tgtgaactac   1260

```
acccagatcg tggtggaccg gacccaggcc ctggatggga ctgtctatga tgtcatgttt    1320
gtcagcacag accggggagc tctgcacaaa gccatcagcc tcgagcacgc tgttcacatc    1380
atcgaggaga cccagctctt ccaggacttt gagccagtcc agaccctgct gctgtcttca    1440
aagaagggca acaggtttgt ctatgctggc tctaactcgg gcgtggtcca ggccccgctg    1500
gccttctgtg ggaagcacgg cacctgcgag gactgtgtgc tggcgcggga cccctactgc    1560
gcctggagcc cgcccacagc gacctgcgtg gctctgcacc agaccgagag ccccagcagg    1620
ggtttgattc aggagatgag cggcgatgct tctgtgtgcc cggataaaag taaaggaagt    1680
taccggcagc atttttttcaa gcacggtggc acagcggaac tgaaatgctc ccaaaaatcc    1740
aacctggccc gggtcttttg aagttccag aatggcgtgt tgaaggccga gagccccaag    1800
tacggtctta tgggcagaaa aaacttgctc atcttcaact tgtcagaagg agacagtggg    1860
gtgtaccagt gcctgtcaga ggagagggtt aagaacaaaa cggtcttcca agtggtcgcc    1920
aagcacgtcc tggaagtgaa ggtggttcca agcccgtag tggcccccac cttgtcagtt    1980
gttcagacag aaggtagtag gattgccacc aaagtgttgg tggcatccac ccaagggtct    2040
tctcccccaa ccccagccgt gcaggccacc tcctccgggg ccatcaccct tcctcccaag    2100
cctgcgccca ccggcacatc ctgcgaacca agatcgtca tcaacacggt ccccagctc    2160 cactcggaga aaaccatgta tcttaagtcc agcgacaacc gcctcctcat gtccctcttc    2220
ctcttcttct ttgttctctt cctctgcctc tttttctaca actgctataa gggatacctg    2280
cccagacagt gcttgaaatt ccgctcggcc ctactaattg ggaagaagaa gcccaagtca    2340
gatttctgtg accgtgagca gagcctgaag gagacgttag tagagccagg gagcttctcc    2400
cagcagaatg gggagcaccc caagccagcc ctggacaccg gctatgagac cgagcaagac    2460
accatcacca gcaaagtccc cacggatagg gaggactcac agaggatcga cgacctttct    2520
gccagggaca agcccttga cgtcaagtgt gagctgaagt tcgctgactc agacgcagat    2580
ggagac                                                              2586
```

<210> SEQ ID NO 24
<211> LENGTH: 13
<212> TYPE: PRT
<213> ORGANISM: Artificial
<220> FEATURE:
<223> OTHER INFORMATION: Peptide epitope of proteolipid protein
      PLP(139-151)

<400> SEQUENCE: 24

His Ser Leu Gly Lys Trp Leu Gly His Pro Asp Lys Phe
1               5                   10

<210> SEQ ID NO 25
<211> LENGTH: 118
<212> TYPE: PRT
<213> ORGANISM: Artificial
<220> FEATURE:
<223> OTHER INFORMATION: Polypeptide anti-CD100 VH 76

<400> SEQUENCE: 25

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile
        35                  40                  45

```
Gly Tyr Ile Asn Pro Ser Thr Gly Tyr Ser Asp Tyr Asn Gln Lys Phe
            50                  55                  60

Lys Asp Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Asp Pro Tyr Gly Trp Thr Met Asp Ser Trp Gly Gln Gly Thr
                100                 105                 110

Leu Val Thr Val Ser Ser
            115

<210> SEQ ID NO 26
<211> LENGTH: 10
<212> TYPE: PRT
<213> ORGANISM: Artificial
<220> FEATURE:
<223> OTHER INFORMATION: Polypeptide anti-CD100 VH 76 CDR1

<400> SEQUENCE: 26

Gly Tyr Thr Phe Thr Arg Tyr Trp Met His
1               5                   10

<210> SEQ ID NO 27
<211> LENGTH: 17
<212> TYPE: PRT
<213> ORGANISM: Artificial
<220> FEATURE:
<223> OTHER INFORMATION: Polypeptide anti-CD100 VH 76 CDR2

<400> SEQUENCE: 27

Tyr Ile Asn Pro Ser Thr Gly Tyr Ser Asp Tyr Asn Gln Lys Phe Lys
1               5                   10                  15

Asp

<210> SEQ ID NO 28
<211> LENGTH: 9
<212> TYPE: PRT
<213> ORGANISM: Artificial
<220> FEATURE:
<223> OTHER INFORMATION: Polypeptide anti-CD100 VH 76 CDR3

<400> SEQUENCE: 28

Asp Pro Tyr Gly Trp Thr Met Asp Ser
1               5

<210> SEQ ID NO 29
<211> LENGTH: 107
<212> TYPE: PRT
<213> ORGANISM: Artificial
<220> FEATURE:
<223> OTHER INFORMATION: Polypeptide anti-CD100 VL 76

<400> SEQUENCE: 29

Asp Ile Gln Met Thr Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
                20                  25                  30

Leu Ser Trp Tyr Gln Gln Lys Pro Gly Asn Ile Pro Lys Leu Leu Ile
            35                  40                  45

Tyr Lys Ala Ser Asn Leu His Thr Gly Val Pro Ser Arg Phe Ser Gly
    50                  55                  60
```

```
Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys
            100                 105
```

<210> SEQ ID NO 30
<211> LENGTH: 11
<212> TYPE: PRT
<213> ORGANISM: Artificial
<220> FEATURE:
<223> OTHER INFORMATION: Polypeptide anti-CD100 VL 76 CDR1

<400> SEQUENCE: 30

```
His Ala Ser Gln Asn Ile Asn Val Trp Leu Ser
 1               5                  10
```

<210> SEQ ID NO 31
<211> LENGTH: 7
<212> TYPE: PRT
<213> ORGANISM: Artificial
<220> FEATURE:
<223> OTHER INFORMATION: Polypeptide anti-CD100 VL 76 CDR2

<400> SEQUENCE: 31

```
Lys Ala Ser Asn Leu His Thr
 1               5
```

<210> SEQ ID NO 32
<211> LENGTH: 9
<212> TYPE: PRT
<213> ORGANISM: Artificial
<220> FEATURE:
<223> OTHER INFORMATION: Polypeptide anti-CD100 VL 76 CDR3

<400> SEQUENCE: 32

```
Gln Gln Gly Gln Ser Tyr Pro Tyr Thr
 1               5
```

<210> SEQ ID NO 33
<211> LENGTH: 354
<212> TYPE: DNA
<213> ORGANISM: Artificial
<220> FEATURE:
<223> OTHER INFORMATION: Polynucleotide anti-CD100 VH 76

<400> SEQUENCE: 33

```
caggtccagc tgcagcagtc tggggctgaa ctggcaaaac ctggggcctc agtgaagatg    60
tcctgcaagg cttctggcta cacctttact aggtactgga tgcactgggt aaaacagagg   120
cctggacagg gtctggaatg gattggatac attaatccta gcactggtta ttctgattac   180
aatcagaagt tcaaggacaa ggccacattg actgcagaca atcctccag cacagcctac   240 atgcaactga gcagcctgac atctgaggac tctgcagtct attactgtgc aagagacccc   300
tacggctgga ctatggactc ctggggccaa gggactctgg tcaccgtctc ctca         354
```

<210> SEQ ID NO 34
<211> LENGTH: 30
<212> TYPE: DNA
<213> ORGANISM: Artificial
<220> FEATURE:
<223> OTHER INFORMATION: Polynucleotide anti-CD100 VH 76 CDR1

<400> SEQUENCE: 34

```
ggctacacct ttactaggta ctggatgcac                                      30

<210> SEQ ID NO 35
<211> LENGTH: 51
<212> TYPE: DNA
<213> ORGANISM: Artificial
<220> FEATURE:
<223> OTHER INFORMATION: Polynucleotide anti-CD100 VH 76 CDR2

<400> SEQUENCE: 35
tacattaatc ctagcactgg ttattctgat tacaatcaga agttcaagga c              51

<210> SEQ ID NO 36
<211> LENGTH: 27
<212> TYPE: DNA
<213> ORGANISM: Artificial
<220> FEATURE:
<223> OTHER INFORMATION: Polynucleotide anti-CD100 VH 76 CDR3

<400> SEQUENCE: 36
gacccctacg gctggactat ggactcc                                         27

<210> SEQ ID NO 37
<211> LENGTH: 321
<212> TYPE: DNA
<213> ORGANISM: Artificial
<220> FEATURE:
<223> OTHER INFORMATION: Polynucleotide anti-CD100 VL 76

<400> SEQUENCE: 37
gacatccaga tgacccagtc tccatccagt ctgtctgcat cccttggaga cacaattacc     60
atcacttgcc atgccagtca gaacattaat gtttggttaa gctggtacca gcagaaacca    120
ggaaatattc ctaaactatt gatctataag gcttccaact tgcacacagg cgtcccatca    180
aggtttagtg gcagtggatc tggaacaggt ttcacattaa ccatcagcag cctgcagcct    240
gaagacattg ccacttacta ctgtcaacag ggtcaaagtt atccgtacac gttcggaggg    300
gggaccaagc tcgagatcaa a                                              321

<210> SEQ ID NO 38
<211> LENGTH: 33
<212> TYPE: DNA
<213> ORGANISM: Artificial
<220> FEATURE:
<223> OTHER INFORMATION: Polynucleotide anti-CD100 VL 76 CDR1

<400> SEQUENCE: 38
catgccagtc agaacattaa tgtttggtta agc                                  33

<210> SEQ ID NO 39
<211> LENGTH: 21
<212> TYPE: DNA
<213> ORGANISM: Artificial
<220> FEATURE:
<223> OTHER INFORMATION: Polynucleotide anti-CD100 VL 76 CDR2
```

```
<400> SEQUENCE: 39
aaggcttcca acttgcacac a                                      21

<210> SEQ ID NO 40
<211> LENGTH: 27
<212> TYPE: DNA
<213> ORGANISM: Artificial
<220> FEATURE:
<223> OTHER INFORMATION: Polynucleotide anti-CD100 VL 76 CDR3

<400> SEQUENCE: 40
caacagggtc aaagttatcc gtacacg                                27
```

USE OF SEMAPHORIN-4D BINDING MOLECULES FOR MODULATION OF BLOOD BRAIN BARRIER PERMEABILITY

CROSS-REFERENCE TO RELATED APPLICATIONS

This application is a continuation of currently pending U.S. application Ser. No. 13/649,651, filed Oct. 11, 2012, which claims priority benefit to U.S. Provisional Appl. No. 61/545,809, filed on Oct. 11, 2011, U.S. Provisional Appl. No. 61/555,726, filed on Nov. 4, 2011, and U.S. Provisional Appl. No. 61/593,641, filed on Feb. 1, 2012, the contents of which are hereby incorporated by reference in their entireties.

REFERENCE TO SEQUENCE LISTING SUBMITTED ELECTRONICALLY

The content of the electronically submitted sequence listing in ASCII text file (Name: "09790-002US2-Sequence-Listing"; Size: 33,807 bytes; and Date of Creation: Jun. 3, 2019) filed with the application is incorporated herein by reference in its entirety.

BACKGROUND OF THE INVENTION

Semaphorin 4D (SEMA4D), also known as CD100, is a transmembrane protein (e.g., SEQ ID NO: 1 (human); SEQ ID NO: 2 (murine)) that belongs to the semaphorin gene family. SEMA4D is expressed on the cell surface as a homodimer, but upon cell activation SEMA4D can be released from the cell surface via proteolytic cleavage to generate sSEMA4D, a soluble form of the protein, which is also biologically active. See Suzuki et al., *Nature Rev. Immunol.* 3:159-167 (2003); Kikutani et al., *Nature Immunol.* 9:17-23 (2008).

SEMA4D is expressed at high levels in lymphoid organs, including the spleen, thymus, and lymph nodes, and in non-lymphoid organs, such as the brain, heart, and kidney. In lymphoid organs, SEMA4D is abundantly expressed on resting T cells but only weakly expressed on resting B cells and antigen-presenting cells (APCs), such as dendritic cells (DCs). Its expression, however, is upregulated in these cells following activation by various immunological stimuli. The release of soluble SEMA4D from immune cells is also increased by cell activation.

SEMA4D has been implicated in the development of neurodegenerative diseases, autoimmune diseases, demyelinating diseases, and certain cancers. While the role of SEMA4D signaling through its receptors, e.g., Plexin-B1, on angiogenesis is well-recognized, the effect of SEMA4D signaling on Blood Brain Barrier (BBB) remains unclear. This is important because changes in the permeability of the BBB have a profound influence on brain tissue and function. There remains, therefore, a need for treatments for neuroinflammatory disorders that arise as a result of breakdown in the BBB, and, in particular, therapeutics that inhibit, suppress, prevent, reverse, or slow the breakdown of the BBB.

BRIEF SUMMARY OF THE INVENTION

Methods for using semaphorin-4d binding molecules for modulation of blood brain barrier permeability are disclosed herein. Evidence is presented demonstrating that SEAM4D can compromise the integrity of the BBB thereby increasing its permeability. According to aspects of the invention illustrated herein, there is provided a method for decreasing blood brain barrier permeability in a subject having a neuroinflammatory disorder including administering to the subject an effective amount of an isolated binding molecule which specifically binds to semaphorin-4D (SEMA4D), thereby decreasing blood brain barrier permeability in the subject.

According to aspects illustrated herein, there is provided a method of maintaining or increasing Claudin-5 expression in a subject having a neuroinflammatory disorder comprising administering to the subject an effective amount of an isolated binding molecule which specifically binds to semaphorin-4D (SEMA4D), wherein the binding molecule maintains or increases Claudin-5 expression in the subject.

According to aspects illustrated herein, there is provided a method of decreasing blood brain barrier permeability in a subject having a neuroinflammatory disorder, comprising administering to the subject an effective amount of an isolated binding molecule which specifically inhibits semaphorin 4D (SEMA4D) interaction with a SEMA4D receptor thereby decreasing blood brain barrier permeability in the subject.

According to aspects illustrated herein, there is provided a method of treating a subject having a neuroinflammatory disorder, comprising administering to the subject an effective amount of an isolated binding molecule which specifically inhibits semaphorin 4D (SEMA4D) interaction with a SEMA4D receptor, wherein the binding molecule decreases permeability of the blood-brain barrier, thereby treating the subject.

According to aspects illustrated herein, there is provided a method of decreasing blood-brain barrier permeability in a subject having a neuroinflammatory disorder, comprising administering to the subject an effective amount of an isolated binding molecule which specifically binds to SEMA4D, wherein the binding molecule competitively inhibits a reference monoclonal antibody selected from the group consisting of VX15/2503 or 67 from specifically binding to SEMA4D.

According to aspects illustrated herein, there is provided a method of treating a subject having a neuroinflammatory disorder, comprising administering to the subject an effective amount of an isolated binding molecule which specifically binds to semaphorin-4D (SEMA4D) and an isolated binding molecule which specifically binds to Plexin-B1, wherein the SEMA4D and Plexin-B1 binding molecules decrease permeability of the blood-brain barrier, thereby treating the subject.

According to aspects illustrated herein, there is provided a method of treating a subject having a neuroinflammatory disorder, comprising administering to the subject an effective amount of an inhibitor of semaphorin 4D (SEMA4D) interaction with a SEMA4D receptor, wherein the inhibitor decreases permeability of the blood-brain barrier, thereby treating the subject.

BRIEF DESCRIPTION OF THE DRAWINGS/FIGURES

FIG. 1: Schematic of the dynamic in vitro BBB ("DIV-BBB") experimental protocol described in the Examples.

Figure 2:
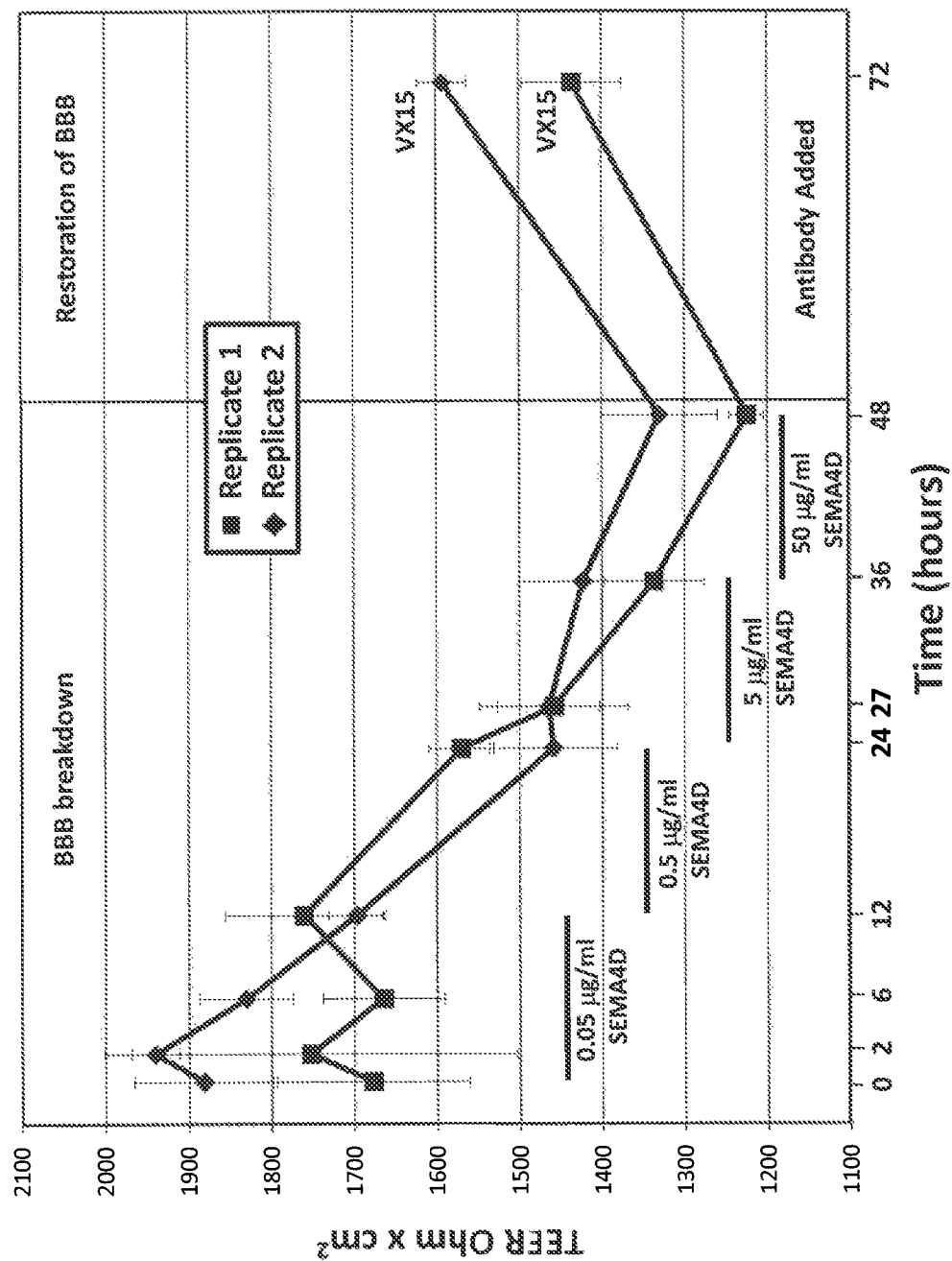

FIG. 2: In vitro DIV-BBB model showing measurements of BBB integrity as reflected in transendothelial electrical resistance (TEER) in the presence of recombinant SEMA4D (0.05, 0.5, 5 or 50 µg/mL) and VX15/2503 Antibody ("VX15").

Figure 3:
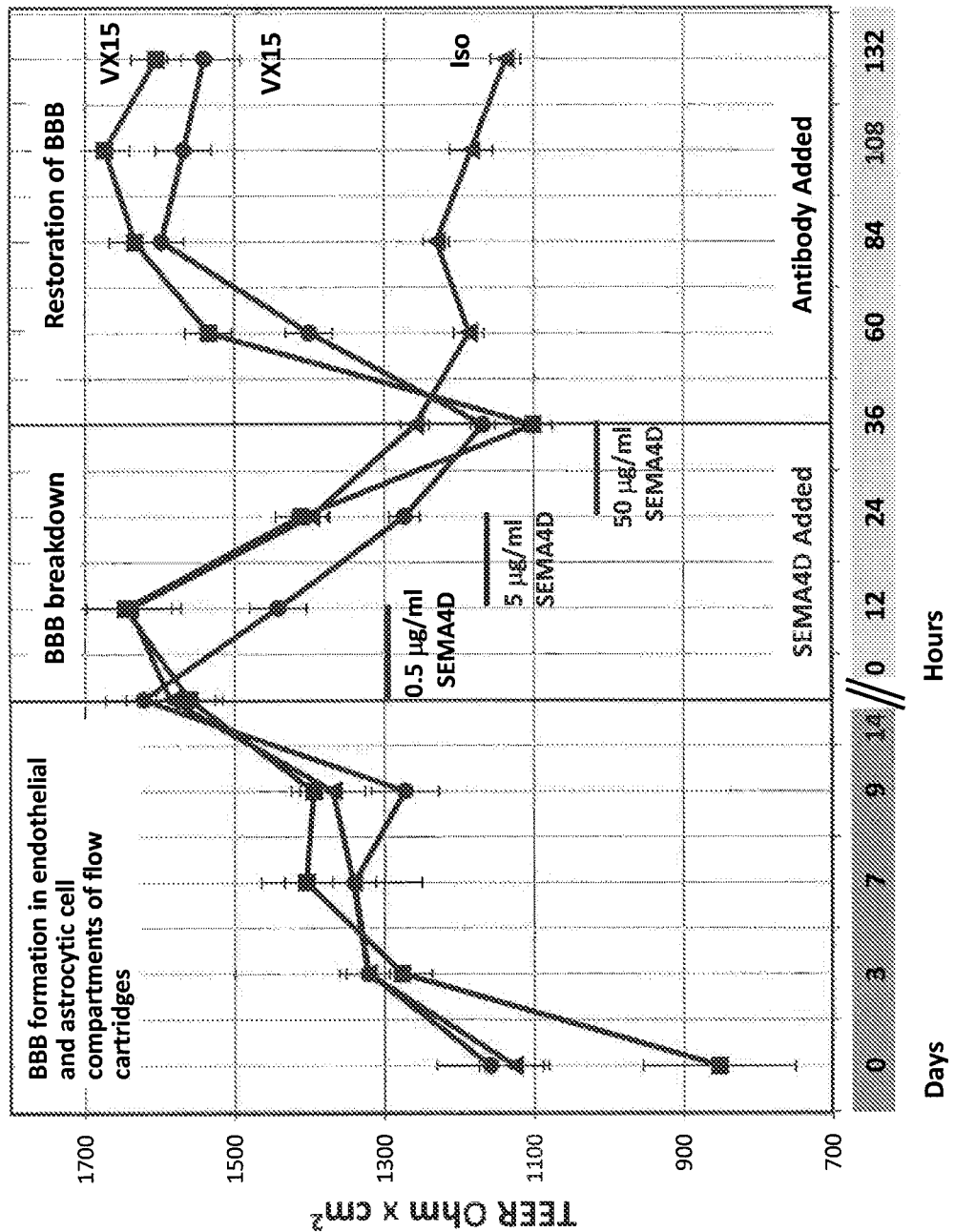

FIG. 3: In vitro DIV-BBB model showing measurements of BBB integrity as reflected in transendothelial electrical resistance (TEER) during the formation of the BBB, the breakdown of BBB in the presence of recombinant SEMA4D (0.5, 5 or 50 µg/mL), and the restoration of the BBB in presence of VX15/2503 Antibody ("VX15"), but not isotype control ("Iso").

Figure 4:
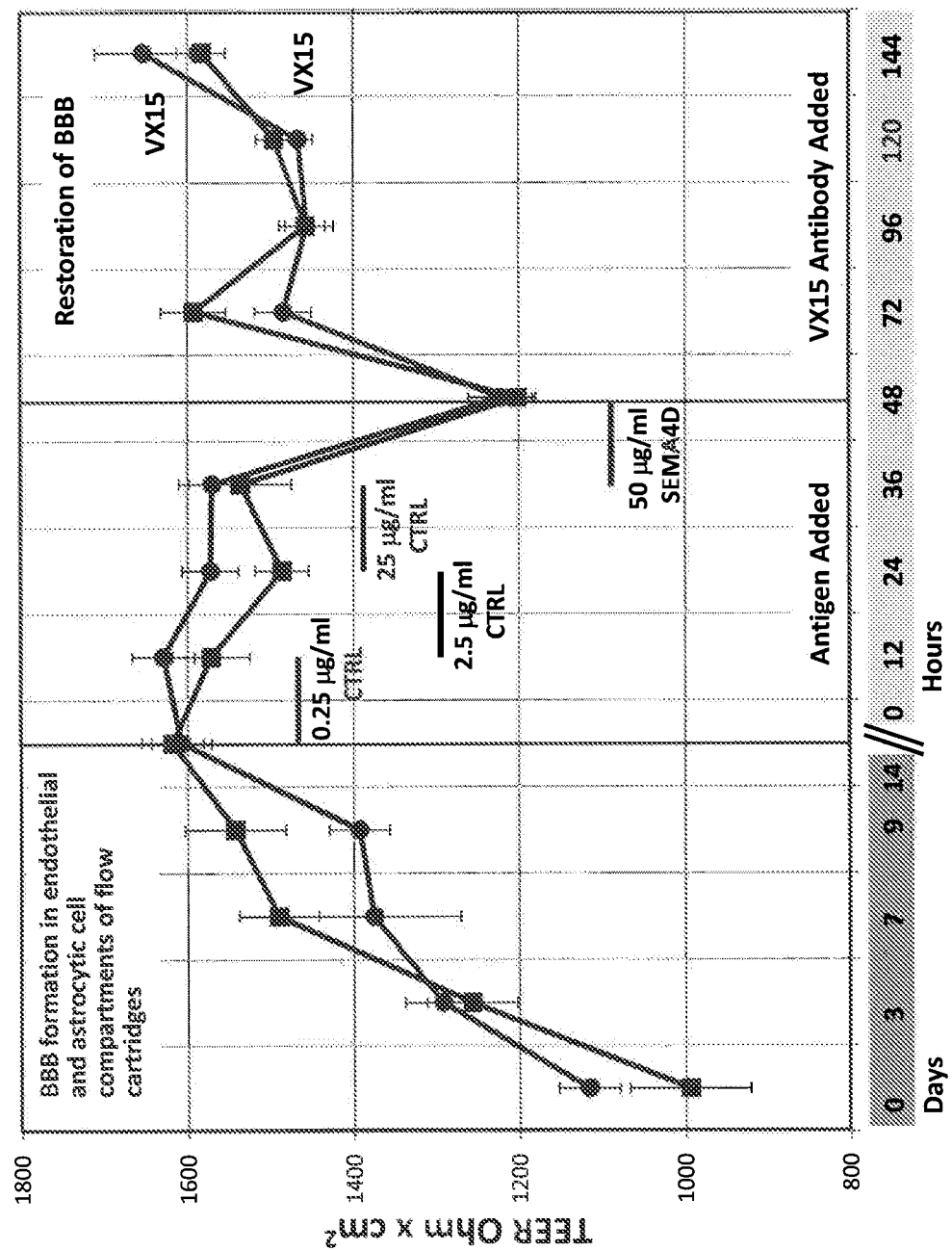

FIG. 4: In vitro DIV-BBB model showing measurements of BBB integrity as reflected in transendothelial electrical resistance (TEER) during the formation of the BBB, the breakdown of BBB in the presence of 0.25, 2.5, or 25 µg/mL of control C35 antigen ("CTRL") or 50 µg/mL of recombinant SEMA4D, and the restoration of the BBB in presence of VX15/2503 Antibody ("VX15").

Figure 5:
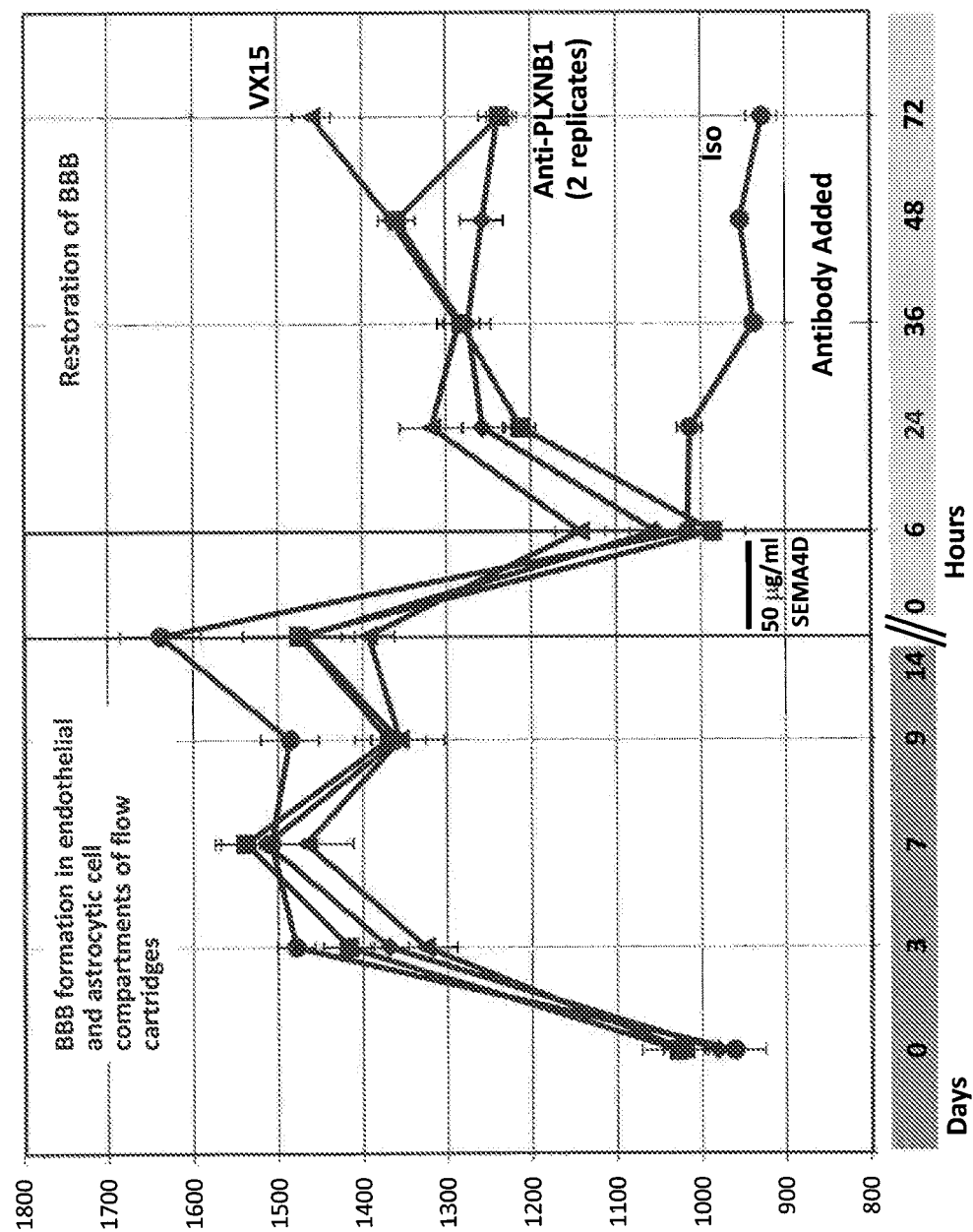

FIG. 5: In vitro DIV-BBB model showing measurements of BBB integrity as reflected in transendothelial electrical resistance (TEER) during the formation of the BBB, the breakdown of BBB in the presence of recombinant SEMA4D (50 µg/mL), and the restoration of the BBB in the presence of VX15/2503 Antibody ("VX15"), anti-Plexin-B1 antibody ("Anti-PLXNB1"), but not isotype control ("Iso").

Figure 6:
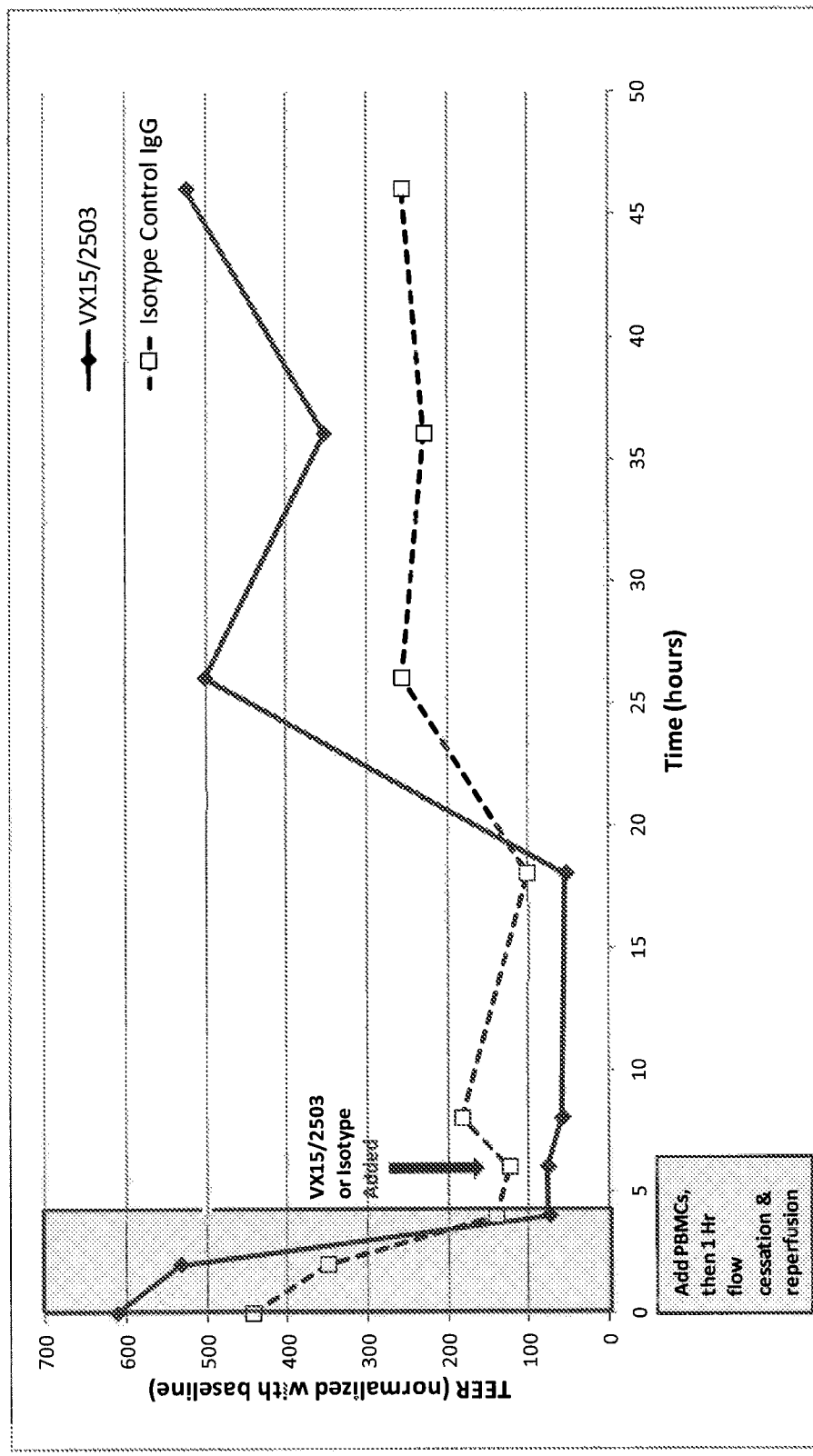

FIG. 6: In vitro DIV-BBB model showing measurements of BBB integrity as reflected in transendothelial electrical resistance (TEER) during the formation of the BBB, the breakdown of BBB in the presence of activated PBMC ($10^6$/ml) and flow cessation, and the restoration of the BBB in the presence of VX15/2503 Antibody or Isotype Control IgG.

FIG. 7A-C: Results from the in vivo EAE model showing integrity of the BBB or loss thereof as reflected by immunostaining of fibrinogen ("Fib.+") penetration into brain tissue (7A left panel and quantitation in 7B) and Claudin-5 ("CLN5+") expression as detected by red stain (7A right panel and quantitation in 7C) following treatment with VX15/2503 antibody ("Anti-SEMA4D") or isotype control ("Control IgG").

FIG. 8: Immunoblot results showing the effect of increasing concentrations of recombinant SEMA4D (1 ng/ml, long/ml and 100 ng/ml) on the expression of the key endothelial tight junction protein Claudin-5 ("CLN-5") compared to VEGF-A positive control in primary mouse central nervous system (CNS) endothelial cultures.

DETAILED DESCRIPTION OF THE INVENTION

I. Definitions

It is to be noted that the term "a" or "an" entity refers to one or more of that entity; for example, "an anti-SEMA4D antibody" is understood to represent one or more anti-SEMA4D antibodies. As such, the terms "a" (or "an"), "one or more," and "at least one" can be used interchangeably herein.

It should be noted that the term "blood brain barrier" and "BBB" are used interchangeably.

As used herein, the term "breakdown" or "disruption" with regards to the BBB, such as "blood brain barrier breakdown", "blood brain barrier disruption", "breakdown of the blood brain barrier", or "disruption of the blood brain barrier" refers to an increase in permeability of the blood brain barrier, or, in the case of the "DIV-BBB," a humanized dynamic in vitro model of BBB, a decrease in transendothelial electrical resistance (TEER). McCallister et al., Brain Res. 904:20-30 (2001); Santaguida et al., Brain Res. 1109: 1-13 (2006); and Cucullo et al., Epilepsia 48:505-16 (2007) have shown that there is a direct (inverse) relationship between TEER and permeability in DIV-BBB. In addition, an increase in the permeability of the blood brain barrier or a decrease in electrical resistance can be the result of a decrease in the number, density and/or concentration of endothelial cells present on the BBB; or a change in the morphology or interactions among endothelial cells or astrocytes or between endothelial cells and astrocytes that form the BBB.

As used herein, the term "restoration" with regards to the BBB, such as "blood brain barrier restoration" or "restoration of the blood brain barrier" refers to a decrease in permeability of the blood brain barrier, or, in the case of the DIV-BBB, a humanized dynamic in vitro model of BBB, an increase in transendothelial electrical resistance.

As used herein, the term "neuroinflammatory disorder" refers to a central nervous system (CNS) inflammatory disorder, a neurodegenerative disorder, an autoimmune disorder of the central nervous system, a myelin disorder or a disease that affects oligodendrocytes, or a post-trauma myelin disorder of the central nervous system. It should be noted that neuroinflammatory disorders are often also neurodegenerative disorders. However, it is possible for a neurodegenerative disorder to exist in the absence of obvious neuroinflammation. This is the case, for example, in late stage secondary progressive multiple sclerosis.

The term "therapeutically effective amount" refers to an amount of an antibody, polypeptide, polynucleotide, small organic molecule, or other drug effective to "treat" a disease or disorder in a subject or mammal. In the case of a neuroinflammatory disorder, the therapeutically effective amount of the drug can decrease the permeability of the BBB; reduce, retard or stop an increase in BBB permeability; inhibit, e.g., suppress, retard, prevent, stop, or reverse an increased permeability of the BBB; increase the number, density and/or concentration of endothelial cells present on the BBB; change in the morphology or function of endothelial cells; or a change in the interactions among endothelial cells or astrocytes or between endothelial cells and astrocytes that form the BBB; relieve to some extent one or more of the symptoms associated with an increased BBB permeability, e.g., neuroinflammatory disorders; reduce morbidity and mortality; improve quality of life; or a combination of such effects.

Terms such as "treating" or "treatment" or "to treat" or "alleviating" or "to alleviate" refer to both 1) therapeutic measures that cure, slow down, lessen symptoms of, reverse, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

As used herein, phrases such as "a subject that would benefit from administration of an anti-SEMA4D antibody" and "an animal in need of treatment" includes subjects, such as mammalian subjects, that would benefit from administration of an anti-SEMA4D antibody or other SEMA4D binding molecule used, e.g., for detection of a SEMA4D polypeptide (e.g., for a diagnostic procedure) and/or from treatment, i.e., palliation or prevention of a disease, with an anti-SEMA4D antibody or other SEMA4D binding molecule.

A "binding molecule" or "antigen binding molecule" of the present invention refers in its broadest sense to a molecule that specifically binds an antigenic determinant. In one embodiment, the binding molecule specifically binds to SEMA4D, e.g., to a transmembrane SEMA4D polypeptide of about 150 kDa or a soluble SEMA4D polypeptide of about 120 kDa (commonly referred to as sSEMA4D). In another embodiment, a binding molecule of the invention is an antibody or an antigen binding fragment thereof. In another embodiment, a binding molecule of the invention comprises at least one heavy or light chain CDR of an antibody molecule. In another embodiment, a binding molecule of the invention comprises at least two CDRs from one or more antibody molecules. In another embodiment, a binding molecule of the invention comprises at least three CDRs from one or more antibody molecules. In another embodiment, a binding molecule of the invention comprises at least four CDRs from one or more antibody molecules. In another embodiment, a binding molecule of the invention comprises at least five CDRs from one or more antibody molecules. In another embodiment, a binding molecule of the invention comprises at least six CDRs from one or more antibody molecules.

The present application is directed to a method of decreasing blood brain barrier permeability in a subject having a neuroinflammatory disorder (e.g., Multiple Sclerosis, Amyotrophic Lateral Sclerosis, epilepsy, Alzheimer's Disease, Parkinson's Disease, meningitis, brain edema, brain trauma, and stroke), comprising administering to the subject an anti-SEMA4D binding molecule, an anti-PlexinB1 binding molecule, or combination thereof.

As used herein, "anti-SEMA4D binding molecule" or "anti-PlexinB1 binding molecule" refers to an antibody, or antigen-binding fragment, variant, or derivative thereof. Unless specifically referring to full-sized antibodies such as naturally occurring antibodies, the term "anti-SEMA4D antibody" or "anti-PlexinB1 antibody" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "inhibitor of SEMA4D interaction with a SEMA4D receptor" refers to an "anti-SEMA4D binding molecule", an "anti-PlexinB1 binding molecule" as well as a small molecule inhibitor of SEMA4D or a SEMA4D receptor.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a SEMA4D polypeptide or fragment or variant thereof. Standard techniques known to those of skill in the art can be used to introduce mutations in the nucleotide sequence encoding a human anti-SEMA4D antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

In certain embodiments, the amino acid substitutions are conservative amino acid substitution, discussed further below. Alternatively, mutations can be introduced randomly along all or part of the coding sequence, such as by saturation mutagenesis, and the resultant mutants can be screened for biological activity to identify mutants that retain activity (e.g., the ability to bind a SEMA4D polypeptide, e.g., human, murine, or both human and murine SEMA4D). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As used herein, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\varepsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia |
| --- | --- | --- |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-SEMA4D antibody or antigen-binding fragment, variant, or derivative thereof of the present invention are according to the Kabat numbering system.

Antibodies or antigen-binding fragments, variants, or derivatives thereof of the invention include, but are not limited to, polyclonal, monoclonal, multispecific and bispecific in which at least one arm is specific for SEMA4D, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-SEMA4D antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. In certain embodiments, a polypeptide comprising a heavy chain portion comprises at least one of: a VH domain, a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain anti-SEMA4D antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding molecule for use in the methods disclosed herein may be derived from different immunoglobulin molecules. For example, a heavy chain portion of a polypeptide can comprise a Cm domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. Preferably, the light chain portion comprises at least one of a VL or CL domain.

Anti-SEMA4D antibodies, or antigen-binding fragments, variants, or derivatives thereof disclosed herein may be described or specified in terms of the epitope(s) or portion(s) of an antigen, e.g., a target polypeptide disclosed herein (e.g., SEMA4D) that they recognize or specifically bind. The portion of a target polypeptide that specifically interacts with the antigen binding domain of an antibody is an "epitope," or an "antigenic determinant." A target polypeptide can comprise a single epitope, but typically comprises at least two epitopes, and can include any number of epitopes, depending on the size, conformation, and type of antigen. Furthermore, it should be noted that an "epitope" on a target polypeptide may be or may include non-polypeptide elements, e.g., an epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-SEMA4D antibodies of the present invention may contain a sequence of at least 4, at least 5, at least 6, at least 7, more preferably at least 8, at least 9, at least 10, at least 15, at least 20, at least 25, or between about 15 to about 30 contiguous or non-contiguous amino acids of SEMA4D.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope. An antibody or antigen-binding fragment, variant, or derivative disclosed herein may be said to bind a target polypeptide disclosed herein (e.g., SEMA4D, e.g., human, murine, or both human and murine SEMA4D) or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, an antibody of the invention may be said to bind a target polypeptide disclosed herein (e.g., SEMA4D, e.g., human, murine, or both human and murine SEMA4D) or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$.

An antibody or antigen-binding fragment, variant, or derivative disclosed herein may be said to bind a target polypeptide disclosed herein (e.g., SEMA4D, e.g., human, murine, or both human and murine SEMA4D) or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, an antibody of the invention may be said to bind a target polypeptide disclosed herein (e.g., SEMA4D, e.g., human, murine, or both human and murine SEMA4D) or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-SEMA4D antibodies or antigen-binding fragments, variants, or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Anti-SEMA4D binding molecules, e.g., antibodies or antigen-binding fragments, variants or derivatives thereof, of the invention may also be described or specified in terms of their binding affinity to a polypeptide of the invention, e.g., SEMA4D, e.g., human, murine, or both human and murine SEMA4D. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In certain embodiments, the anti-SEMA4D binding molecule, e.g., an antibody or antigen binding fragment thereof, of the invention binds human SEMA4D with a Kd of about $5 \times 10^{-9}$ to about $6 \times 10^{-9}$. In another embodiment, the anti-SEMA4D binding molecule, e.g., an antibody or antigen binding fragment thereof, of the invention binds murine SEMA4D with a Kd of about $1 \times 10^{-9}$ to about $2 \times 10^{-9}$.

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g., mouse or primate) and the constant region is human.

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

It is further recognized that the framework regions within the variable domain in a heavy or light chain, or both, of a humanized antibody may comprise solely residues of human origin, in which case these framework regions of the humanized antibody are referred to as "fully human framework regions" (for example, MAb VX15/2503, disclosed in U.S. Patent Appl. Publication No. US 2010/0285036 A1 as MAb 2503, incorporated herein by reference in its entirety). Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the SEMA4D antigen. A human framework region that has been engineered in this manner would thus comprise a mixture of human and donor framework residues, and is referred to herein as a "partially human framework region."

For example, humanization of an anti-SEMA4D antibody can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent or mutant rodent CDRs or CDR sequences for the corresponding sequences of a human anti-SEMA4D antibody. See also U.S. Pat. Nos. 5,225,539; 5,585,089; 5,693,761; 5,693,762; 5,859,205; herein incorporated by reference. The resulting humanized anti-SEMA4D antibody would comprise at least one rodent or mutant rodent CDR within the fully human framework regions of the variable domain of the heavy and/or light chain of the humanized antibody. In some instances, residues within the framework regions of one or more variable domains of the humanized anti-SEMA4D antibody are replaced by corresponding non-human (for example, rodent) residues (see, for example, U.S. Pat. Nos. 5,585,089; 5,693,761; 5,693,762; and 6,180,370), in which case the resulting humanized anti-SEMA4D antibody would comprise partially human framework regions within the variable domain of the heavy and/or light chain.

Furthermore, humanized antibodies can comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., *Nature* 331:522-525 (1986); Riechmann et al., *Nature* 332:323-329 (1988); and Presta, *Curr. Op. Struct. Biol.* 2:593-596 (1992); herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

II. Blood Brain Barrier ("BBB")

The blood-brain barrier (BBB) is an active interface between circulating blood and the central nervous system (CNS). The BBB restricts the free movement of different substances between the two compartments and plays a crucial role in the maintenance of the homeostasis of the CNS. The BBB has both a barrier function and a carrier function. As a barrier, the BBB restricts the movement of cells and potentially toxic or harmful substances from the blood to the brain. As a carrier, on the other hand, the BBB is responsible for transporting nutrients to the brain and removing metabolites.

The BBB is primarily composed of three components: endothelial cells, astrocytes, and pericytes. Endothelial cells form a continuous sheet covering the inner surface of the capillaries and blood vessels in the brain. (Ransohoff et al., "Three or More Routes for Leukocyte Migration Into the Central Nervous System," *Nature Rev. Immun.* 3:569-581 (2003). The endothelial cells are located adjacent to the basal membrane, which consists mainly of collagen IV, fibronectin, laminin and proteoglycans, and are interconnected by tight junctions that form a belt-like structure at the apical region of the cells. Endothelial cells restrict the diffusion of microscopic objects (e.g. bacteria) and large or hydrophilic molecules into the brain parenchyma and cerebrospinal fluid (CSF), while allowing the diffusion of small hydrophobic molecules ($O_2$, hormones, $CO_2$). Cells of the barrier actively transport metabolic products such as glucose across the barrier with specific proteins.

The endothelial cells which form the brain capillaries are different from those found in other tissues in the body. Brain capillary endothelial cells are joined together by tight intercellular junctions that form a continuous wall against the passive diffusion of molecules from the blood to the brain and other parts of the CNS (including Cerebrospinal Fluid, CSF). These cells are also different in that they have few pinocytic vesicles which in other tissues allow somewhat unselective transport across the capillary wall. Also lacking are continuous gaps or channels running between the cells which would allow unrestricted passage.

In addition to endothelial cells, the BBB is also composed of pericytes and astrocytes. Pericytes are located within the basal membrane, interact with endothelial cells and play an important role in the regulation of endothelial proliferation, angiogenesis and inflammatory processes. Astrocytes are characteristic star-shaped glial cells in the brain and spinal cord and are the most abundant cell of the human brain. They perform many functions, including biochemical support of endothelial cells that form the blood-brain barrier, provision of nutrients to the nervous tissue, maintenance of extracellular ion balance, and a role in the repair and scarring process of the brain and spinal cord following traumatic injuries.

The blood-brain barrier functions to ensure that the environment of the brain is constantly controlled. The levels of various substances in the blood, such as hormones, amino acids, and ions, undergo frequent small fluctuations which can be brought about by activities such as eating and exercise (Goldstein et al., "The Blood-Brain Barrier," Scientific American 255:74-83 (1986); Pardridge, "Receptor-Mediated Peptide Transport Through the Blood-Brain Barrier," *Endocrin. Rev.* 7:314-330 (1986)). If the brain was not protected by the blood brain barrier from these variations in serum composition, the result could be uncontrolled neural activity.

The isolation of the brain from the bloodstream is not complete. If this were the case, the brain would be unable to function properly due to a lack of nutrients and because of the need to exchange chemicals with the rest of the body. The presence of specific transport systems within the capillary endothelial cells assures that the brain receives, in a controlled manner, all of the compounds required for normal growth and function. In many instances, these transport systems consist of membrane-associated proteins, which selectively bind and transport certain molecules across the barrier membranes. These transporter proteins are known as solute carrier transporters.

Although the BBB serves to protect the brain and the central nervous system from damage from foreign or external molecules and cells, foreign or external molecules and cells can often cross the BBB and, in limited numbers, may even be beneficial such as for immune surveillance of the CNS. However, when highly active cells, such as, for instance, B cells, T cells, leukocytes and macrophages, cross the BBB in excess and reach the brain, they can cause damage to the brain. Patients suffering from edema, brain traumas, stroke and multiple sclerosis, for instance, exhibit a breakdown of the BBB.

The effect of the BBB on various neuroinflammatory disorders has been studied. (Zlokovic B V, "The Blood-Brain Barrier in Health and Chronic Neurodegenerative Disorders," Neuron 57: 178-201 (2008); Zhong Z et al., "ALS-causing SOD1 mutants generate vascular changes prior to motor neuron degeneration," Nature Neuroscience 11(4): 420-422 (2008); Hawkins B T et al., "The Blood-Brain Barrier/neurovascular Unit in Health and Disease," Pharmacological Rev 57 (2): 173-185 (2005); Oby E et al., "The Blood-Brain Barrier and Epilepsy," Epilepsia 47(11); 1761-1774 (2006)). Moreover, there is increasing evidence that inflammation and the blood-brain barrier (BBB) (Banks and Erickson, 2010; Lochhead et al, 2010) are involved in the pathogenesis of neurologic diseases such as meningitis (van der et al, 2004), brain edema (Stamatovic et al, 2006), Alzheimer's disease (Kalaria, 1992), Parkinson's disease (Westin, J. E., et. al., "Endothelial Proliferation and Increased Blood-Brain Barrier Permeability in the Basal Ganglia in a Rat Model of 3,4-Dihydroxyphenyl-L-Alanine-Induced Dyskinesia," The Journal of Neuroscience 26(37): 9448-9461 (2006)) and multiple sclerosis (Minagar and Alexander, 2003).

In the case of multiple sclerosis, for instance, it has been shown using Magnetic Resonance Imaging ("MRI"), that when a person is undergoing an MS "attack," the BBB has broken down in a section of the brain or spinal cord, allowing T lymphocytes to cross over and attack the myelin that protects and insulates the neurons of the central nervous systems in both brain and spinal cord. (Zlokovic 2008; Waubant E., "Biomarkers indicative of blood-brain barrier disruption in multiple sclerosis". Disease Markers 22 (4): 235-44 (2006)).

Meningitis, on the other hand, occurs when there is an inflammation of the membranes that surround the brain and spinal cord (these membranes are known as meninges). When the meninges are inflamed, the blood-brain barrier may be disrupted, allowing both inflammatory cells and various substances (including either toxins or antibiotics) to enter the brain. (Beam, T R Jr., et al. (December 1977). "Blood, brain, and cerebrospinal fluid concentrations of several antibiotics in rabbits with intact and inflamed meninges". Antimicrobial Agents and Chemotherapy 12 (6): 710-6).

Similarly, in the case of Parkinson's Disease (PD), it has been suggested that absorption or metabolism of putative PD toxins, and their faulty elimination across the BBB, due to low activity of the transporter P-glycoportein (P-gp), an ATP-dependent efflux pump which mediates rapid removal of ingested toxic lipophilic metabolites, may play a role in the pathogenesis of PD (Kortekaas, R., Leenders, K. L., van Oostrom, J. C., Vaalburg, W., Bart, J., Willemsen, A. T., and Hendrikse, N. H. *Blood-brain barrier dysfunction in parkinsonian midbrain in vivo.* Ann. Neurol. 57, 176-179, 2005). Neuroinflammation also appears to be a ubiquitous finding in PD patients and experimental models of PD. Phagocyte activation, increased synthesis and release of proinflammatory cytokines, complement activation, activation of microglia, and release of reactive oxygen species (ROS) have been described (Whitton, P. S. *Inflammation as a causative factor in the aetiology of Parkinson's disease.* Br. J. Pharmacol. 150, 963-976, 2007).

In epilepsy, studies have implicated the failure of blood-brain barrier function in triggering chronic or acute seizures due to certain interactions between a common blood protein, albumin, and astrocytes. These findings suggest that acute seizures are a result of disruption of the BBB by either artificial or inflammatory mechanisms. (Oby, E; et al. (2006). "The Blood-Brain Barrier and Epilepsy" (PDF). Epilepsia 47 (11): 1761-1774).

In patients with Alzheimer's Disease (AD), evidence points to the disruption of the blood-brain barrier in allowing blood plasma containing amyloid beta (Aβ) to enter the brain though RAGE, a major influx transporter for Aβ across the BBB. Studies have shown that the Aβ/RAGE interaction results in transcytosis of circulating Aβ across the BBB into the brain parenchyma and its binding to neurons, NF-kB-mediated endothelial activation resulting in secretion of proinflammatory cytokines, the expression of adhesion molecules, and the generation of endothelin-1, which suppresses CBF (Cerebral Blood Flow). Moreover, it has been shown that the Aβ/RAGE interaction contributes to neuronal killing by producing oxidative damage to RAGE-expressing neurons and by activating microglia. (Zlokovic, B. V. The Blood-Brain Barrier in Health and Chronic Neurodegenerative Disorders. Neuron 57, 178-201, 2008). Faulty efflux of Aβ out of the brain parenchyma and into the microvasculature via the BBB has also been found in the setting of AD pathogenesis and has been attributed, in part, to compromised low-density lipoprotein receptor related protein 1 (LRP1) function. LRP1 is an abluminal BBB membrane protein that binds and transports different structural conformers of Aβ (Deane et al., "LRP/amyloid beta-peptide interaction mediates differential brain efflux of Abeta isoforms." Neuron 43, 333-344, 2004). Aβ exposure shifts cell surface expression patterns of tight junction proteins, including claudin-5 and ZO-2, on brain microvascular endothelial cells to the cytoplasm (Marco et al., "Amyloid β-peptide 1-42 alters tight junction protein distribution and expression in brain microvessel endothelial cells." Neurosci. Lett. 401, 219-224, 2006), and severely compromises transendothelial electrical resistance (TEER) of monolayers of these cells (Gonzalez-Velasquez et al., "Soluble aggregates of the amyloid-beta protein selectively stimulate permeability in human brain microvascular endothelial monolayers." J. Neurochem. 107, 466-477, 2008).

In Amyotrophic lateral sclerosis (ALS), studies have suggested that BBB breakdown may result in leakage of serum proteins that interact with motor neurons to produce ROS (Reactive Oxygen Species) and initiate an autoimmune response, causing demyelination, disruption of neuronal transmission, and cell death. (Zlokovic 2008).

A recent study suggests that the weakening of the BBB can result from a disturbance in endothelial cells mediated through their VEGF-A receptor. (Argaw A T et al., "VEGF-mediated disruption of endothelial CLN-5 promotes blood-brain barrier breakdown," PNAS 106(6): 1977-1982 (2009)). According to that study, VEGF-A, which is derived from astrocytes, targets and disrupts expression of both endothelial transmembrane tight junction proteins claudin-5

(CLN-5) and occludin (OCLN). As expression of both CLN-5 and OCLN decreases, breakdown of the BBB increases.

As shown in the present examples, another possible mechanism for the weakening of the BBB is as a result of endothelial cell disturbance through the Plexin-B1 high affinity (1 nM) receptor for SEMA4D. Plexin-B1 can be expressed by endothelial cells. In the presence of SEMA4-D, endothelial cells may undergo a transformation which alters the morphology or function of the endothelial cells so as to cause a weakening of the BBB, for example, through modification of tight junctions. This weakening of the BBB may, in turn, increase permeability of the BBB to cells and molecules and allow such cells and molecules to enter and alter activity of the brain and central nervous system. Addition of either anti-SEMA4D or anti-Plexin-B1, consequently, may prevent endothelial cells from undergoing a transformation and reduce weakening of the BBB.

III. Target Polypeptide Description

As used herein, the terms "semaphorin-4D," "SEMA4D" and "SEMA4D polypeptide" are used interchangeably, as are "SEMA4D" and "Sema4D." In certain embodiments, SEMA4D is expressed on the surface of or secreted by a cell. In another embodiment, SEMA4D is membrane bound. In another embodiments, SEMA4D is soluble, e.g., sSEMA4D. In other embodiments, SEMA4D may include a full-sized SEMA4D or a fragment thereof, or a SEMA4D variant polypeptide, wherein the fragment of SEMA4D or SEMA4D variant polypeptide retains some or all functional properties of the full-sized SEMA4D.

The full-sized human SEMA4D protein is a homodimeric transmembrane protein consisting of two polypeptide chains of 150 kDa. SEMA4D belongs to the semaphorin family of cell surface receptors and is also referred to as CD100. Both human and mouse SEMA4D/Sema4D are proteolytically cleaved from their transmembrane form to generate 120-kDa soluble forms, indicating the existence of two Sema4D isoforms (Kumanogoh et al., *J. Cell Science* 116(7):3464 (2003)). Semaphorins include soluble and membrane-bound proteins that were originally defined as axonal-guidance factors during development which play an important role in establishing precise connections between neurons and their appropriate target. Structurally considered a class IV semaphorin, full-sized SEMA4D includes an amino-terminal signal sequence followed by a characteristic 'Sema' domain, which contains 17 conserved cysteine residues, an Ig-like domain, a lysine-rich stretch, a hydrophobic transmembrane region, and a cytoplasmic tail.

Each polypeptide chain of SEMA4D includes a signal sequence of about 13 amino acids followed by a semaphorin domain of about 512 amino acids, an immunoglobulin-like (Ig-like) domain of about 65 amino acids, a lysine-rich stretch of 104 amino acids, a hydrophobic transmembrane region of about 19 amino acids, and a cytoplasmic tail of 110 amino acids. A consensus site for tyrosine phosphorylation in the cytoplasmic tail supports the predicted association of SEMA4D with a tyrosine kinase (Schlossman, et al., Eds. (1995) Leucocyte Typing V (Oxford University Press, Oxford)).

SEMA4D is known to have at least two receptors. One of the receptors, Plexin-B1, is expressed in non-lymphoid tissues and has been shown to be a high affinity (1 nM) receptor for SEMA4D (Tamagnone et al., *Cell* 99:71-80 (1999)). SEMA4D stimulation of Plexin-B1 signaling has been shown to induce growth cone collapse of neurons, and to induce process extension collapse and apoptosis of oligodendrocytes (Giraudon et al., *J. Immunol.* 172:1246-1255 (2004); Giraudon et al., *NeuroMolecular Med.* 7:207-216 (2005)). After binding to SEMA4D, Plexin-B1 signaling mediates the inactivation of R-Ras, leading to a decrease in the integrin mediated attachment to the extracellular matrix, as well as to activation of RhoA, leading to reorganization of the cytoskeleton and cell migration. See Kruger et al., *Nature Rev. Mol. Cell Biol.* 6:789-800 (2005); Pasterkamp, *TRENDS in Cell Biology* 15:61-64 (2005)).

In lymphoid tissues CD72 is utilized as a low affinity (300 nM) SEMA4D receptor (Kumanogoh et al., *Immunity* 13:621-631 (2000)). B cells and APCs express CD72, and anti-CD72 antibodies have many of the same effects as sSEMA4D, such as enhancement of CD40-induced B cell responses and B cell shedding of CD23. CD72 is thought to act as a negative regulator of B cell responses by recruiting the tyrosine phosphatase SHP-1, which can associate with many inhibitory receptors. Interaction of SEMA4D with CD72 results in the dissociation of SHP-1, and the loss of this negative activation signal. SEMA4D has been shown to promote T cell stimulation and B cell aggregation and survival in vitro. The addition of SEMA4D-expressing cells or sSEMA4D enhances CD40-induced B cell proliferation and immunoglobulin production in vitro, and accelerates in vivo antibody responses (Ishida et al., *Inter. Immunol.* 15:1027-1034 (2003); Kumanogoh and H. Kukutani, *Trends in Immunol.* 22:670-676 (2001)). sSEMA4D enhances the CD40 induced maturation of DCs, including up-regulation of costimulatory molecules and increased secretion of IL-12. In addition, sSEMA4D can inhibit immune cell migration, which can be reversed by addition of blocking anti-SEMA4D antibodies (Elhabazi et al., *J. Immunol.* 166:4341-4347 (2001); Delaire et al., *J. Immunol.* 166:4348-4354 (2001)).

Sema4D is expressed at high levels in lymphoid organs, including the spleen, thymus, and lymph nodes, and in non-lymphoid organs, such as the brain, heart, and kidney. In lymphoid organs, Sema4D is abundantly expressed on resting T cells but only weakly expressed on resting B cells and antigen-presenting cells (APCs), such as dendritic cells (DCs). Cellular activation increases the surface expression of SEMA4D as well as the generation of soluble SEMA4D (sSEMA4D).

The expression pattern of SEMA4D suggests that it plays an important physiological role as well as pathological role in the immune system. SEMA4D has been shown to promote B cell activation, aggregation and survival; enhance CD40-induced proliferation and antibody production; enhance antibody response to T cell dependent antigens; increase T cell proliferation; enhance dendritic cell maturation and ability to stimulate T cells; and is directly implicated in demyelination and axonal degeneration (Shi et al., *Immunity* 13:633-642 (2000); Kumanogoh et al., *J Immunol* 169:1175-1181 (2002); and Watanabe et al., *J Immunol* 167:4321-4328 (2001)).

SEMA4D knock out (SEMA4D−/−) mice have provided additional evidence that SEMA4D plays an important role in both humoral and cellular immune responses. There are no known major abnormalities of non-lymphoid tissues in SEMA4D−/− mice. Dendritic cells (DCs) from the SEMA4D−/− mice have poor allostimulatory ability and show defects in expression of costimulatory molecules, which can be rescued by the addition of sSEMA4D. Mice deficient in SEMA4D (SEMA4D−/−) fail to develop experimental autoimmune encephalomyelitis induced by myelin oligodendrocyte glycoprotein peptide, because myelin oligodendrocyte glycoprotein-specific T cells are poorly generated in the absence of SEMA4D (Kumanogoh et al., *J Immunol* 169:1175-1181 (2002)). A significant amount of soluble SEMA4D is also detected in the sera of autoimmunity-prone MRL/lpr mice (model of systemic autoimmune diseases such as SLE), but not in normal mice. Further, the levels of sSEMA4D correlate with levels of auto-antibodies and increase with age (Wang et al., *Blood* 97:3498-3504 (2001)). Soluble SEMA4D has also been shown to accumulate in the cerebral spinal fluid and sera of patients with demyelinating disease, and sSEMA4D induces apoptosis of human pluripotent neural precursors (Dev cells), and both inhibits process extension and induces apoptosis of rat oligodendrocytes in vitro (Giraudon et al., *J Immunol* 172 (2):1246-1255 (2004)). This apoptosis was blocked by an anti-SEMA4D MAb.

IV. Anti-SEMA4D Antibodies

Antibodies that bind SEMA4D have been described in the art. See, for example, US Publ. Nos. 2008/0219971 A1, US 2010/0285036 A1, and US 2006/0233793 A1, International Patent Applications WO 93/14125, WO 2008/100995, and WO 2010/129917, and Herold et al., *Int. Immunol.* 7(1): 1-8 (1995), each of which is herein incorporated in its entirety by reference.

The present application generally relates to a method of decreasing blood brain barrier permeability in a subject, e.g., a human patient, having a neuroinflammatory disorder, e.g., a CNS inflammatory disorder or neurodegenerative disorder, comprising administration of an antibody which specifically binds to SEMA4D, or an antigen-binding fragment, variant, or derivative thereof. In certain embodiments, the antibody blocks the interaction of SEMA4D with one or more of its receptors, e.g., Plexin-B1. Anti-SEMA4D antibodies having these properties can be used in the methods provided herein. Antibodies that can be used include, but are not limited to MAbs VX15/2503, 67, and 76 and antigen-binding fragments, variants, or derivatives thereof which are fully described in US 2010/0285036 A1. Additional antibodies which can be used in the methods provided herein include the BD16 and BB18 antibodies described in US 2006/0233793 A1 as well as antigen-binding fragments, variants, or derivatives thereof; or any of MAb 301, MAb 1893, MAb 657, MAb 1807, MAb 1656, MAb 1808, Mab 59, MAb 2191, MAb 2274, MAb 2275, MAb 2276, MAb 2277, MAb 2278, MAb 2279, MAb 2280, MAb 2281, MAb 2282, MAb 2283, MAb 2284, and MAb 2285, as well as any fragments, variants or derivatives thereof as described in US 2008/0219971 A1. In certain embodiments an anti-SEMA4D antibody for use in the methods provided herein binds human, murine, or both human and murine SEMA4D. Also useful are antibodies which bind to the same epitope as any of the aforementioned antibodies and/or antibodies which competitively inhibit any of the aforementioned antibodies from binding to SEMA4D.

In certain embodiments, an anti-SEMA4D antibody or antigen-binding fragment, variant, or derivative thereof useful in the methods provided herein has an amino acid sequence that has at least about 80%, about 85%, about 88%, about 89%, about 90%, about 91%, about 92%, about 93%, about 94%, or about 95% sequence identity to the amino acid sequence for a reference anti-SEMA4D antibody molecule, for example those described above. In a further embodiment, the binding molecule shares at least about 96%, about 97%, about 98%, about 99%, or 100% sequence identity to a reference antibody.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85% about 90%, about 95%, about 96%, about 97%, about 98%, about 99%, or identical to CDR1, CDR2 or CDR3 of SEQ ID NO: 9 or 10.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 6, SEQ ID NO: 7, or SEQ ID NO: 8.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 6, SEQ ID NO: 7, or SEQ ID NO: 8.

In another embodiment, an anti-SEMA4D antibody or antigen-binding fragment, variant, or derivative thereof useful in the methods provided herein comprises, consists essentially of, or consists of a VH domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 9 or SEQ ID NO: 10, wherein the anti-SEMA4D antibody comprising the encoded VH domain specifically, preferentially, or competitively binds to SEMA4D.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 17 or 18.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 14, SEQ ID NO: 15, or SEQ ID NO: 16.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 14, SEQ ID NO: 15, or SEQ ID NO: 16.

In another embodiment, an anti-SEMA4D antibody or antigen-binding fragment, variant, or derivative thereof useful in the methods provided herein comprises, consists essentially of, or consists of a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 17 or SEQ ID NO: 18, wherein the anti-SEMA4D antibody comprising the encoded VL domain specifically, preferentially, or competitively binds to SEMA4D.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain) and an immunoglobulin light chain variable domain (VL domain), where at least one of the CDRs of the VH domain has an amino acid sequence that is at least about 80%, about 85%, about 90%, about 95%, about 96%, about 97%, about 98%, about 99%, or identical to CDR1, CDR2 or CDR3 of SEQ ID NO: 9 or 10 and at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 17 or 18.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain) and an immunoglobulin light chain variable domain (VL domain), where at least one of the CDRs of the VH domain has an amino acid sequence identical, except for 1, 2, 3, 4, or 5 conservative amino acid substitutions, to SEQ ID NO: 6, SEQ ID NO: 7, or SEQ ID NO: 8 and where at least one of the CDRs of the VL domain has an amino acid sequence identical, except for 1, 2, 3, 4, or 5 conservative amino acid substitutions, to SEQ ID NO: 14, SEQ ID NO: 15, or SEQ ID NO: 16.

In another embodiment, an anti-SEMA4D antibody or antigen-binding fragment, variant, or derivative thereof useful in the methods provided herein comprises, consists essentially of, or consists of a VH domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 9 or SEQ ID NO: 10, and a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 17 or SEQ ID NO: 18, wherein the anti-SEMA4D antibody comprising the encoded VH and VL domains specifically, preferentially, or competitively binds to SEMA4D.

In another embodiment, an anti-SEMA4D antibody or antigen-binding fragment, variant, or derivative thereof useful in the methods provided herein comprises, consists essentially of, or consists of the three CDRs of the VL domain and three CDRs of the VH domain of MAb VX15/2503, 67, or 76, which are fully described in US 2010/0285036 A1. In some embodiments, the anti-SEMA4D antibody useful in the methods provided herein comprises MAb VX15/2503 or 67.

Also included for use in the methods provided herein are polypeptides encoding anti-SEMA4D antibodies, or antigen-binding fragments, variants, or derivatives thereof as described herein, polynucleotides encoding such polypeptides, vectors comprising such polynucleotides, and host cells comprising such vectors or polynucleotides, all for producing anti-SEMA4D antibodies, or antigen-binding fragments, variants, or derivatives thereof for use in the methods described herein.

Suitable biologically active variants of the anti-SEMA4D antibodies of the invention can be used in the methods of the present invention. Such variants will retain the desired binding properties of the parent anti-SEMA4D antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, *Proc. Natl. Acad. Sci. USA* 82:488-492 (1985); Kunkel et al., *Methods Enzymol.* 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, may be preferred. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr.

In constructing variants of the anti-SEMA4D binding molecule, e.g., an antibody or antigen-binding fragment thereof, polypeptides of interest, modifications are made such that variants continue to possess the desired properties, e.g., being capable of specifically binding to a SEMA4D, e.g., human, murine, or both human and murine SEMA4D, e.g., expressed on the surface of or secreted by a cell and having SEMA4D blocking activity, as described herein. Obviously, any mutations made in the DNA encoding the variant polypeptide must not place the sequence out of reading frame and preferably will not create complementary regions that could produce secondary mRNA structure. See EP Patent Application Publication No. 75,444.

Methods for measuring anti-SEMA4D binding molecule, e.g., an antibody or antigen-binding fragment, variant, or derivative thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., *Immunity* 13:633-642 (2000); Kumanogoh et al., *J Immunol* 169:1175-1181 (2002); Watanabe et al., *J Immunol* 167:4321-4328 (2001); Wang et al., *Blood* 97:3498-3504 (2001); and Giraudon et al., *J Immunol* 172(2):1246-1255 (2004), all of which are herein incorporated by reference.

When discussed herein whether any particular polypeptide, including the constant regions, CDRs, VH domains, or VL domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

For purposes of the present invention, percent sequence identity may be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant may, for example, differ from a reference anti-SEMA4D antibody (e.g., MAb VX15/2503, 67 or 76) by as few as 1 to 15 amino acid residues, as few as 1 to 10 amino acid residues, such as 6-10, as few as 5, as few as 4, 3, 2, or even 1 amino acid residue.

The constant region of an anti-SEMA4D antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-SEMA4D antibodies or fragments, variants or derivatives thereof useful in the methods provided herein, the Fc portion can be mutated to decrease effector function using techniques known in the art. For example, the deletion or inactivation (through point mutations or other means) of a constant region domain can reduce Fc receptor binding of the circulating modified antibody thereby increasing tumor localization. In other cases, constant region modifications consistent with the instant invention moderate complement binding and thus reduce the serum half-life. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well known immunological techniques without undue experimentation. Anti-SEMA4D antibodies for use in the methods provided herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-SEMA4D polypeptide, to block SEMA4D interaction with its receptor, or to decrease BBB permeability in a subject, e.g., a patient with a neuroinflammatory disorder).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations may alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a SEMA4D polypeptide) can be determined using techniques described herein or by routinely modifying techniques known in the art.

In certain embodiments, the anti-SEMA4D antibodies for use in the methods provided herein comprise at least one optimized complementarity-determining region (CDR). By "optimized CDR" is intended that the CDR has been modified and optimized to improve binding affinity and/or anti-SEMA4D activity that is imparted to an anti-SEMA4D antibody comprising the optimized CDR. "Anti-SEMA4D activity" or "SEMA4D blocking activity" can include activity which modulates one or more of the following activities associated with SEMA4D: B cell activation, aggregation and survival; CD40-induced proliferation and antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; binding to cell surface Plexin-B 1 or other receptor, or any other activity associated with soluble SEMA4D or SEMA4D that is expressed on the surface of SEMA4D+ cells. Anti-SEMA4D activity can also be attributed to a decrease in incidence or severity of diseases associated with SEMA4D expression or overexpression, including, but not necessarily limited to, neuroinflammatory diseases including central nervous system (CNS) and peripheral nervous system (PNS) inflammatory diseases.

Examples of optimized antibodies based on murine anti-SEMA4D MAbs BD16 and BB18, were described in US Publ. No. 2008/0219971 A1, International Patent Application WO 93/14125 and Herold et al., *Int. Immunol.* 7(1): 1-8 (1995), each of which are herein incorporated by reference in their entirety. The modifications may involve replacement of amino acid residues within the CDR such that an anti-SEMA4D antibody retains specificity for the SEMA4D antigen and has improved binding affinity and/or improved anti-SEMA4D activity.

V. Treatment Methods Using Therapeutic Anti-SEMA4D and Anti-PlexinB1 Antibodies

Methods of the invention are directed to the use of an inhibitor of SEMA4D interaction with a SEMA4D receptor, e.g., anti-SEMA4D binding molecules, anti-PlexinB1 binding molecules, or combination thereof, e.g., antibodies, including antigen-binding fragments, variants, and derivatives thereof, to decrease blood brain barrier permeability in a subject having a neuroinflammatory disorder. In certain embodiments, the neuroinflammatory disorder is, e.g., Multiple Sclerosis, Amyotrophic Lateral Sclerosis, epilepsy, Alzheimer's Disease, Parkinson's Disease, meningitis, brain edema, brain trauma, or stroke. In certain embodiments, the endothelial cells express a SEMA4D receptor; and in certain embodiments, the receptor is Plexin-B1. Although the following discussion refers to administration of an anti-SEMA4D antibody, an anti-PlexinB1 antibody, and combination thereof, the methods described herein are also applicable to the antigen-binding fragments, variants, and derivatives of these anti-SEMA4D or anti-PlexinB1 antibodies that retain the desired properties of the anti-SEMA4D or anti-PlexinB1 antibodies of the invention, e.g., capable of specifically binding SEMA4D, e.g., human, mouse, or human and mouse SEMA4D, having SEMA4D neutralizing activity, and/or blocking the interaction of SEMA-4D with its receptor, e.g., Plexin-B1.

In one embodiment, treatment includes the application or administration of an anti-SEMA4D binding molecule, an anti-PlexinB1 binding molecule, or combination thereof, e.g., an antibody or antigen binding fragment thereof as described herein to a patient, where the patient has, or has the risk of developing a neuroinflammatory disorder. In another embodiment, treatment is also intended to include the application or administration of a pharmaceutical composition comprising the anti-SEMA4D binding molecule, the anti-PlexinB1 binding molecule, or combination thereof, e.g., an antibody or antigen binding fragment thereof to a patient, where the patient has, or has the risk of developing a neuroinflammatory disorder. It should be appreciated that due to the interaction of SEMA4D with a receptor on endothelial cells, the application or administration of an anti-SEMA4D binding molecule, an anti-PlexinB1 binding molecule, or combination thereof is expected to occur on the blood side of the blood brain barrier. By administering an anti-SEMA4D binding molecule, an anti-PlexinB1 binding molecules, or combinations thereof by a route that exposes it to the blood side, e.g. including, but not limited to, intravenous administration, the anti-SEMA4D binding molecule, the anti-PlexinB1 binding molecules, or combinations thereof will be permitted to inhibit the interaction of SEMA4D with the SEMA4D receptor that is expressed by the endothelial cells.

The anti-SEMA4D binding molecules, anti-PlexinB1 binding molecules, or combination thereof, e.g., antibodies or binding fragments thereof as described herein are useful for the treatment of various neuroinflammatory disorders. In some embodiments, treatment of a neuroinflammatory disorder is intended to include a reduction, or decrease, in permeability of the BBB. In other embodiments, treatment of a neuroinflammatory disorder is intended to include an increase in the resistivity of the BBB. In other embodiments, treatment of a neuroinflammatory disorder is intended to include an increase in the number, density and/or concentration of endothelial cells present on the BBB. In other embodiments, treatment of a neuroinflammatory disorder is intended to include a change in the morphology or function or endothelial cells, or in the interactions among endothelial cells or astrocytes or between endothelial cells and astrocytes that form the BBB.

In one embodiment, the invention relates to the use of anti-SEMA4D binding molecules, anti-PlexinB1 binding molecules, or combination thereof, e.g., antibodies or anti-gen-binding fragments, variants, or derivatives thereof, as a medicament, in particular for use in the treatment or prophylaxis of neuroinflammatory disorders to inhibit, reduce, prevent, or minimize a breakdown in the BBB, or an increase in the permeability of the BBB.

In accordance with the methods of the present invention, at least one anti-SEMA4D binding molecule or anti-PlexinB1 binding molecule, e.g., an antibody or antigen binding fragment, variant, or deriviative thereof, as defined elsewhere herein can be used to promote a positive therapeutic response with respect to the neuroinflammatory disorder. A "positive therapeutic response" with respect to the neuroinflammatory disorder is intended to include an improvement in the disease in association with the anti-inflammatory activity, anti-apoptotic activity, or the like, of these antibodies, and/or an improvement in the symptoms associated with the disease. That is, an anti-proliferative effect, the prevention of further proliferation of the SEMA4D-expressing cell, a reduction in the inflammatory response including but not limited to reduced secretion of inflammatory cytokines, adhesion molecules, proteases, immunoglobulins (in instances where the SEMA4D bearing cell is a B cell), combinations thereof, and the like, increased production of anti-inflammatory proteins, a reduction in the number of autoreactive cells, an increase in immune tolerance, inhibition of autoreactive cell survival, reduction in apoptosis, reduction in endothelial cell migration, increase in spontaneous monocyte migration, reduction in and/or a decrease in one or more symptoms mediated by stimulation of sSEMA4D or SEMA4D-expressing cells can be observed. Such positive therapeutic responses are not limited to the route of administration and may comprise administration to the donor, the donor tissue (such as for example organ perfusion), the host, any combination thereof, and the like. In particular, the methods provided herein are directed to inhibiting, preventing, reducing, alleviating, or lessening the development of a neuroinflammatory disorder in a patient. Thus, for example, an improvement in the disease may be characterized as an absence of clinically observable symptoms, a decrease in BBB permeability, an increase in the number, density or concentration of endothelial cells present on the BBB, a change in the morphology or function of the endothelial cells, or a change in the interactions among endothelial cells and pericytes or astrocytes or between endothelial cells, pericytes and astrocytes that form the BBB.

Changes in the permeability of the BBB can be measured using in vitro models. In certain embodiments, a dynamic in vitro DIV-BBB model can be employed. Cucullo et al. have presented a DIV-BBB model composed of normal adult human brain microvascular endothelial cells and human adult astrocytes to study how haemodynamic changes and systemic inflammation affect the integrity of the brain microvasculature. Specifically, this model uses a cartridge, or hollow tube, to represent the blood brain barrier with the interior of the cartridge representing the blood side of the blood brain barrier and the exterior of the cartridge representing the brain side of the blood brain barrier. The interior of the cartridge is lined with adult human brain microvascular endothelial cells and exterior is lined with human adult astrocytes. As a blood brain barrier modifying agent, such as SEMA4D, is introduced into the lumen of the cartridge, the electrical current between the interior and exterior of the tube is monitored using Transendothelial Electrical Resistance Measurement, described below. One embodiment of this model has the novelty of having transcapillary microholes to enable transendothelial cell trafficking between the vascular and the parenchymal compartment. An in depth description of the in vitro DIV-BBB model and the derivation and culture of the human microvascular endothelial cells and adult astrocytes employed can be found in, for instance, Cucullo et al., *Brain Research.* 951 243-254 (2002); and Cucullo et al., *Journal of Cerebral Blood Flow & Metabolism.* 2:767-77 (2011). It should be appreciated that people skilled in the art will recognize that other BBB models have been described and usefully employed for studies of the role of BBB in disease in the prior art and that the present disclosure should not be limited to any one particular model.

The permeability of the BBB can be monitored using Transendothelial Electrical Resistance Measurement (TEER). TEER is used to monitor the integrity of the BBB in real time, which has been shown to correlate with the permeability of the BBB. The TEER system uses electronic multiplexing to measure multiple cartridges in quick succession and assesses the integrity and viability of tissue culture bilayers rapidly and reliably (Cucullo et al., 2002; Cucullo et al., 2010; Santaguida et al, 2006). In operation, the system applies an excitation voltage (0.06V) across the excitation electrodes inserted in each cartridge in the luminal and extraluminal compartments. A microcontroller computes the resistivity and capacitance (per $cm^2$) of the barrier from physical parameters. The values of capacitance are calculated by comparison of the voltage and current waveforms. The delay from peak-to-peak of the two waveforms is proportional to the capacitance value, which is expressed as arch tension. The TEER can be measured from the initial setup throughout the course of each experiment.

The anti-SEMA4D binding molecules, anti-PlexinB1 binding molecules, or combination thereof, e.g., antibodies or antigen binding fragments, variants, or derivatives thereof can be used in combination with at least one or more other treatments for neuroinflammatory disorders; where the additional therapy is administered prior to, during, or subsequent to the anti-SEMA4D binding molecule, anti-PlexinB1 binding molecules, or combination thereof, e.g., antibody or antigen binding fragment, variant, or derivative thereof, therapy. Thus, where the combined therapies comprise administration of an anti-SEMA4D binding molecule, anti-PlexinB1 binding molecules, or combination thereof, e.g., an antibody or antigen binding fragment, variant, or derivative thereof, in combination with administration of another therapeutic agent, the methods of the invention encompass coadministration, using separate formulations or a single pharmaceutical formulation, with simultaneous or consecutive administration in either order.

VI. Pharmaceutical Compositions and Administration Methods

Methods of preparing and administering anti-SEMA4D binding molecules, anti-PlexinB1 binding molecules, or combination thereof, e.g., antibodies, or antigen-binding fragments, variants, or derivatives thereof to a subject in need thereof are well known to or are readily determined by those skilled in the art. The route of administration of the anti-SEMA4D binding molecule, the anti-PlexinB1 binding molecule, or combination thereof, e.g, antibody, or antigen-binding fragment, variant, or derivative thereof, can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, an example of a form for administration would be a solution for injection, in particular for intravenous or intraarterial injection or drip. A suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, anti-SEMA4D binding molecules, anti-PlexinB1 binding molecules, or combination thereof, e.g., antibodies, or antigen-binding fragments, variants, or derivatives thereof can be delivered directly to the site of the adverse cellular population thereby increasing the exposure of the diseased tissue to the therapeutic agent.

As discussed herein, anti-SEMA4D binding molecules, anti-PlexinB1 binding molecules, or combination thereof, e.g., antibodies, or antigen-binding fragments, variants, or derivatives thereof can be administered in a pharmaceutically effective amount for the in vivo treatment of neuroinflammatory disorders. In this regard, it will be appreciated that the disclosed binding molecules can be formulated so as to facilitate administration and promote stability of the active agent. In certain embodiments, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of an anti-SEMA4D binding molecule, an anti-PlexinB1 binding molecule, or combination thereof, e.g., an antibody, or antigen-binding fragment, variant, or derivative thereof, shall be held to mean an amount sufficient to achieve effective binding to a target and to achieve a benefit, e.g., to decrease the permeability of the BBB in a patient with a neuroinflammatory disorder.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01-0.1 M and preferably 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-SEMA4D antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions used in this invention can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-SEMA4D binding molecule, an anti-PlexinB1 binding molecule, or combination thereof, e.g., antibody, or fragment, variant, or derivative thereof, to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, anti-SEMA4D antibodies, or antigen-binding fragments, variants, or derivatives thereof can be administered to a human or other animal in accordance with the aforementioned methods of treatment in an amount sufficient to produce a therapeutic effect. The anti-SEMA4D antibodies, or antigen-binding fragments, variants or derivatives thereof can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-SEMA4D binding molecules, anti-PlexinB1 binding molecules, or combinations thereof, e.g., antibodies, or antigen-binding fragments, variants, or derivatives thereof, of the invention can be used.

By "therapeutically effective dose or amount" or "effective amount" is intended an amount of anti-SEMA4D binding molecule, anti-PlexinB1 binding molecule, or combination thereof, e.g., antibody or antigen binding fragment, variant, or derivative thereof, that when administered brings about a positive therapeutic response with respect to treatment of a patient with a disease to be treated, e.g., a decrease in the permeability of the BBB, an increase in the resistivity of the BBB, an increase in the number, density or concentration of endothelial cells present on the BBB, a change in the morphology or function in the endothelial cells, or a change in the interactions among endothelial cells or astrocytes or between endothelial cells and astrocytes that form the BBB.

Therapeutically effective doses of the compositions of the present invention, for the decrease in BBB permeability vary depending upon many different factors, including means of administration, target site, physiological state of the patient, whether the patient is human or an animal, other medications administered, and whether treatment is prophylactic or therapeutic. In certain embodiments the patient is a human, but non-human mammals including transgenic mammals can also be treated. Treatment dosages may be titrated using routine methods known to those of skill in the art to optimize safety and efficacy.

The amount of at least one anti-SEMA4D binding molecule, anti-PlexinB1 binding molecule, or combination thereof, e.g., antibody or binding fragment, variant, or derivative thereof, to be administered is readily determined by one of ordinary skill in the art without undue experimentation given the disclosure of the present invention. Factors influencing the mode of administration and the respective amount of at least one anti-SEMA4D binding molecule, anti-PlexinB1 binding molecule, or combination thereof, e.g., antibody, antigen-binding fragment, variant or derivative thereof include, but are not limited to, the severity of the disease, the history of the disease, and the age, height, weight, health, and physical condition of the individual undergoing therapy. Similarly, the amount of anti-SEMA4D binding molecule, anti-PlexinB1 binding molecule, or combination thereof, e.g., antibody, or fragment, variant, or derivative thereof, to be administered will be dependent upon the mode of administration and whether the subject will undergo a single dose or multiple doses of this agent.

The invention also provides for the use of an anti-SEMA4D binding molecule, an anti-PlexinB1 binding molecule, or combination thereof, e.g., antibody of the invention, or antigen-binding fragment, variant, or derivative thereof, in the manufacture of a medicament for treating a subject for treating a neuroinflammatory disorder, wherein the medicament is used in a subject that has been pretreated with at least one other therapy. By "pretreated" or "pretreatment" is intended the subject has received one or more other therapies (e.g., been treated with at least one other neuroinflammatory therapy) prior to receiving the medicament comprising the anti-SEMA4D binding molecule, an anti-PlexinB1 binding molecule, or combination thereof, e.g., antibody or antigen-binding fragment, variant, or derivative thereof "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-SEMA4D binding molecule, for example, the monoclonal antibody VX15/2503 disclosed herein, or antigen-binding fragment, variant, or derivative thereof. It is not necessary that the subject was a responder to pretreatment with the prior therapy or therapies. Thus, the subject that receives the medicament comprising the anti-SEMA4D binding molecule, an anti-PlexinB1 binding molecule, or combination thereof, e.g., an antibody or antigen-binding fragment, variant, or derivative thereof could have responded, or could have failed to respond, to pretreatment with the prior therapy, or to one or more of the prior therapies where pretreatment comprised multiple therapies.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

The following examples demonstrate the efficacy of anti-SEMA4D antibody (VX15/2503) in reducing or preventing the breakdown of the BBB, i.e., a decrease in permeability of the BBB, in an in vitro DIV-BBB model as well as in an in vivo EAE model. An in vivo Alzheimer's Disease model experiment is also disclose herein. An in depth description about the in vitro DIV-BBB model can be found in, for instance, Cucullo et al., *Brain Research.* 951 243-254

(2002); and Cucullo et al., *Journal of Cerebral Blood Flow & Metabolism.* 1-11 (2010). The in vivo EAE and Alzheimer's Disease models are disclosed, e.g., in Miller et al., *Curr Protoc Immunol.* CHAPTER: Unit-15.1, 2007; Colton et al., *J Alzheimers Dis* 15:571-587, 2008 and Wilcock et al., *J. Neuroscience,* 29:7957-7965, 2009, respectively.

Example 1: Testing the Ability of an Anti-SEMA4D Binding Molecule, e.g., an Antibody or Antigen-Binding Fragment, Variant, or Derivative Thereof, e.g., VX15/2503, to Restore the Integrity of the BBB Following SEMA4D-Induced Breakdown of the BBB in an In Vitro DIV-BBB Model Experimental Design.

A dynamic in vitro BBB ("DIV-BBB") model was performed to study the effect of recombinant human SEMA4D (huSEMA4D-his) and VX15/2503 (described in detail in US 2010/0285036 A1, incorporated herein by reference in its entirety) on the integrity of the BBB. Two DIV-BBB cartridges were tested in the model. The basic experimental design is shown in FIG. 1. Increasing concentrations of recombinant SEMA4D (rSEMA4D) were added into the lumen at 12 hour intervals, allowing for equilibration (approximately 12 hours/concentration). rSEMA4D was initially added into the lumen at a concentration of 0.05 µg/ml at time 0. The concentration of rSEMA4D increased by 10-fold at each interval, for instance, 0.5 µg/ml at 12 hours, 5.0 µg/ml at 24 hours, and 50.0 µg/ml at 36 hours. TEER measurements were taken between each interval as a reflection of changes in the permeability of the BBB at varying concentrations of rSEMA4D. Following addition of the final dose of rSEMA4D at 50.0 µg/ml at 36 hours, VX15/2503 was added into the lumen at a concentration of 250 µg/ml at 48 hours. At 72 hours, 24 hours following the addition of VX15/2503, the permeability of the BBB was again measured.

Transendothelial Electrical Resistance Measurement (TEER) was used to monitor the integrity of the BBB in real time. As mentioned above, the TEER system uses electronic multiplexing to measure multiple cartridges in quick succession and assesses the integrity and viability of tissue culture bilayers rapidly and reliably (Cucullo et al., 2002; Santaguida et al, 2006). In this dynamic in vitro model, the cartridges, or hollow tubes, were set up to represent the blood brain barrier with the interior of the cartridge representing the blood side of the blood brain barrier and the exterior of the cartridge representing the brain side of the blood brain barrier. The interior of the cartridge was lined with adult human brain microvascular endothelial cells and the exterior was lined with human adult astrocytes. As a blood brain barrier modifying agent, such as SEMA4D, was introduced into the lumen of the cartridge, the electrical current between the interior and exterior of the tube was monitored using TEER. In operation, the TEER system applies an excitation voltage (0.06V) across the excitation electrodes inserted in each cartridge in the luminal and extraluminal compartments. A microcontroller computes the resistivity and capacitance (per $cm^2$) of the barrier from physical parameters. The values of capacitance are calculated by comparison of the voltage and current waveforms. The delay from peak-to-peak of the two waveforms is proportional to the capacitance value, which is expressed as arch tension. The TEER was measured from the initial setup throughout the course of each experiment.

rSEMA4D-induced Increase in Permeability of the BBB.

Following formation of the BBB, the effect of rSEMA4D on the integrity of the BBB was measured by adding increasing concentrations of recombinant SEMA4D (rSEMA4D) into the lumen of the two cartridges. rSEMA4D was initially added into the lumen at a concentration of 0.05 µg/ml at time 0. The concentration of rSEMA4D was increased 10-fold at each 12 hour interval, for instance, 0.5 µg/ml at 12 hours, 5 µg/ml at 24 hours and 50.0 µg/ml at 36 hours. TEER measurements were taken between and during each interval as a reflection of changes in the permeability of the BBB at varying concentrations of rSEMA4D. Overall, permeability of the BBB remained relatively stable at 0.05 µg/ml of rSEMA4D. Starting at 0.5 µg/ml, increasing concentrations of rSEMA4D (i.e., 0.5 µg/ml, 5 µg/ml and 50 µg/ml) resulted in decreased TEER measurement reflecting increased permeability of the endothelial cell layer. These results are shown in FIG. 2.

Antibody-Induced Decrease in Permeability of rSEMA4D Treated BBB.

To measure the effect of an anti-SEMA4D antibody on the BBB following exposure to escalating dosage of rSEMA4D, VX15/2503 was added at a concentration of 250 µg/ml at 48 hours. TEER measurements were taken at 72 hours. Treatment with VX15/2503 resulted in an overall decrease in permeability (or increase in resistivity) of the BBB in the two cartridges. This decrease in permeability reflects restoration of the BBB. The results are shown in FIG. 2.

Example 2: Testing the Ability of an Anti-SEMA4D Binding Molecule, e.g., an Antibody or Antigen-Binding Fragment, Variant, or Derivative Thereof, e.g., VX15/2503, to Restore the Integrity of the BBB Following SEMA4D-Induced Breakdown of the BBB in an In Vitro DIV-BBB Model Experimental Design.

A second experiment employing the in vitro DIV-BBB model was performed to study the effect of SEMA4D and VX15/2503 on the integrity of the BBB. The basic experimental design was similar to that shown in Example 1, and FIG. 1, above. For two weeks, the DIV-BBB cartridges underwent BBB formation in endothelial and astrocytic cell compartments. The formation of the BBB as reflected in TEER is shown in FIGS. 3 and 4.

rSEMA4D-Induced Increase in Permeability of the BBB.

Following formation of the BBB, the effect of rSEMA4D on the integrity of the BBB was measured by adding increasing concentrations of recombinant SEMA4D (rSEMA4D) into the lumen of the first cartridge of a set of three cartridges at 12 hour intervals, allowing for equilibration (approximately 12 hours/concentration). rSEMA4D was initially added into the lumen at a concentration of 0.5 µg/ml at time 0. The concentration of rSEMA4D increased by 10-fold at each interval, for instance, 5 µg/ml at 12 hours and 50.0 µg/ml at 24 hours. TEER measurements were taken between each interval as a reflection of changes in the permeability of the BBB at varying concentrations of rSEMA4D. Overall, increasing concentrations of rSEMA4D resulted in decreased TEER measurement reflecting increased permeability of the BBB. These results are shown in FIG. 3.

To test the integrity of the BBB in the presence of an antigen that does not target the endothelial cell layer, a similarly prepared recombinant protein control (CTRL, C35 protein) was added at equimolar concentrations at the same 12 hour intervals (i.e., 0.25 μg/ml at time 0, 2.5 μg/ml at 12 hours, and 25.0 μg/ml at 24 hours) to the two additional control cartridges. In contrast to the effect of rSEMA4D, the CTRL protein did not induce a significant change in TEER reflecting no meaningful change in permeability of the BBB. If, however, 50.0 μg/ml of rSEMA4D was added 12 hours after addition of the highest concentration of CTRL protein, a rapid decrease in TEER similar to that observed with escalating doses of rSEMA4D was induced. The results are shown in FIG. 4.

Antibody-Induced Decrease in Permeability of rSEMA4D Treated BBB.

Following addition of the final dose of rSEMA4D at 50.0 μg/ml at 24 hours, the effect of VX15/2503 on TEER and the permeability of the BBB was measured. In FIG. 3, VX15/2503 antibody was added at a concentration of 250 μg/ml at 36 hours to two of the three cartridges that received escalating doses of rSEMA4D while the same concentration of an isotype control antibody was added to the one remaining cartridge that had received escalating doses of rSEMA4D. TEER measurements were taken at various subsequent points of time. Treatment with VX15/2503 resulted in an increase in TEER back to peak levels at the start of the experiment, reflecting an overall decrease in permeability of the BBB (i.e., restoration of the BBB). In the one cartridge that received isotype control antibody, TEER levels remained at the relatively reduced levels induced by treatment with rSEMA4D, indicating no meaningful decrease in permeability of the BBB. Similar results are shown in FIG. 4. In FIG. 4, VX15/2503 antibody was added at a concentration of 250 μg/ml at 48 hours to the two cartridges that received initial control recombinant C35 protein followed by 50 μg/ml of rSEMA4D for 12 hours. Treatment with VX15/2503 resulted in an increase in TEER back to peak levels at the start of the experiment, reflecting an overall decrease in permeability of the BBB (i.e., restoration of the BBB).

Example 3: Testing the Ability of an Anti-Plexin-B1 Binding Molecule, e.g., an Antibody or Antigen-Binding Fragment, Variant, or Derivative Thereof, to Restore the Integrity of the BBB Following SEMA4D-Induced Breakdown of the BBB in an In Vitro DIV-BBB Model Another study was conducted to measure the effects of anti-Plexin-B1 antibody (MAB37491 Human Plexin-B1 MAb (Clone 559830), R&D Systems) on the integrity of the BBB. This antibody blocks binding of SEMA4D to the Plexin-B1 receptor. The results of this study are shown in FIG. 5. As shown in FIG. 5, human endothelial cells and astrocytes in four DIV-BBB cartridges underwent BBB formation similar to the experiments described above. After BBB formation, rSEMA4D was added at a concentration of 50.0n/ml, inducing an increase in BBB permeability (i.e., destruction of the BBB). Following addition of rSEMA4D, anti-Plexin-B1 antibody was added at a concentration of 125 μg/ml at 6 hours to two of the four cartridges, VX15/2503 antibody was added at a concentration of 250 μg/ml to one of the four cartridges, and isotype control antibody was added at a concentration of 250 μg/ml to the remaining cartridge. TEER measurements were taken at various subsequent points of time. Treatment with either VX15/2503 or anti-Plexin-B1 antibody resulted in an increase in TEER levels with both agents. Treatment with VX15/2503 resulted in a somewhat greater increase in TEER than treatment with anti-Plexin-B1 antibody at the last time point. The effect of the two antibodies is indistinguishable at all other time points. The increase in TEER reflects an overall decrease in permeability of the BBB (i.e., restoration of the BBB) in the presence of either VX15/2503 or anti-Plexin-B1 antibody. In the one cartridge that received isotype control antibody, TEER levels remained at the relatively reduced levels induced by treatment with rSEMA4D, indicating no meaningful decrease in permeability of the BBB. It should be appreciated that treatment can also be conducted using a combination of VX15/2503 and anti-Plexin-B1.

Example 4: Testing the Ability of an Anti-SEMA4D Binding Molecule, e.g., an Antibody or Antigen-Binding Fragment, Variant, or Derivative Thereof, e.g., VX15/2503, to Restore the Integrity of the BBB Following Breakdown of the BBB Induced by Activated PBMC and Flow Cessation in an In Vitro DIV-BBB Model Experimental Design.

Another experiment employing the in vitro DIV-BBB model was performed to study the effect of VX15/2503 on restoring the integrity of the BBB following breakdown of the BBB induced by activated peripheral blood mononuclear cells (PBMC) and flow cessation. For two weeks, two DIV-BBB cartridges underwent BBB formation in endothelial and astrocytic cell compartments.

Activated PBMC-Induced Increase in Permeability of the BBB.

Following formation of the BBB, the effect of activated PBMC on the integrity of the BBB was measured. PBMC were activated with PMA/ionomycin for 2 hours and then added at a concentration of $10^6$/ml into the lumen of the two cartridges. TEER measurements were taken prior to and after the addition of the activated PBMC as a reflection of changes in the permeability of the BBB. Overall, adding activated PBMC to the cartridges at $10^6$/ml resulted in decreased TEER measurement reflecting increased permeability of the BBB. These results are shown in FIG. 6.

At approximately 2-4 hours following the addition of the activated PBMC to the cartridges, flow cessation was performed for 1 hour. TEER measurements were taken before and after flow cessation as a reflection of changes in the permeability of the BBB. Overall, flow cessation resulted in a further decrease in TEER measurement reflecting increased permeability of the BBB. These results are also shown in FIG. 6.

Antibody-Induced Decrease in Permeability of the BBB Exposed to Activated PBMC.

Following exposure to activated PBMC and flow cessation, the effect of VX15/2503 on TEER and the permeability of the BBB was measured. VX15/2503 antibody was added at a concentration of 250 μg/ml to one of the two cartridges that received activated PBMC while the same concentration of an isotype control antibody (Isotype Control Ig, 2269) was added to the remaining cartridge. TEER measurements were taken at various subsequent points of time. As shown in FIG. 6, treatment with VX15/2503 resulted in an increase in TEER back to peak levels at the start of the experiment, reflecting an overall decrease in permeability of the BBB (i.e., restoration of the BBB). In the cartridge that received isotype control antibody, TEER levels remained at the relatively reduced levels induced by treatment with activated PBMC and flow cessation, indicating no meaningful decrease in the permeability of the BBB.

Example 5: Testing the Ability of an Anti-SEMA4D Binding Molecule, e.g., an Antibody or Antigen-Binding Fragment, Variant, or Derivative Thereof, e.g., VX15/2503, to Protect the Integrity of the BBB in an In Vivo EAE Model Anti-SEMA4D binding molecules, e.g., antibodies or antigen-binding fragments, variants or derivatives thereof, e.g., VX15/2503, were tested in the in vivo experimental autoimmune encephalomyelitis (EAE) model.

In an in vivo EAE model, the breakdown of the BBB was investigated by examining changes in brain permeability as reflected in the penetration of fibrinogen from blood into the brain parenchyma and through examination of endothelial tight junction proteins, including Claudin-5. In this model, EAE was induced in mice by immunization with PLP peptide (139-151). Of course, those skilled in the art will appreciate that other EAE inducing proteins may be used as well (e.g., a myelin antigen, for instance myelin-oligodendrocyte glycoprotein peptide 35-55) and that, for greatest efficiency, these inducing proteins or peptides may vary from one species to another and from one strain of mice to another, Steinman, L. Neuron 24:511-514 (1999). Tissue sections from the central nervous system (CNS) of animals at different stages of disease were then immunostained for proteins (fibrinogen and claudin-5, which serve as markers for BBB disruption).

Experimental Design.

In an in vivo EAE model, EAE was induced in 12 week old SJL/J mice (10 mice per group) by immunization with PLP peptide (139-151) in CFA (complete Freund's adjuvant). The mice were then treated once per week from 7 days post-induction with 600 µg anti-SEMA4D antibody (VX15/2503 antibody) or control IgG. Neurological signs were first observed at 11d postinduction (dpi). At 13 days postinduction, during the acute phase of disease, 4 mice per group were sacrificed and lumbar spinal cord samples were prepared for histopathologic analysis. To detect BBB disruption in the samples, these samples were immunostained for fibrinogen and claudin-5. The procedure for immunostaining is as follows: Sections were rinsed twice in PBS, then incubated in PBS 0.1% glycine 10 min, blocked in PBS 0.3% Triton X-100 10% goat serum for 1 h, and incubated with primary Abs in blocking buffer overnight at 4° C. For claudin-5 (CLN-5), prior to blocking, sections were soaked in EDTA, pH 8, 100° C. Primary antibodies used were anti-CLN-5 (1:50), and anti-fibrinogen (1:1,000). After washing three times in PBS 0.3%, Triton X-100 sections were then incubated in relevant species specific secondary antibodies conjugated to AlexaFluor 488 and/or AlexaFluor 594 (1/100; Molecular Probes) in blocking buffer for 1 h at 25° C., washed again three times, and counterstained with 4,6-diamidino-2-phenylindole (DAPI). All samples were examined and photographed using a Zeiss LSM 510 META laser scanning confocal system attached to an Axiovert 200 inverted fluorescence microscope.

Clinical disease in the mice was scored as follows: 0=no symptoms; 1=floppy tail; 2=hind limb weakness; 4=fore and hind limb weakness; 5=death. Neurological signs were first observed at 11 days postinduction. In the mice treated with the VX15/2503 antibody, clinical disease reached a mean severity score of 0.75, indicative of mild tail weakness, while clinical disease in mice of the control group reached a mean severity scope of 2.25, indicative of paraparesis.

Results of the immunostaining at 13 days postinduction are shown in FIGS. 7A-7C. Fibrinogen does not normally penetrate the blood-brain brain barrier (BBB). In EAE, with the BBB compromised, the green fibrinogen stain was detected in brain matter (left panel). In addition, expression of claudin-5 (CLN-5, red stain), a component of the tight junctions that make up the BBB, was reduced. Mice in the control group showed reduced expression of claudin-5 and increased levels of extravascular leakage of fibrinogen, which correlated with a disruption in the BBB. In mice treated with VX15/2503 antibody, on the other hand, expression of claudin-5 was maintained and leakage of fibrinogen was significantly reduced. These results demonstrated the protective effect of VX15/2503 antibody against disruption of the BBB in these treated mice, and specifically demonstrated how anti-SEMA4D antibody prevents BBB breakdown, prevents extravascular leakage of fibrinogen (7A left panel and quantitation in 7B), and preserves claudin-5 as detected by red stain (7A right panel and quantitation in 7C).

Example 6: Effect of SEMA4D on Tight Junction Proteins in Cultures of Cerebral Endothelial Cells Experimental Design.

The expression of the key endothelial tight junction protein Claudin-5 following treatment of CNS derived endothelial cells with soluble recombinant SEMA4D was investigated. In this model, primary mouse central nervous system (CNS) endothelial cultures were isolated and plated on a 6-well matrigel-coated plate (isolated MBCEC from 10 brains were resuspended in 3 ml primary endothelial cell culture medium and plated at 250 ul per well). Cultures were used at day 7 after isolation. Cultures were treated with 1 ng/ml, 10 ng/ml or 100 ng/ml recombinant mouse SEMA4D or 100 ng/ml mouse VEGF-A (positive control) for 24 hours. The endothelial cultures of the animals were then subjected to SDS-polyacrylamide gel electrophoresis (SDS-PAGE) and immunoblotting for the claudin-5 tight junction protein and actin loading control. Data were scanned and subjected to densitometry using ImageJ software (NIH).

Results of immunoblotting are shown in FIG. 8. As provided in FIG. 8, endothelial cell cultures treated with 100 ng/ml of recombinant SEMA4D showed a significant reduction in Claudin-5 protein expression. Endothelial cell cultures treated with 100 ng/ml of VEGF-A were tested as a positive control for down-regulation of Claudin-5. This demonstrates the important role of SEMA4D in regulating expression of a key tight junction protein of the BBB.

Example 7: Testing the Ability of an Anti-SEMA4D or Anti-PlexinB1 Binding Molecule, e.g., an Antibody or Antigen-Binding Fragment, Variant, or Derivative Thereof to Decrease the Permeability of the BBB in an In Vivo Alzheimer's Disease (AD) Model Anti-SEMA4D or Anti-PlexinB1 binding molecules, e.g., antibodies or antigen-binding fragments, variants or derivatives thereof, e.g., MAb 67 (described in detail in US 2010/0285036 A1, incorporated herein by reference in its entirety), are tested in various model systems of neuroinflammatory disorders, including, but not limited to an in vivo experimental Alzheimer's disease (AD) transgenic mouse model APPSwDI/NOSC$^{-/-}$. These mice were generated by crossing APP-Swedish-Dutch-Iowa mutant mouse with nitric oxide synthase 2 knock-out mouse (Colton et al., J Alzheimers Dis. 15:571-587, 2008; Van Nostrand et al., Stroke 41:S135-S138, 2010). APPSwDI/NOSC$^{-/-}$ mice develop age-related neurovascular amyloidosis with disrupted BBB function, intraparenchymal amyloid plaques, mouse tau hyperphosphorylation, neuroinflammation, neuronal cell death, and cognitive deficits. Wilcock et al. have shown that treatment of APPSwDI/NOSC$^{-/-}$ mice with amyloid-beta directed active immunotherapy leads to marked reduction in amyloid deposition, but with increased incidence of microhemorrhages (Wilcock et al., *J Neurosci.* 29:7957-7965, 2009).

In an in vivo AD model, the progression of AD is investigated by examining immunohistochemical signatures of amyloid deposition, tau hyperphosphorylation, and BBB leakage (fibrinogen), as well as by assessing cognitive abilities in spatial memory-based behavioral paradigms. In this model, the transgenic mice are administered MAb 67 or Control Ig (Mab 2B8) intravenously at a concentration of 30 mg/kg from age 26 to 38 weeks for a total of 13 doses.

The mice are initially subjected to baseline behavioral testing at age 10-12 weeks, e.g., Open field, RAWn and Barnes Maze tests, and mice reaching the criteria of activity and learning/memory are included in the follow-up. Behavioral deficits are again measured at age 38, 39 and 40 weeks and body weight is recorded. Mice that do not reach criteria for study enrollment will be sacrificed. At the 41 week of age end-point, the animals will be euthanized and the brains will be processed for biochemical and immunohistological analyses for soluble and insoluble amyloid beta levels and deposits. Serum is collected pre-dosing, during dosing and at the end-point for PK at age 10, 25 and 41 weeks. Tissue sections from the central nervous system (CNS) of animals at different stages of disease may be immunostained for fibrinogen, that can be used as markers for BBB disruption.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

What is claimed is:

1. A method of decreasing blood brain barrier permeability in a subject with increased blood brain barrier permeability associated with a neuroinflammatory disorder selected from the group consisting of Amyotrophic Lateral Sclerosis, epilepsy, Alzheimer's Disease, Parkinson's Disease, and meningitis, comprising administering to the subject an effective amount of an isolated antibody or antigen-binding fragment thereof, wherein the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively, and wherein the antibody or antigen-binding fragment thereof specifically binds to semaphorin-4D (SEMA4D) and inhibits SEMA4D interaction with a SEMA4D receptor, and wherein administration of the antibody or antigen-binding fragment thereof maintains or increases Claudin-5 expression, thereby decreasing blood brain barrier permeability in the subject.

2. The method of claim 1, wherein the SEMA4D receptor is Plexin-B1.

3. The method of claim 1, wherein the antibody or antigen-binding fragment thereof competitively inhibits a reference monoclonal antibody comprising the variable heavy chain (VH) amino acid sequence SEQ ID NO: 9 and the variable light chain (VL) amino acid sequence SEQ ID NO: 17 from specifically binding to SEMA4D.

4. The method of claim 1, wherein the antibody or antigen-binding fragment thereof specifically binds to the same SEMA4D epitope as a reference monoclonal antibody comprising the VH amino acid sequence SEQ ID NO: 9 and the VL amino acid sequence SEQ ID NO: 17.

5. The method of claim 1, wherein the antibody or antigen-binding fragment thereof comprises a VH and a VL comprising the amino acid sequences SEQ ID NO: 9 and SEQ ID NO: 17 or SEQ ID NO: 10 and SEQ ID NO: 18, respectively.

6. A method of increasing or maintaining Claudin-5 expression in a subject with increased blood brain barrier permeability associated with a neuroinflammatory disorder selected from the group consisting of Amyotrophic Lateral Sclerosis, epilepsy, Alzheimer's Disease, Parkinson's Disease, and meningitis, comprising diagnosing a subject with Amyotrophic Lateral Sclerosis, epilepsy, Alzheimer's Disease, Parkinson's Disease, or meningitis with increased blood brain barrier permeability, and administering to the subject an effective amount of an isolated antibody or antigen-binding fragment thereof, wherein the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively, and wherein the antibody or antigen-binding fragment thereof specifically binds to semaphorin-4D (SEMA4D) and inhibits SEMA4D interaction with a SEMA4D receptor, and wherein administration of the antibody or antigen-binding fragment thereof maintains or increases Claudin-5 expression, thereby decreasing blood brain barrier permeability in the subject.

7. The method of claim 6, wherein the antibody or antigen-binding fragment thereof competitively inhibits a reference monoclonal antibody comprising the variable heavy chain (VH) amino acid sequence SEQ ID NO: 9 and the variable light chain (VL) amino acid sequence SEQ ID NO: 17 from specifically binding to SEMA4D.

8. The method of claim 6, wherein the antibody or antigen-binding fragment thereof specifically binds to the same SEMA4D epitope as a reference monoclonal antibody comprising the VH amino acid sequence SEQ ID NO: 9 and the VL amino acid sequence SEQ ID NO: 17.

9. The method of claim 6, wherein the antibody or antigen-binding fragment thereof comprises a VH and a VL comprising the amino acid sequences SEQ ID NO: 9 and SEQ ID NO: 17 or SEQ ID NO: 10 and SEQ ID NO: 18, respectively.

* * * * *